United States Patent
van Rooyen et al.

(10) Patent No.: US 10,622,097 B2
(45) Date of Patent: Apr. 14, 2020

(54) BIOINFORMATICS SYSTEMS, APPARATUSES, AND METHODS EXECUTED ON AN INTEGRATED CIRCUIT PROCESSING PLATFORM

(71) Applicant: EDICO GENOME, CORP., La Jolla, CA (US)

(72) Inventors: Pieter van Rooyen, La Jolla, CA (US); Michael Ruehle, La Jolla, CA (US); Robert McMillen, La Jolla, CA (US)

(73) Assignee: EDICO GENOME, CORP., La Jolla, CA (US)

( * ) Notice: Subject to any disclaimer, the term of this patent is extended or adjusted under 35 U.S.C. 154(b) by 0 days.

(21) Appl. No.: 16/140,469

(22) Filed: Sep. 24, 2018

(65) Prior Publication Data

US 2019/0172552 A1 Jun. 6, 2019

Related U.S. Application Data

(60) Continuation of application No. 15/144,734, filed on May 2, 2016, now Pat. No. 10,083,276, which is a
(Continued)

(51) Int. Cl.
*G06F 19/00* (2018.01)
*G16B 50/00* (2019.01)
(Continued)

(52) U.S. Cl.
CPC .............. *G16B 50/00* (2019.02); *G06F 13/16* (2013.01); *G06F 13/4068* (2013.01);
(Continued)

(58) Field of Classification Search
CPC ..................................................... G06F 19/23
See application file for complete search history.

(56) References Cited

U.S. PATENT DOCUMENTS 5,859,972 A 1/1999 Subramaniam
5,964,072 A 10/1999 Rasmussen
(Continued)

FOREIGN PATENT DOCUMENTS

CN 103293209 9/2013
CN 105051741 4/2018
(Continued)

OTHER PUBLICATIONS

**Alachiotis, N. et al., "Accelerating Phylogeny-Aware Short DNA Read Alignment with FPGAs", The Exelixis Lab, Scientific Computing Group, 2011, 8 pages.
(Continued)

Primary Examiner — Jyoti Nagpaul
(74) Attorney, Agent, or Firm — Fish & Richardson P.C.

(57) ABSTRACT

A system, method and apparatus for executing a sequence analysis pipeline on genetic sequence data includes a structured ASIC formed of a set of hardwired digital logic circuits that are interconnected by physical electrical interconnects. One of the physical electrical interconnects forms an input to the structured ASIC connected with an electronic data source for receiving reads of genomic data. The hardwired digital logic circuits are arranged as a set of processing engines, each processing engine being formed of a subset of the hardwired digital logic circuits to perform one or more steps in the sequence analysis pipeline on the reads of genomic data. Each subset of the hardwired digital logic circuits is formed in a wired configuration to perform the one or more steps in the sequence analysis pipeline.

18 Claims, 13 Drawing Sheets

Related U.S. Application Data continuation of application No. 14/948,372, filed on Nov. 22, 2015, now Pat. No. 9,342,652, which is a division of application No. 14/284,307, filed on May 21, 2014, now Pat. No. 9,235,680, which is a continuation of application No. 14/279,063, filed on May 15, 2014, now Pat. No. 9,679,104, which is a continuation-in-part of application No. 14/158,758, filed on Jan. 17, 2014, now Pat. No. 9,483,610.

(60) Provisional application No. 61/988,128, filed on May 2, 2014, provisional application No. 61/984,663, filed on Apr. 25, 2014, provisional application No. 61/943,870, filed on Feb. 24, 2014, provisional application No. 61/910,868, filed on Dec. 2, 2013, provisional application No. 61/823,824, filed on May 15, 2013, provisional application No. 61/822,101, filed on May 10, 2013, provisional application No. 61/826,381, filed on May 22, 2013, provisional application No. 61/753,775, filed on Jan. 17, 2013.

(51) Int. Cl.

| | | |
|---|---|---|
| *H01L 21/768* | (2006.01) | |
| *G16B 30/00* | (2019.01) | |
| *G16B 40/00* | (2019.01) | |
| *H01L 27/118* | (2006.01) | |
| *H03K 19/17736* | (2020.01) | |
| *H01L 23/528* | (2006.01) | |
| *H01L 27/02* | (2006.01) | |
| *G06F 13/16* | (2006.01) | |
| *G06F 13/40* | (2006.01) | |
| *G06F 13/42* | (2006.01) | |

(52) U.S. Cl.
CPC ......... *G06F 13/4265* (2013.01); *G16B 30/00* (2019.02); *G16B 40/00* (2019.02); *H01L 21/768* (2013.01); *H01L 21/76886* (2013.01); *H01L 23/528* (2013.01); *H01L 27/0207* (2013.01); *H01L 27/118* (2013.01); *H01L 27/11807* (2013.01); *H03K 19/17736* (2013.01); *H01L 2027/11838* (2013.01); *H01L 2027/11883* (2013.01)

(56) References Cited

U.S. PATENT DOCUMENTS

| | | | |
|---|---|---|---|
| 6,112,288 | A | 8/2000 | Ullner |
| 6,253,529 | B1 | 7/2001 | De Boer et al. |
| 6,681,186 | B1 | 1/2004 | Denisov |
| 7,135,701 | B2 | 11/2006 | Amin et al. |
| 7,533,068 | B2 | 5/2009 | Maassen et al. |
| 7,680,790 | B2 | 3/2010 | Fleurantin et al. |
| 7,917,299 | B2 | 3/2011 | Buhler et al. |
| 7,917,302 | B2 | 3/2011 | Rognes |
| 7,948,015 | B2 | 5/2011 | Rothberg |
| 7,969,805 | B2 | 6/2011 | Thom et al. |
| 8,190,548 | B2 | 5/2012 | Choi |
| 8,195,596 | B2 | 6/2012 | Rose et al. |
| 8,209,130 | B1 | 6/2012 | Kennedy et al. |
| 8,217,433 | B1 | 7/2012 | Fife et al. |
| 8,280,640 | B2 | 10/2012 | Levin et al. |
| 8,445,945 | B2 | 5/2013 | Rothberg et al. |
| 8,524,487 | B2 | 9/2013 | Fife et al. |
| 8,558,288 | B2 | 10/2013 | Rothberg et al. |
| 8,560,282 | B2 | 10/2013 | Macready et al. |
| 8,594,951 | B2 | 11/2013 | Homer |
| 8,620,923 | B1 | 12/2013 | Wormley et al. |
| 8,700,689 | B2 | 4/2014 | Macready et al. |
| 8,738,105 | B2 | 5/2014 | Berkley et al. |
| 8,751,166 | B2 | 6/2014 | Friedlander et al. |
| 8,936,763 | B2 | 1/2015 | Rothberg et al. |
| 9,014,989 | B2 | 4/2015 | McMillen et al. |
| 9,026,574 | B2 | 5/2015 | Macready et al. |
| 9,235,680 | B2 | 1/2016 | Van Rooyen et al. |
| 9,355,365 | B2 | 5/2016 | Berkley et al. |
| 9,405,876 | B2 | 8/2016 | Macready et al. |
| 9,483,610 | B2 | 11/2016 | Mcmillen et al. |
| 9,576,103 | B2 | 2/2017 | Mcmillen et al. |
| 9,618,474 | B2 | 4/2017 | Van Rooyen et al. |
| 9,679,104 | B2 | 6/2017 | Van Rooyen et al. |
| 9,792,405 | B2 | 10/2017 | Van Rooyen et al. |
| 2003/0033279 | A1 | 2/2003 | Gibson et al. |
| 2003/0033501 | A1 | 2/2003 | Cooke |
| 2003/0039362 | A1 | 2/2003 | Califano et al. |
| 2003/0104470 | A1 | 6/2003 | Fors et al. |
| 2004/0024536 | A1 | 2/2004 | Rognes |
| 2004/0059721 | A1 | 3/2004 | Patzer |
| 2004/0098203 | A1 | 5/2004 | Rognes |
| 2004/0126840 | A1 | 7/2004 | Cheng et al. |
| 2005/0060195 | A1 | 3/2005 | Bessette |
| 2005/0131649 | A1 | 6/2005 | Larsen et al. |
| 2006/0225165 | A1 | 10/2006 | Van den Brink |
| 2007/0038381 | A1 | 2/2007 | Melchior |
| 2007/0078897 | A1 | 4/2007 | Hayashi |
| 2007/0088510 | A1 | 4/2007 | Li et al. |
| 2007/0196816 | A1 | 8/2007 | Schwartz et al. |
| 2008/0005024 | A1 | 1/2008 | Kirkwood |
| 2008/0086274 | A1 | 4/2008 | Chamberlain et al. |
| 2008/0176750 | A1 | 7/2008 | Rose et al. |
| 2008/0250016 | A1 | 10/2008 | Farrar |
| 2009/0121215 | A1 | 5/2009 | Choi |
| 2009/0125248 | A1 | 5/2009 | Shams et al. |
| 2009/0171647 | A1 | 7/2009 | Mannava et al. |
| 2009/0253130 | A1 | 10/2009 | Yoo |
| 2010/0077267 | A1 | 3/2010 | Perego |
| 2010/0082805 | A1 | 4/2010 | Orton et al. |
| 2010/0085827 | A1 | 4/2010 | Thom et al. |
| 2010/0169313 | A1 | 7/2010 | Kenedy |
| 2010/0281401 | A1 | 11/2010 | Tebbs et al. |
| 2010/0327847 | A1 | 12/2010 | Leiber et al. |
| 2011/0004413 | A1 | 1/2011 | Carnevali et al. |
| 2011/0093581 | A1 | 4/2011 | Venkatachalam |
| 2011/0184235 | A1 | 7/2011 | Schostek et al. |
| 2011/0227043 | A1 | 9/2011 | Guo et al. |
| 2012/0001615 | A1 | 1/2012 | Levine |
| 2012/0089339 | A1 | 4/2012 | Ganeshalingam |
| 2012/0102041 | A1 | 4/2012 | Park |
| 2012/0109849 | A1 | 5/2012 | Chamberlain et al. |
| 2012/0149981 | A1 | 6/2012 | Khait et al. |
| 2012/0214172 | A1 | 8/2012 | Chen et al. |
| 2013/0018599 | A1 | 1/2013 | Peng |
| 2013/0091121 | A1 | 4/2013 | Galinsky |
| 2013/0110407 | A1 | 5/2013 | Baccash et al. |
| 2013/0124100 | A1 | 5/2013 | Drmanac et al. |
| 2013/0144925 | A1 | 6/2013 | Macready et al. |
| 2013/0157870 | A1 | 6/2013 | Pushkarev et al. |
| 2013/0194882 | A1 | 8/2013 | Ishii et al. |
| 2013/0245958 | A1 | 9/2013 | Forster et al. |
| 2013/0254202 | A1 | 9/2013 | Friedlander |
| 2013/0296175 | A1 | 11/2013 | Rafnar |
| 2013/0297221 | A1 | 11/2013 | Johnson et al. |
| 2013/0307029 | A1 | 11/2013 | Xu et al. |
| 2013/0311106 | A1 | 11/2013 | White et al. |
| 2013/0316331 | A1 | 11/2013 | Isakov et al. |
| 2013/0324417 | A1 | 12/2013 | Kennedy et al. |
| 2013/0332081 | A1 | 12/2013 | Reese et al. |
| 2013/0338012 | A1 | 12/2013 | Sulem et al. |
| 2013/0338934 | A1 | 12/2013 | Asadi et al. |
| 2014/0024537 | A1 | 1/2014 | Rigatti |
| 2014/0033125 | A1 | 1/2014 | Merel et al. |
| 2014/0045705 | A1 | 2/2014 | Bustamante et al. |
| 2014/0046926 | A1 | 2/2014 | Walton et al. |
| 2014/0051588 | A9 | 2/2014 | Drmanac et al. |
| 2014/0081665 | A1 | 3/2014 | Holmes |
| 2014/0114582 | A1 | 4/2014 | Mittelman et al. |
| 2014/0121116 | A1 | 5/2014 | Richards et al. |
| 2014/0164516 | A1 | 6/2014 | Maltbie et al. |
| 2014/0200166 | A1 | 7/2014 | Van Rooyen et al. |
| 2014/0297196 | A1 | 10/2014 | Olson |

(56) References Cited

U.S. PATENT DOCUMENTS

| | | |
|---|---|---|
| 2014/0304276 A1 | 10/2014 | Boyce |
| 2014/0309944 A1 | 10/2014 | Van Rooyen et al. |
| 2014/0310215 A1 | 10/2014 | Trakadis |
| 2014/0316716 A1 | 10/2014 | Jiang et al. |
| 2014/0337052 A1 | 11/2014 | Pellini et al. |
| 2014/0350968 A1 | 11/2014 | Hahn et al. |
| 2014/0368550 A1 | 12/2014 | Vaske et al. |
| 2014/0371109 A1 | 12/2014 | McMillen et al. |
| 2014/0371110 A1 | 12/2014 | Van Rooyen et al. |
| 2015/0066824 A1 | 3/2015 | Harris et al. |
| 2015/0123600 A1 | 5/2015 | Groat et al. |
| 2015/0142334 A1 | 5/2015 | Mishra |
| 2015/0154406 A1 | 6/2015 | Naehrig et al. |
| 2015/0248525 A1 | 9/2015 | Ury |
| 2015/0286495 A1 | 10/2015 | Lee et al. |
| 2015/0310163 A1 | 10/2015 | Kingsmore et al. |
| 2015/0339437 A1 | 11/2015 | McMillen et al. |
| 2016/0046986 A1 | 2/2016 | Eltoukhy |
| 2016/0092631 A1 | 3/2016 | Yandell et al. |
| 2016/0140290 A1 | 5/2016 | Van Rooyen et al. |
| 2016/0171153 A1 | 6/2016 | Van Rooyen et al. |
| 2016/0178569 A1 | 6/2016 | Hoffman et al. |
| 2016/0283407 A1 | 9/2016 | Van Rooyen et al. |
| 2016/0306923 A1 | 10/2016 | Van Rooyen et al. |
| 2017/0270245 A1 | 9/2017 | Van Rooyen et al. |
| 2017/0308644 A1 | 10/2017 | Van Rooyen et al. |
| 2018/0196916 A1 | 7/2018 | Van Rooyen et al. |
| 2018/0239865 A1 | 8/2018 | Van Rooyen et al. |

FOREIGN PATENT DOCUMENTS

| | | |
|---|---|---|
| EP | 2313523 | 4/2011 |
| WO | WO2011/149534 | 12/2011 |
| WO | WO2012/122546 | 9/2012 |
| WO | WO2013/128371 | 9/2013 |
| WO | WO2014/060305 | 4/2014 |
| WO | WO2014/074246 | 5/2014 |
| WO | WO2014113736 | 7/2014 |
| WO | WO2014/121091 | 8/2014 |
| WO | WO2014/186604 | 11/2014 |
| WO | WO2015/051006 | 4/2015 |
| WO | WO2015/089333 | 6/2015 |
| WO | WO2015/100427 | 7/2015 |
| WO | WO2015123600 | 8/2015 |

OTHER PUBLICATIONS

\*\*Altera Corp, "Implementation of the Smith-Waterman Algorithm on a Reconfigurable Supercomputing Platform", White Paper, vol. 1, 2007, 18 pages.

Angiuoli, S. et al., "Mugsey; fast multiple alignment of closely related whole genomes", Bioinformatics (2011) 27(3); http://bioinformatics.oxfordjournals.org/content/27/3/334 URL retrieved May 25, 2016, Dec. 9, 2010, 334-342.

Anonymous, "FPGA-accelerated Bioinformatics at #ASHG—Dragen Aligner from Edico Genome", http://homolog.us/blogs/blog/2014/10/20/fpga-accelerated-bioinformatics-at-ashg-dragen-aligner-from-edico-genome/#, Oct. 20, 2014.

Benkrid, K. et al., "A Highly Parameterized and Efficient FPGA-Based Skeleton for Pairwise Biological Sequence Alignment", IEEE Transactions on VLSI Sysytems, Apr. 2009, 561-570.

Benkrid, K. et al., "High Performance Biological Pairwise Sequence Alignment: FPGA versus GPU versus Cell BE versus GPP", Hindawi Publishing Corporation, vol. 2012, 2012, 16 pages.

Buyukkurt, B. et al., "Compiler Generated Systolic Arrays for Wavefront Algorithm Acceleration on FPGAS", International Conference on Field Programmable Logic and Applications, 2008, 4 pages.

Carneiro, M. "Accelerating variant calling", Intel Genomic Sequencing Pipeline Workshop, Dec. 10, 2013, 26 pages.

Chang, M. et al., "The SMEM Seeding Acceleration for DNA Sequence Alignment", 2016 IEEE 24th Annual International Symposium on Filed-programmable Custom Computing Machines (FCCM), IEEE, CP032946099, May 2, 2016, 32-39.

Chang, X. et al., "Exploring Sequence Alignment Algorithms on FPGA-based Heterogeneous Architectures", IWBBIO, 2014, 330-341.

Chang, X. et al., "FPGA-based Heterogeneous Architecture for Sequence Alignment", 2014, 1-4.

Choi, Y. et al., "A Quantitative Analysis on Microarchitectures of modern CPU-FPGA platforms", Proceedings of the 53rd Annual Design Automation Conference ON, DAC '16, Jun. 5, 2016, 1-6.

Chrysanthou, N. et al., "Parallel Accelerators for GlimmerHMM Bioinformatics Algorithm", Technical University of Crete, 2011, 6 pages.

Derrien, et al., "Fast Computation and Applications of Genome Mappability", PLoS ONE 7(1), doi:10.1371/journal.pone.0030377, Jan. 19, 2012, e30377.

Deutsch, D. "Quantum theory, the Church-Turing principle and the universal quantum computer", Proceedings of the Royal Society of London, vol. A(400), 1985, 97-117.

Dydel, S. et al., "Large Scale Protein Sequence Alignment Using FPGA Reprogrammable Logic Devices", ECCV 2016 Conference, Springer International Publishing, Cham 032548; C. 3203, Aug. 30, 2004, 23-32.

Faes, P. et al., "Scalable Hardware Accelerator for Comparing DNA and Protein Sequences", Infoscale, 2006, 6 pages.

Fagin, B. et al., "FPGA and Rapid Prototyping Technology Use in a Special Purpose Computer for Molecular Genetics", Thayer School of Engineering, Dartmouth College, Jan. 11, 2017, 6 pages.

Fernandez, E. et al., "Exploration of Short Reads Genome Mapping in Hardware", Field Programmable Logic and Applications (FPL), Aug. 2010, 4 pages.

Fernandez, E. et al., "Multithreaded FPGA Acceleration of DNA Sequence Mapping", UC Riverside, Dept. of Computer Science and Engineering, 2012, 20 pages.

Fernandez, E. et al., "Multithreaded FPGA Acceleration of DNA Sequence Mapping", University of California, Riverside, 2012, 6 pages.

Ferraz, S. et al., "Evaluating Optimization Strategies for HMMer Acceleration on GPU", Federal University of Mato Grosso do Sul, Brazil, 2013, 59-68.

Feynman, R. "Simulating Physics with Computers", Department of Physics, California Institute of Technology, vol. 21(6/7), 1982, 467-488.

Guccione, S. et al., "Gene Matching Using JBits", Xilinx, Inc, 2002, 9 pages.

Guo, X et al., "A Systolic Array-Based FPGA Parallel Architecture for the BLAST Algorithm", ISRN Bioinformatics, vol. 2012, 2012, 11 pages.

Hall, A. "Short-Read DNA Sequence Alignment with Custom Designed FPGA-based Hardware", The University of Cambridge, 2007, 186 pages.

Hardcastle, T. et al., "baySeq: Empirical Bayesian methods for identifying differential expression in sequence count data", BMC Bioinformatics 11:422 http:l/bmcbioinformatics.biomedcentral.com/rticles/10.1186/1471-2105-11-422, Aug. 10, 2010, 1-16.

Harris, B. et al., "A Banded Amith-Waterman FPGA Accelerator for Mercury BLASTP", BECS Technology, Inc, 2007, 5 pages.

Hasan, L. et al., "An Overview of Hardware-Based Acceleration of Biological Sequence Alignment", www.intechopen.com, Sep. 2011, 187-202.

Herbordt, M. et al., "Single Pass Streaming BLAST on FPGAs", NIH Public Access Macuscript, vol. 33 (10-11), Nov. 2007, 741-756.

Herbordt, M. et al., "Single Pass, BLAST-like, Approximate String Matching on FPGAs", Boston University, vol. 2006, 2007, 19 pages.

Hoang, D. "A Systolic Array for the Sequence Alignment Problem", Department of Computer Science, Brown University, Apr. 1992, 25 pages.

Hoang, D. "FPGA Implementation of Systolic Sequence Alignment", Department of Computer Science Brown University, 1991, 4 pages.

(56) References Cited

OTHER PUBLICATIONS

Hoang, D. "Searching Genetic Databases on Splash 2", Department of Computer Science, Brown University, 1993, 185-191.
Homer, N. et al., "BFAST: An Alignment Tool for Large Scale Genome Resequencing", PLOS One http://journals.plos.org/plosone/article?id=10.1371/journal.pone.0007767, Nov. 11, 2009.
Huang, S. et al., "Hardware Acceleration of the Pair-HMM Algorithm for DNA Variant Calling", Advanced Digital Sciences Center, Feb. 2017, 275-284.
Hughey, R. "Parallel hardware for sequence comparison and alignment", Cabios, vol. 12 (6), 1996, 473-479.
Isa, N. et al., "A Novel Efficient FPGA Architecture for HMMER Acceleration", System Level Integration Group, School of Engineering, University of Edinburgh, 2013, 6 pages.
Isaac, TS et al., "160-fold acceleration of the Smith-Waterman algorithm using a field programmable gate array (FPGA)", BMC Bioinformatics, Jun. 7, 2007, 7 pages.
Jacob, A. et al., "FPGA-accelerated seed generation in Mercury BLASTP", Washington University in St. Louis; BECS Technology, Inc, 2007, 10 pages.
Jacob, A. et al., "Preliminary results in accelerating profile HMM search on FPGAs", Dept. of Computer Science and Engineering, Mar. 2007, 9 pages.
Junid, A. et al., "Development of Novel Data Compression Technique for Accelerate DNA Sequence Alignment Based on Smith-Waterman Algorithm", University Technology MARA (UiTM), vol. 978, 2009, 181-186.
Junid, A. et al., "Optimization of DNA Sequences Data for Accelerate DNA Sequences Alignment on FPGA", University Technology MARA (UiTM), vol. 978, 2010, 231-236.
Kasap, S. et al., "Design and Implementation of an FPGA-based Core for Gapped BLAST Sequence Alignment with the Two-Hit Method", Engineering Letters, vol. 16:3, Aug. 20, 2012, 10 pages.
Lancaster, J. et al., "Acceleration of Ungapped Extension in Mercury BLAST", MSP—7th Workshop on Media and Streaming Processors, Nov. 2005, 9 pages.
Lancaster, J. "Design and Evaluation of a BLAST Ungapped Extension Accelerator, Master's Thesis", Washington University, vol. 2006 (21), Jan. 1, 2006, 79 pages.
Langmead, B. et al., "Searching for SNPs with cloud computing", Genome Biology 10 (11) R134, Nov. 20, 2009.
Lavenier, D. "SAMBA: Systolic Accelerator for Molecular Biological Applications", INRIA Research Report, Mar. 1996, 22 pages.
Lemoine, E. et al., "High Speed Pattern Matching in Genetic Data Base with Reconfigurable Hardware", ISMB-94 Proceedings, 1994, 269-275.
Liu, Y. et al., "An FPGA-Based Web Serv er for High Performance Biological Sequence Alignment", NASA/ESA Conference on Adaptive Hardware and Systems, 2009, 361-368.
Lloyd, S. et al., "Hardware Accelerated Sequence Alignment with Traceback", Department of Computer Science, BYU, vol. 2009 (762362), 2009, 10 pages.
Lopresti, D. "Department of Computer Science", Department of Computer Science, Brown University, 1991, 138-152.
Madhavan, A. et al., "Race Logic: A Hardware Acceleration for Dynamic Programming Algorithms", University of California, Santa Barbara, 2014, 12 pages.
Mahram, A. "FPGA Acceleration of Sequence Analysis Tools in Bioinformatics", Boston University College of Engineering, 2013, 180 pages.
Maxfield, C. "Impulse achieves 16X speed-up of genome analysis on $2,500 FPGA module", EE Times http://www.eetimes.com/document.asp?doc_id=1317288&print=yes, Jun. 5, 2012, 1-4.
Mckenna, et al., "The Genome Analysis Toolkit: A MapReduce framework for analyzing next-generation DNA sequencing data", Genome Research, 20, 2010, 1297-1303.
Mikami, S. et al., "Efficient FPGA-based Hardware Algorithms for Approximate String Matching", The 23rd International Technical Conference on Circuits/Systems, Computers and Communications, 2008, 4 pages.
Miller, N. et al., "A 26-hour system of highly sensitive whole genome sequencing for emergency management of genetic diseases", Genome Medicine 7(100), Sep. 30, 2015, 1-16.
Moritz, G. et al., "Implementation of a Parallel Algorithm for Protein Pairwise Alignment Using Reconfigurable Computing", Bioinformatics Laboratory & Electronics Department, 2007, 7 pages.
Muriki, K. et al., "RC-BLAST: Towards a Portable, Cost-Effective Open Source Hardware Implementation", Supported in Part by the National Science Foundation, 2005, 8 pages.
Nawaz, Z. et al., "A Parallel FPGA design of the Smith-Waterman traceback", ACE Associated Compiler Expert, Jan. 6, 2011, 6 pages.
Nawaz, Z. et al., "Fast Smith-Waterman hardware implementation", Computer Engineering Lab, 2010, 4 pages.
Nelson, C. et al., "Shepard: A Fast Exact Match Short Read Aligner", Dept. of Electrical and Computer Engineering, 2012, 4 pages.
Oliver, T. et al., "Hyper Customized Processors for Bio-Sequence Database Scanning on FPGAs", Centre for Hign Performance Embedded Systems, Nanyang Technological University, 2005, 229-237.
Oliver, T. et al., "Multiple Sequence Alignment on an FPGA", Nanyang Technical University, 2005, 5 pages.
Oliver, T. et al., "Using reconfigurable hardware to accelerate multiple sequence alignment with ClustalW", Bioinformatics Applications Note, vol. 21 (16), 2005, 3431-3432.
Olson, C. "An FPGA Acceleration of Short Read Human Genome Mapping", University of Washington, 2011, 103 pages.
Olson, C. et al., "Hardware Acceleration of Short Read Mapping", University of Washington, 2012, 8 pages.
PCT/US17/58890, "International Search Report", dated Feb. 23, 2018.
PCT/US2014/12144, "International Search Report", dated Jun. 18, 2014.
PCT/US2016/020480, "International Search Report", dated May 17, 2016.
PCT/US2016/026796, "International Search Report", dated Jul. 18, 2016.
PCT/US2016/040842, "International Search Report", dated Oct. 4, 2016.
PCT/US2016/18765, "International Search Report", dated May 6, 2016.
PCT/US2017/013057, "International Search Report", dated Apr. 11, 2017.
PCT/US2017/036424, "International Search Report", dated Sep. 12, 2017.
Peltenburg, J. et al., "Maximizing Systolic Array Efficiency to Accelerate the PairHMM Forward Algorithm", IEEE International Conference on Bioinformatic and Biomedicine, 2016, 758-762.
Ren, S. et al., "FPGA Acceleration of the Pair-HMMs Forward Algorithm for DNA Sequence Analysis", IEEE, 2015, 6 pages.
Ruffalo, M. et al., "Comparative analysis of algorithms for next-generation sequencing read alignment", Bioinformatics 27(20), Aug. 19, 2011, 2790-2796.
Sarkar, S. et al., "Network-on-Chip Hardware Accelerators for Biological Sequence Alignment", IEEE Transactions on Computers, vol. 59 (1), Jan. 2010, 29-41.
Schatz, M. et al., "Cloud Computing and the DNA Data Race", Nat Biotechnol 28(7), Jul. 2010, 691-693.
Schatz, M. "CloudBurst: highly sensitive read mapping with MapReduce", Bioinformatics 25(11), Apr. 8, 2009, 1363-1369.
Schatz, M. et al., "High-throughput sequence alignment using Graphics Processing Units", BMC Bioinformatics http://bmcbioinformatics.biomedcentral.com/articles/10.1186/1471-2105-8-474, Dec. 10, 2007.

(56) References Cited

OTHER PUBLICATIONS

Settle, S. "High-performance Dynamic Programming on FPGAs with OpenCL", IEEE, 2013, 6 pages.
Sotiriades, E. et al., "FPGA based Architecture for DNA Sequence Comparison and Database Search", Technical University of Crete, vol. 1 (4244), 2006, 8 pages.
Sotiriades, E. et al., "Some Initial Results on Hardware BLAST Acceleration with a Reconfigurable Architecture", University of Crete, 2006, 8 pages.
Sun, Y. et al., "Accelerating HMMer on FPGAs Using Systolic Array Based Architecture", College of Computer Science and Technology, 2009, 8 pages.
Timelogic Division, "Accelerated BLAST Performance with Tera—BLAST™: a comparison of FPGA versus GPU and CPU BLAST implementations", Technical Note, vol. 1, May 2013, 5 pages.
Van Court, T. et al., "Families of FPGA-Based Algorithms for Approximate String Matching", Boston University, 2004, 11 pages.
Van Der Auwera, G. et al., "From FastQ data to high confidence variant calls: the Genome Analysis Toolkit best practices pipeline", Curr rotoc Bioinformatics 11(1110) 11.10.1-11.10.33, Oct. 15, 2013, 1-27.
Wu, T. et al., "GMAP: a genomic mapping and alignment program for mRNA and EST sequences", Bioinformatics, vol. 21(9), Feb. 22, 2005, 1859-1875.
Yamaguchi, Y. et al., "High Speed Homology Search with FPGAs", Pacific Symposium of Biocomputing, vol. 7, 2002, 271-282.
Yu, C.W. et al., "A Smith-Waterman Systolic Cell", The Chinese University of Hong Kong, 2003, 10 pages.
Zhang, W. et al., "A Practical Comparison of De Novo Genome Assembly Software Tools for Next-Generation Sequencing Technologies", PLoS ONE 6(3), Mar. 14, 2011, e17915.
Abbas, N., et al., "Combining Executin Pipelines to Improve Parallel Implementation of HMMER on FPGA", Microprocessors and Microsystems 39(7), Jun. 25, 2015, 457-470.
Derroen, S., et al., "Hardware Acceleration of HMMER on FPGAs", J Sign Process Syst 58, 2010, 53-67.
EP Extended European Search Report EP Appln. No. 19199685.9, dated Jan. 3, 2020, 13 pages.
Giraldo, J., et al., "A HMMER Hardware Accelerator using Divergences", 2010 Design, Automation & Test in Europe Conference and Exhibition, Mar. 12, 2010. 405-410.
Jiang, K., et al., "An Efficient Parallel Implementatio of the Hidden Markov Methods for Genomic Sequence Search on a Massively Parallel System", IEEE Transaction on Parallel and Distributed Systems 19(1), Jan. 2008, 1-9.

BIOINFORMATICS SYSTEMS, APPARATUSES, AND METHODS EXECUTED ON AN INTEGRATED CIRCUIT PROCESSING PLATFORM

CROSS REFERENCES TO RELATED APPLICATIONS

This application is a continuation of U.S. application Ser. No. 15/144,734 filed May 2, 2016, which is a continuation of U.S. application Ser. No. 14/948,372 filed on Nov. 22, 2015, now U.S. Pat. No. 9,342,652, which is a divisional of U.S. patent application Ser. No. 14/284,307, filed May 21, 2014, now U.S. Pat. No. 9,235,680, which is a continuation of U.S. patent application Ser. No. 14/279,063, filed May 15, 2014, now U.S. Pat. No. 9,679,104, which claims the benefit of U.S. Provisional Application Ser. No. 61/988,128 filed May 2, 2014, U.S. Provisional Application Ser. No. 61/984,663 filed Apr. 25, 2014, and U.S. Provisional Application Ser. No. 61/943,870 filed Feb. 24, 2014.

U.S. patent application Ser. No. 14/279,063 is also a continuation-in-part of U.S. patent application Ser. No. 14/158,758, filed Jan. 17, 2014, now U.S. Pat. No. 9,483,610, which claims the benefit of U.S. Provisional Application Ser. No. 61/910,868, filed Dec. 2, 2013, U.S. Provisional Application Ser. No. 61/823,824, filed May 15, 2013, U.S. Provisional Application Ser. No. 61/822,101, filed May 10, 2013, U.S. Provisional Application Ser. No. 61/826,381 filed May 22, 2013, and U.S. Provisional Application Ser. No. 61/753,775 field Jan. 17, 2013.

The disclosures of the above-identified patent applications are hereby incorporated by reference in their entirety.

STATEMENT REGARDING FEDERALLY SPONSORED RESEARCH OR DEVELOPMENT

Not Applicable

BACKGROUND OF THE INVENTION

Field of the Invention

The subject matter described herein relates to bioinformatics, and more particularly to systems, apparatuses, and methods for implementing bioinformatic protocols, such as performing one or more functions for analyzing genomic data on an integrated circuit, such as on a hardware processing platform.

Description of the Related Art

A goal for health care researchers and practitioners is to improve the safety, quality, and effectiveness of health care for every patient. Personalized health care is directed to achieving these goals on an individual level. For instance, "genomics" and/or "bioinformatics" are fields of study that aim to facilitate the safety, the quality, and the effectiveness of prophylactic and therapeutic treatments on a personalized, individual level. Accordingly, by employing genomics and/or bioinformatics techniques, the identity of an individual's genetic makeup, e.g., his or hers genes, may be determined and that knowledge may be used in the development of therapeutic and/or prophylactic regimens, including drug treatments, that are personalized to the individual, thus, enabling medicine to be tailored to meet each person's individual needs.

The desire to provide personalized care to individuals is transforming the health care system. This transformation of the health care system is likely to be powered by breakthrough innovations at the intersection of medical science and information technology such as is represented by the fields of genomics and bioinformatics. Accordingly, genomics and bioinformatics are key foundations upon which this future will be built. Science has evolved dramatically since the first human genome was fully sequenced in 2000 at a total cost of over $1 Billion. Today, we are on the verge of high resolution sequencing at a cost of less than $1K per genome, making it economically feasible for the first time to move out of the research lab and into widespread adoption for medical care. Genomic data, therefore, may become a vital input to diagnostic screening, therapeutic and/or prophylactic drug discovery, and/or disease treatment.

More particularly, genomics and bioinformatics are fields concerned with the application of information technology and computer science to the field of molecular biology. In particular, bioinformatics techniques can be applied to process and analyze various genomic data, such as from an individual so as to determine qualitative and quantitative information about that data that can then be used by various practitioners in the development of prophylactic and therapeutic methods for preventing or at least ameliorating diseased states, and thus, improving the safety, quality, and effectiveness of health care on an individualized level.

Because of its focus on advancing personalized healthcare, bioinformatics, therefore, promotes individualized healthcare that is proactive, instead of reactive, and this gives the patient the opportunity to become more involved in their own wellness. Typically, this can be achieved through two guiding principles. First, federal leadership can be provided to support research that addresses these individual aspects of disease and disease prevention, such as with the ultimate goal of shaping diagnostic and preventative care to match each person's unique genetic characteristics. Additionally, a "network of networks" may be created to aggregate health care data to help researchers establish patterns and identify genetic "definitions" to existing diseases.

An advantage of employing bioinformatics technologies in such instances is that the qualitative and/or quantitative analyses of molecular biological data can be performed on a broader range of sample sets at a much higher rate of speed and often times more accurately, thus expediting the emergence of a personalized healthcare system.

Accordingly, in various instances, the molecular data to be processed in a bioinformatics based platform typically concerns genomic data, such as Deoxyribonucleic acid (DNA) data. For example, a well-known method for generating DNA data involves DNA sequencing. DNA sequencing can be performed manually, such as in a lab, or may be performed by an automated sequencer, such as at a core sequencing facility, for the purpose of determining the genetic makeup of a sample of an individual's DNA. The person's genetic information may then be used in comparison to a referent, e.g., a reference genome, so as to determine its variance therefrom. Such variant information may then be subjected to further processing and used to determine or predict the occurrence of a diseased state in the individual.

For instance, manual or automated DNA sequencing may be employed to determine the sequence of nucleotide bases in a sample of DNA, such as a sample obtained from a subject. Using various different bioinformatics techniques these sequences may then be assembled together to generate the genomic sequence of the subject, and/or mapped and aligned to genomic positions relative to a reference genome. This sequence may then be compared to a reference genomic sequence to determine how the genomic sequence of the subject varies from that of the reference. Such a process involves determining the variants in the sampled sequence and presents a central challenge to bioinformatics methodologies.

For example, a central challenge in DNA sequencing is assembling full-length genomic sequences, e.g., chromosomal sequences, from a sample of genetic material and/or mapping and aligning sample sequence fragments to a reference genome, yielding sequence data in a format that can be compared to a reference genomic sequence such as to determine the variants in the sampled full-length genomic sequences. In particular, the methods employed in sequencing protocols do not produce full-length chromosomal sequences of the sample DNA.

Rather, sequence fragments, typically from 100-1,000 nucleotides in length, are produced without any indication as to where in the genome they align. Therefore, in order to generate full length chromosomal genomic constructs, or determine variants with respect to a reference genomic sequence, these fragments of DNA sequences need to be mapped, aligned, merged, and/or compared to a reference genomic sequence. Through such processes the variants of the sample genomic sequences from the reference genomic sequences may be determined.

However, as the human genome is comprised of approximately 3.1 billion base pairs, and as each sequence fragment is typically only from 100 to 500 to 1,000 nucleotides in length, the time and effort that goes into building such full length genomic sequences and determining the variants therein is quite extensive often requiring the use of several different computer resources applying several different algorithms over prolonged periods of time.

In a particular instance, thousands to millions of fragments or even billions of DNA sequences are generated, aligned, and merged in order to construct a genomic sequence that approximates a chromosome in length. A step in this process may include comparing the DNA fragments to a reference sequence to determine where in the genome the fragments align.

A number of such steps are involved in building chromosome length sequences and in determining the variants of the sampled sequence. Accordingly, a wide variety of methods have been developed for performing these steps. For instance, there exist commonly used software implementations for performing one or a series of such steps in a bioinformatics system. However, a common characteristic of such software based bioinformatics methods and systems is that they are labor intensive, take a long time to execute on general purpose processors, and are prone to errors.

A bioinformatics system, therefore, that could perform the algorithms implemented by such software in a less labor and/or processing intensive manner with a greater percentage accuracy would be useful. However, even as we approach the "$1000 Genome", the cost of analyzing, storing and sharing this raw digital data has far outpaced the cost of producing it. This data analysis bottleneck is a key obstacle standing between these ever-growing raw data and the real medical insight we seek from it.

Accordingly, presented herein are systems, apparatuses, and methods for implementing a genomics and/or bioinformatic protocols, such as for performing one or more functions for analyzing genomic data, for instance, on an integrated circuit, such as on a hardware processing platform. For example, as set forth herein below, in various implementations, a hardware accelerator, such as an integrated circuit, may be employed in performing such bioinformatics related tasks where the integrated circuit may be formed of one or more hardwired digital logic circuits, which may be interconnected by a plurality of physical electrical interconnects, that can be arranged as a set of processing engines, wherein each processing engine is capable of being configured to perform one or more steps in a bioinformatics genetic analysis protocol. An advantage of this arrangement is that the bioinformatics related tasks may be performed in a manner that is faster than the software typically engaged for performing such tasks. Such hardware accelerator technology, however, is currently not typically employed in the genomics and/or bioinformatics space.

BRIEF SUMMARY OF THE INVENTION

This present disclosure is related to performing a task such as in a bioinformatics protocol. In various instances, a plurality of tasks are performed, and in some instances these tasks are performed in a manner so as to form a pipeline, wherein each task and/or its substantial completion acts as a building block for each subsequent task until a desired end result is achieved. Accordingly, in various embodiments, the present disclosure is directed to performing one or more methods on one or more apparatuses wherein the apparatus has been optimized for performing those methods. In certain embodiments, the one or more methods and/or one or more apparatuses are formulated into one or more systems.

For instance, in certain aspects, the present disclosure is directed to systems, apparatuses, and methods for implementing genomics and/or bioinformatic protocols such as, in various instances, for performing one or more functions for analyzing genetic data on an integrated circuit, such as implemented in a hardware processing platform. For example, in one aspect, a bioinformatics system is provided. The system may involve the performance of various bioanalytical functions that have been optimized so as to be performed faster and/or with increased accuracy. The methods for performing these functions may be implemented in software or hardware solutions. Accordingly, in certain instances, methods are presented where the method involves the performance of an algorithm where the algorithm has been optimized in accordance with the manner in which it is to be implemented. In particular, where the algorithm is to be implemented in a software solution, the algorithm and/or its attendant processes, has been optimized so as to be performed faster and/or with better accuracy for execution by that media. Likewise, where the functions of algorithm are to be implemented in a hardware solution, the hardware has been designed to perform these functions and/or their attendant processes in an optimized manner so as to be performed faster and/or with better accuracy for execution by that media.

Accordingly, in one aspect, presented herein are systems, apparatuses, and methods for implementing bioinformatic protocols, such as for performing one or more functions for analyzing genetic data, for instance, via one or more optimized algorithms and/or on one or more optimized integrated circuits, such as on one or more hardware processing platforms. Hence, in one instance, methods are provided for implementing one or more algorithms for the performance of one or more steps for analyzing genomic data in a bioinformatics protocol. In another instance, methods are provided for implementing the functions of one or more algorithms for the performance of one or more steps for analyzing genomic data in a bioinformatics protocol, wherein the functions are implemented on an integrated circuit formed of one or more hardwired digital logic circuits. In such an instance, the hardwired digital logic circuits may be interconnected, such as by one or a plurality of physical electrical interconnects, and may be arranged to function as one or more processing engines. In various instances, a plurality of hardwired digital logic circuits are provided, which hardwired digital logic circuits are configured as a set of processing engines, wherein each processing engine is capable of performing one or more steps in a bioinformatics genetic analysis protocol.

More particularly, in one instance, a system for executing a sequence analysis pipeline such as on genetic sequence data is provided. The system may include one or more of an electronic data source, a memory, and an integrated circuit. For instance, in one embodiment, an electronic data source is included, where in the electronic data source may be configured for providing one or more digital signals, such as a digital signal representing one or more reads of genetic data, for example, where each read of genomic data includes a sequence of nucleotides. Further, the memory may be configured for storing one or more genetic reference sequences, and may further be configured for storing an index, such as an index of the one or more genetic reference sequences.

Further still, the integrated circuit may be formed of a set of hardwired digital logic circuits such as where the hardwired digital logic circuits are interconnected, e.g., by a plurality of physical electrical interconnects. In various instances, one or more of the plurality of physical electrical interconnects may include an input, such as to the integrated circuit, and may further be connected with the electronic data source, so as to be able to receive the one or more reads of genomic data. In various embodiments, the hardwired digital logic circuits may be arranged as a set of processing engines, such as where each processing engine is formed of a subset of the hardwired digital logic circuits, and is configured so as to perform one or more steps in the sequence analysis pipeline, such as on the plurality of reads of genomic data. In such instances, each subset of the hardwired digital logic circuits may be in a wired configuration so as to perform the one or more steps in the sequence analysis pipeline.

Accordingly, in various instances, a plurality of hardwired digital logic circuits are provided wherein the hardwired digital logic circuits are arranged as a set of processing engines, wherein one or more of the processing engines may include one or more of a mapping module and/or an alignment module and/or a sorting module. For instance, in various embodiments, the one or more of the processing engines may include a mapping module, which mapping module may be in a wired configuration and further be configured for accessing the index of the one or more genetic reference sequences from the memory, such as by one or more of the plurality of physical electronic interconnects, for example, so as to map the plurality of reads to one or more segments of the one or more genetic reference sequences.

Additionally, in various embodiments, the one or more of the processing engines may include an alignment module, which alignment module may be in the wired configuration and may be configured for accessing the one or more genetic reference sequences from the memory, such as by one or more of the plurality of physical electronic interconnects, for example, so as to align the plurality of reads to the one or more segments of the one or more genetic reference sequences. Further, in various embodiments, the one or more of the processing engines may include a sorting module, which sorting module may be in the wired configuration and may be configured for accessing the one or more aligned reads from the memory, such as by one or more of the plurality of physical electronic interconnects, for example, so as to sort each aligned read, such as according to its one or more positions in the one or more genetic reference sequences. In such instances, the one or more of the plurality of physical electrical interconnects may include an output from the integrated circuit, such as for communicating result data from the mapping module and/or the alignment module and/or the sorting module.

In various instances, the integrated circuit may include a master controller so as to establish the wired configuration for each subset of the hardwired digital logic circuits, for instance, for performing the one or more of mapping, aligning, and/or sorting, which functions may be configured as one or steps in a sequence analysis pipeline. Further, in various embodiments, the integrated circuit may be configured as a field programmable gate array (FPGA) having hardwired digital logic circuits, such as where the wired configuration may be established upon manufacture of the integrated circuit, and thus may be non-volatile. In other various embodiments, the integrated circuit may be configured as an application specific integrated circuit (ASIC) having hardwired digital logic circuits. In other various embodiments, the integrated circuit may be configured as a structured application specific integrated circuit (Structured ASIC) having hardwired digital logic circuits.

In certain instances, the integrated circuit and/or the memory may be housed on an expansion card, such as a peripheral component interconnect (PCI) card, for instance, in various embodiments, the integrated circuit may be a chip having a PCIe card. In various instances, the integrated circuit and/or chip may be a component within a sequencer, such as an automated sequencer, and/or in other embodiments, the integrated circuit and/or expansion card may be accessible via the internet, e.g., cloud. Further, in some instances, the memory may be a volatile random access memory (RAM).

Accordingly, in one aspect, an apparatus for executing one or more steps of a sequence analysis pipeline, such as on genetic data, is provided wherein the genetic data includes one or more of a genetic reference sequence(s), an index of the one or more genetic reference sequence(s), and/or a plurality of reads, such as of genetic data. In various instances, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects. In certain instances, the one or more of the plurality of physical electrical interconnects may include an input, such as for receiving the plurality of reads of genomic data. Additionally, the set of hardwired digital logic circuits may further be in a wired configuration, so as to access the index of the one or more genetic reference sequences, via one of the plurality of physical electrical interconnects, and to map the plurality of reads to one or more segments of the one or more genetic reference sequences, such as according to the index.

In various embodiments, the index may include one or more hash tables, such as a primary and/or secondary hash table. For instance, a primary hash table may be included, wherein in such an instance, the set of hardwired digital logic circuits may be configured to do one or more of: extracting one or more seeds of genetic data from the plurality of reads of genetic data; executing a primary hash function, such as on the one or more seeds of genetic data so as to generate a lookup address for each of the one or more seeds; and accessing the primary hash table using the lookup address so as to provide a location in the one or more genetic reference sequences for each of the one or more seeds of genetic data. In various instances, the one or more seeds of genetic data may have a fixed number of nucleotides.

Further, in various embodiments, the index may include a secondary hash table, such as where the set of hardwired digital logic circuits is configured for at least one of extending at least one of the one or more seeds with additional neighboring nucleotides, so as to produce at least one extended seed of genetic data; executing a hash function, e.g., a secondary hash function, on the at least one extended seed of genetic data, so as to generate a second lookup address for the at least one extended seed; and accessing the secondary hash table, e.g., using the second lookup address, so as to provide a location in the one or more genetic reference sequences for each of the at least one extended seed of genetic data. In various instances, the secondary hash function may be executed by the set of hardwired digital logic circuits, such as when the primary hash table returns an extend record instructing the set of hardwired digital logic circuits to extend the at least one of the one or more seeds with the additional neighboring nucleotides. In certain instances, the extend record may specify the number of additional neighboring nucleotides by which the at least one or more seeds is extended, and/or the manner in which the seed is to be extended, e.g., equally by an even number of "x" nucleotides to each end of the seed.

Additionally, in one aspect, an apparatus for executing one or more steps of a sequence analysis pipeline on genetic sequence data is provided, wherein the genetic sequence data includes one or more of one or a plurality of genetic reference sequences, an index of the one or more genetic reference sequences, and a plurality of reads of genomic data. In various instances, the apparatus may include an integrated circuit, which integrated circuit may include one or more, e.g., a set, of hardwired digital logic circuits, wherein the set of hardwired digital logic circuits may be interconnected, such as by one or a plurality of physical electrical interconnects. In certain instances, the one or more of the plurality of physical electrical interconnects may include an input, such as for receiving the plurality of reads of genomic data. Additionally, the set of hardwired digital logic circuits may further be in a wired configuration, so as to access the one or more genetic reference sequences, via one of the plurality of physical electrical interconnects, to receive location information specifying one or more segments of the one or more reference sequences, and to align the plurality of reads to the one or more segments of the one or more genetic reference sequences.

In various instances, the wired configuration of the set of hardwired digital logic circuits, are configured to align the plurality of reads to the one or more segments of the one or more genetic reference sequences, and further include a wave front processor that me be formed of the wired configuration of the set of hardwired digital logic circuits. In certain embodiments, the wave front processor may be configured to process an array of cells of an alignment matrix, such as a matrix defined by a subset of the set of hardwired digital logic circuits. For instance, in certain instances, the alignment matrix may define a first axis, e.g., representing one of the plurality of reads, and a second axis, e.g., representing one of the segments of the one or more genetic reference sequences. In such an instance, the wave front processor may be configured to generate a wave front pattern of cells that extend across the array of cells from the first axis to the second axis; and may further be configured to generate a score, such as for each cell in the wave front pattern of cells, which score may represent the degree of matching of the one of the plurality of reads and the one of the segments of the one or more genetic reference sequences.

In such an instance, the wave front processor may further be configured so as to steer the wave front pattern of cells over the alignment matrix such that the highest score may be centered on the wave front pattern of cells. Additionally, in various embodiments, the wave front processor may further be configured to backtrace one or more, e.g., all, the positions in the scored wave front pattern of cells through previous positions in the alignment matrix; track one or more, e.g., all, of the backtraced paths until a convergence is generated; and generate a CIGAR string based on the backtrace from the convergence.

In certain embodiments, the wired configuration of the set of hardwired digital logic circuits to align the plurality of reads to the one or more segments of the one or more genetic reference sequences may include a wired configuration to implement a Smith-Waterman and/or Burrows-Wheeler scoring algorithm. In such an instance, the Smith-Waterman and/or Burrows-Wheeler scoring algorithm may be configured to implement a scoring parameter that is sensitive to base quality scores. Further, in certain embodiments, the Smith-Waterman scoring algorithm may be an affine Smith-Waterman scoring algorithm.

Accordingly, in one aspect, a method for executing a sequence analysis pipeline such as on genetic sequence data is provided. The genetic data may include one or more genetic reference sequences, one or more indexes of the one or more genetic reference sequences, and/or a plurality of reads of genomic data. The method may include one or more of receiving, accessing, mapping, aligning, and/or sorting various iterations of the genetic sequence data. For instance, in certain embodiments, the method may include receiving, on an input to an integrated circuit from an electronic data source, one or more of a plurality of reads of genomic data, wherein each read of genomic data may include a sequence of nucleotides. In such an instance, the integrated circuit may be formed of a set of hardwired digital logic circuits such as are interconnected by a plurality of physical electrical interconnects, which physical electrical interconnects may include one or more of the plurality of physical electrical interconnects comprising the input.

The method may further include accessing, by the integrated circuit on one or more of the plurality of physical electrical interconnects from a memory, the index of the one or more genetic reference sequences. In such an instance the method may include mapping, by a first subset of the hardwired digital logic circuits of the integrated circuit, the plurality of reads to one or more segments of the one or more genetic reference sequences. Additionally, the method may include accessing, by the integrated circuit on one or more of the plurality of physical electrical interconnects from the memory, the one or more genetic reference sequences; and aligning, by a second subset of the hardwired digital logic circuits of the integrated circuit, the plurality of reads to the one or more segments of the one or more genetic reference sequences.

In various embodiments, the method may additionally include accessing, by the integrated circuit on one or more of the plurality of physical electrical interconnects from a memory, the aligned plurality of reads. In such an instance the method may include sorting, by a third subset of the hardwired digital logic circuits of the integrated circuit, the aligned plurality of reads according to their positions in the one or more genetic reference sequences. In certain instances, the method may further include outputting, such as on one or more of the plurality of physical electrical interconnects of the integrated circuit, result data from the mapping and/or the aligning and/or the sorting, such as where the result data includes positions of the mapped and/or aligned and/or sorted plurality of reads.

Hence, in various instances, implementations of various aspects of the disclosure may include, but are not limited to: apparatuses, systems, and methods including one or more features as described in detail herein, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. Accordingly, computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc. A memory, which can include a computer-readable storage medium, may include, encode, store, or the like one or more programs that cause one or more processors to perform one or more of the operations described herein.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
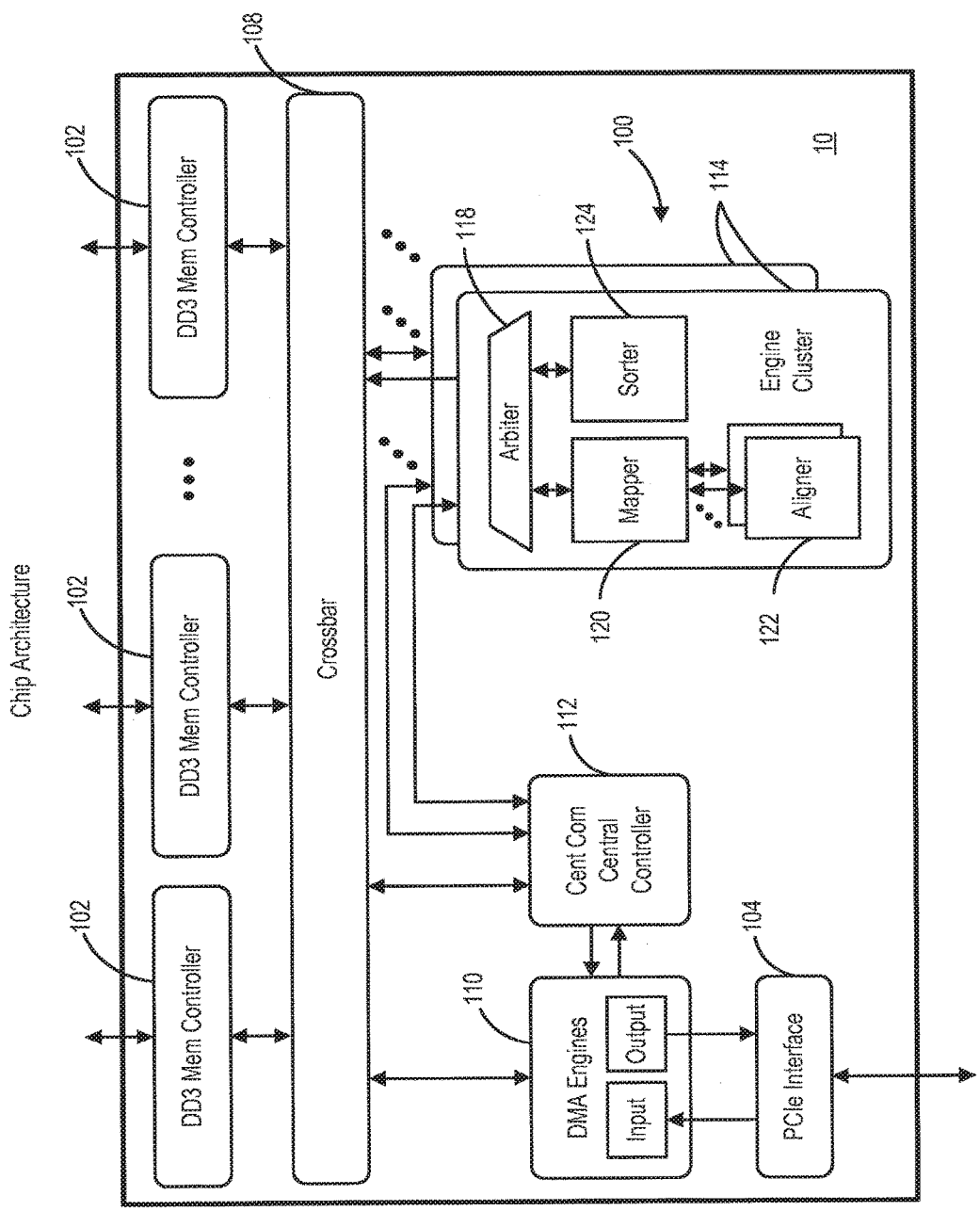
FIG. 1 is a block diagram of a hardware processor architecture in accordance with an implementation.

To address these and potentially other issues with currently available solutions, methods, systems, articles of manufacture, and the like consistent with one or more implementations of the current subject matter can, among other possible advantages, provide a sequence analysis apparatus for executing a sequence analysis pipeline on genetic sequence data.

The following provides details of various implementations of a sequence analysis pipeline and platform.

In its most basic form, the body is comprised of cells, the cells form tissues, tissues form organs, organs form systems, and these systems function together to ensure the body operates to sustain the life of the individual. The cells of the body, therefore, are the building blocks of life. More particularly, each cell has a nucleus, and within the nucleus of every cell reside chromosomes. Chromosomes are formed from Deoxyribonucleic Acid, which has an organized but winding double helix structure. The DNA itself is comprised of two opposed, but complementary strands of nucleotides, which nucleotides comprise the genes that code for the proteins that give the cells their structures and mediate the functions and regulations of the body's tissues and organs. Basically, proteins do most of the work of cells in maintaining the body's normal processes and functions.

Given the multiplicity of components of the body and the complexity involved in how they interact with one another to maintain the body's various processes and functions, there are a multiplicity of ways that the body may malfunction on any one of these different levels. For instance, in one such instance, there may be a malfunction in the way a particular gene codes for a given protein, which dependent on the protein and the nature of its malfunctioning can result in the onset of a diseased state.

Accordingly, in diagnosing, preventing, and/or curing such diseased states, determining the genetic makeup of a subject may be extremely useful. For instance, once known, a person's genetic makeup, e.g., his or her genomic composition, can be used for purposes of diagnostics and/or for determining whether a person has or has the potential for a diseased state. Likewise, the knowledge of a person's genome may be useful in determining various potential therapeutic modalities, such as drugs, that can or cannot be used in a prophylactic or therapeutic regimen without causing harm to the user. In various instances, knowledge of a person's genome may also be employed to determine drug efficacy and/or problematic side effects of such drug use may be predicted and/or identified. Potentially, the knowledge of a person's genome can be used to produce designer drugs, such as drugs tailor made and optimized in accordance with a person's specific genetic makeup. In particular, in one instance, an engineered protein or nucleotide sequence can be fabricated to an individual's unique genetic characteristics so as to turn off or turn on the transcription of genes that either over or under produce proteins and thereby ameliorate diseased states.

Hence, in some instances, it is a goal of bioinformatics processing to determine individual genomes of people, which determinations may be used in gene discovery protocols as well as for prophylaxis and/or therapeutic regimes to better enhance the livelihood of each particular person and human kind as a whole. Further, knowledge of an individual's genome may be used such as in drug discovery and/or FDA trials to better predict with particularity which, if any, drugs will be likely to work on an individual and/or which would be likely to have deleterious side effects, such as by analyzing the individual's genome and/or a protein profile derived therefrom and comparing the same with predicted biological response from such drug administration.

Such bioinformatics processing usually involves three well defined, but typically separate phases of information processing. The first phase involves DNA sequencing, where a subject's DNA is obtained and subjected to various processes whereby the subject's genetic code is converted to a machine-readable digital code, e.g., a FASTQ file. The second phase involves using the subject's generated digital genetic code for the determination of the individual's genetic makeup, e.g., determining the individual's genomic nucleotide sequence. And the third phase involves performing one or more analyses on the subject's genetic makeup so as to determine therapeutically useful information therefrom.

Preliminarily to Phase I, or primary processing, the genetic material must be preprocessed, so as to derive usable genetic sequence data. This preprocessing may be done manually or via an automated sequencer. Typically, preprocessing involves obtaining a biological sample from a subject, such as through venipuncture, hair, etc. and treating the sample to isolate the DNA therefrom. Once isolated the DNA may be denatured, strand separated, and/or portions of the DNA may then be multiplied, e.g., via polymerase chain reaction (PCR), so as to build a library of replicated strands that are now ready to be read, such as by an automated sequencer, which sequencer is configured to read the replicate strands, e.g., by synthesis, and thereby determine the nucleotide sequences that makes up the DNA. Further, in various instances, such as in building the library of replicated strands, it may be useful to provide for over-coverage when preprocessing a given portion of the DNA. To perform this over-coverage, e.g., using PCR, may require increased sample preparation resources and time, and therefore be more expensive, but it often gives an enhanced probability of the end result being more accurate.

Once the library of replicated strands has been generated they may be injected into an automated sequencer that may then read the strands, such as by synthesis, so as to determine the nucleotide sequences thereof. For instance, the replicated single stranded DNA may be attached to a glass bead and inserted into a test vessel, e.g., an array. All the necessary components for replicating its complementary strand, including labeled nucleotides, are also added to the vessel but in a sequential fashion. For example, all labeled "A", "C", "G", and "T's" are added, either one at a time or all together to see which of the nucleotides is going to bind at position one. After each addition a light, e.g., a laser, is shone on the array. If the composition fluoresces then an image is produced indicating which nucleotide bound to the subject location. More particularly, where the nucleotides are added one at a time, if a binding event occurs, then its indicative fluorescence will be observed. If a binding event does not occur, the test vessel may be washed and the procedure repeated until the appropriate one of the four nucleotides binds to its complement at the subject location, and its indicative fluorescence is observed. Where all four nucleotides are added at the same time, each may be labeled with a different fluorescent indicator, and the nucleotide that binds to its complement at the subject position may be determined, such as by the color of its fluorescence. This greatly accelerates the synthesis process.

Once a binding event has occurred, the complex is then washed and the synthesis steps are repeated for position two. For example, a marked nucleotide "A" may be added to the mix to determine if the complement at position one is an "A", and if so, all the sequences having that complement will bind to the labeled "A" and will therefore fluoresce, and the samples will all be washed. Where the binding happened the bound nucleotide is not washed away, and then this will be repeated for all nucleotides for all positions until all the oversampled nucleic acid segments, e.g., reads, have been sequenced and the data collected. Alternatively, where all four nucleotides are added at the same time, each labeled with a different fluorescent indicator, only one nucleotide will bind to its complement at the subject position, and the others will be washed away, such that after the vessel has been washed, a laser may be shone on the vessel and which nucleotide bound to its complement may be determined, such as by the color of its fluorescence.

This continues until the entire strand has been replicated in the vessel. Usually a typical length of a sequence replicated in this manner is from about 100 to about 500 base pairs, such as between 150 to about 400 base pairs, including from about 200 to about 350 base pairs, such as about 250 base pairs to about 300 base pairs dependent on the sequencing protocol being employed. Further, the length of these segments may be predetermined, e.g., engineered, to accord with any particular sequencing machinery and/or protocol by which it is run. The end result is a readout, or read, that is comprised of a replicated DNA segment, e.g., from about 100 to about 1,000 nucleotides in length, that has been labeled in such a manner that every nucleotide in the sequence, e.g., read, is known because of its label. Hence, since the human genome is comprised of about 3.2 billion base pairs, and various known sequencing protocols usually result in labeled replicated sequences, e.g., reads, from about 100 or 101 bases to about 250 or about 300 or about 400 bases, the total amount of segments that need to be sequenced, and consequently the total number of reads generated, can be anywhere from about 10,000,000 to about 40,000,000, such as about 15,000,000 to about 30,000,000, dependent on how long the label replicated sequences are. Therefore, the sequencer may typically generate about 30,000,000 reads, such as where the read length is 100 nucleotides in length, so as to cover the genome once.

However, as indicated above, in such procedures, it may be useful to oversample the DNA such by about 5×, or about 10×, or about 20×, or about 25×, or about 30×, or about 40×, or about 50×, or about 100×, or about 200×, or about 250×, or about 500×, or about 1,000×, or about 5,000×, or even about 10,000× or more, and as such the amount of primary processing needed to be done and the time taken to do this can be quite extensive. For instance, with 40× oversampling, wherein the various synthesized reads are designed to overlap to some extent, up to about 1.2 billion reads may need to be synthesized. Typically, a large majority if not all of these labeled sequences can be generated in parallel. The end result is that the initial biological genetic material is processed, e.g., by sequencing protocols such as those summarized herein, and a digital representation of that data is generated, which digital representation of data may be subjected to a primary processing protocol. Particularly, the genetic material of a subject may be replicated and sequenced in such a manner that a measurable electrical, radioactive and/or optical signal is generated, which signal is then converted, e.g., by the sequencer, into a digital representation of the subject's genetic code. More particularly, primary processing may include the conversion of images, such as recorded flashes of light or other electrical signal data, into FASTQ file data. Accordingly, this information is stored as a FASTQ file, which may then be sent for further, e.g., secondary processing. A typical FASTQ file includes a large collection of reads representing digitally encoded nucleotide sequences wherein each predicted base in the sequence has been called and given a probability score that the called base at the indicated position is incorrect.

In many instances, it may be useful to further process the digitally encoded sequence data obtained from the sequencer and/or sequencing protocol, such as by subjecting the digitally represented data to secondary processing. This secondary processing, for instance, can be used to assemble an entire genomic profile of an individual, such as where the individual's entire genetic makeup is determined, for instance, where each and every nucleotide of each and every chromosome is determined in sequential order such that the composition of the individual's entire genome has been identified. In such processing, the genome of the individual may be assembled such as by comparison to a reference genome, such as a standard, e.g., one or more genomes obtained from the human genome project, so as to determine how the individual's genetic makeup differs from that of the referent(s), e.g., reference genomes. This process is commonly known as variant calling. As the difference between the DNA of any one person to another is 1 in 1,000 base pairs, such a variant calling process can be very labor and time intensive.

Accordingly, in a typical secondary processing protocol, a subject's genetic makeup is assembled by comparison to a reference genome. This comparison involves the reconstruction of the individual's genome from millions upon millions of short read sequences and/or the comparison of the whole of the individual's DNA to an exemplary DNA sequence model. In a typical secondary processing protocol a FASTQ file is received from the sequencer containing the raw sequenced read data. For instance, in certain instances, there can be up to 30,000,000 reads or more covering the subject's genome, assuming no oversampling, such as where each read is about 100 nucleotides in length. Hence, in such an instance, in order to compare the subject's genome to that of the standard reference genome, it needs to be determined where each of these reads map to the reference genome, such as how each is aligned with respect to one another, and/or how each read can also be sorted by chromosome order so as to determine at what position and in which chromosome each read belongs. One or more of these functions may take place prior to performing a variant call function on the entire full-length sequence. Once it is determined where in the genome each read belongs, the full length genetic sequence may be determined, and then the differences between the subject's genetic code and that of the referent can be assessed.

As the human genome is over 3 billion base pairs in length, efficient automated sequencing protocols and machinery have been developed so as to effectuate the sequencing of such a genome within a time period that could be clinically useful. Such innovations in automated sequencing have resulted in the capabilities of sequencing an entire genome in a matter of hours to days dependent on the number of genomes being sequenced, the amount of oversampling involved, and the number of processing resources being dedicated to the job. Hence, given these advancements in sequencing, a large amount of sequencing data is capable of being generated in a relatively short period of time. A result of these advancements, however, is the development of a bottleneck at the secondary processing stage. In efforts to help overcome this bottleneck various software based algorithms have been developed to help expedite the process of assembling a subject's sequenced DNA such as by a reference based assembly process.

For instance, reference based assembly is a typical secondary processing assembly protocol involving the comparison of sequenced genomic DNA of a subject to that of one or more standards, e.g., known reference sequences. Various algorithms have been developed to help expedite this process. These algorithms typically include some variation of one or more of: mapping, aligning, and/or sorting the millions of reads received from the FASTQ file communicated by the sequencer, to determine where on each chromosome each particular read is located. Often a common feature behind the functioning of these various algorithms is their use of an index and/or an array to expedite their processing function.

For instance, with respect to mapping, a large quantity, e.g., all, of the sequenced reads may be processed to determine the possible locations in the reference genome to which those reads could possibly align. One methodology that can be used for this purpose is to do a direct comparison of the read to the reference genome so as to find all the positions of matching. Another methodology is to employ a prefix or suffix array, or to build out a prefix or suffix tree, for the purpose of mapping the reads to various positions in the reference genome. A typical algorithm useful in performing such a function is a Burrows-Wheeler transform, which is used to map a selection of reads to a reference using a compression formula that compresses repeating sequences of data. A further methodology is to employ a hash table, such as where a selected subset of the reads, a k-mer of a selected length "k", e.g., a seed, are placed in a hash table as keys and the reference sequence is broken into equivalent k-mer portions and those portions and their location are inserted by an algorithm into the hash table at those locations in the table to which they map according to a hashing function. A typical algorithm for performing this function is "BLAST", a Basic Local Alignment Search Tool. Such hash table based programs compare query nucleotide or protein sequences to one or more standard reference sequence databases and calculates the statistical significance of matches. In such manners as these, it may be determined where any given read is possibly located with respect to a reference genome. These algorithms are useful because they require less memory, fewer look ups, and therefore require fewer processing resources and time in the performance of their functions, than would otherwise be the case, such as if the subject's genome were being assembled by direct comparison, such as without the use of these algorithms.

Additionally, an aligning function may be performed to determine out of all the possible locations a given read may map to on a genome, such as in those instances where a read may map to multiple positions in the genome, which is in fact the location to which it actually was derived, such as by being sequenced therefrom by the original sequencing protocol. This function may be performed on a number of the reads of the genome and a string of ordered nucleotide bases representing a portion or the entire genetic sequence of the subject's DNA may be obtained. Along with the ordered genetic sequence a score may be given for each nucleotide position, representing the likelihood that for any given nucleotide position, the nucleotide, e.g., "A", "C", "G", "T" (or "U"), predicted to be in that position is in fact the nucleotide that belongs in that assigned position. Typical algorithms for performing alignment functions are Needleman-Wunsch and Smith-Waterman. In either case, these algorithms perform sequence alignments between a string of the subject's query genomic sequence and a string of the reference genomic sequence whereby instead of comparing the entire genomic sequences, one with the other, segments of a selection of possible lengths are compared.

Once the reads have been assigned a position, such as relative to the reference genome, which may include identifying to which chromosome the read belongs and/or its offset from the beginning of that chromosome, the reads may be sorted by position. This may enable downstream analyses to take advantage of the oversampling described above. All of the reads that overlap a given position in the genome will be adjacent to each other after sorting and they can be organized into a pileup and readily examined to determine if the majority of them agree with the reference value or not. If they do not, a variant can be flagged.

Although these algorithms and the others like them go a ways to resolving the bottlenecks inherent in secondary processing, faster performance time and better accuracy are still desirable. More particularly, although there has been advancement in the generation of raw data, such as sequence data, the advancements in information technologies have not kept up pace, leading to a data analysis bottleneck. This bottleneck is somewhat lessened by the development of various algorithms, such as those described above, which help accelerate these analyses, but there still exists a need for new technologies to handle the computation, storage, and/or analysis of such data, especially as it relates to genomic sequence analysis, such as in a secondary processing stage.

For instance, employing standard protocols for performing secondary processing on obtained genomic sequencing data, can take up to three (3) days or even up to a week or more to process the sequenced data so as to generate clinically relevant genomic sequence information of an individual. Employing various different optimized algorithms, such as those described above, the time expended for secondary processing can be brought down to a mere 27 to 48 hours. However, in order to achieve such rapid results typically requires virtually all the generated reads, e.g., 30 million reads of 100 nucleotides each, to be processed in parallel and at the same time. Such parallel processing requires extensive processing power involving massive CPU resources and still takes a relatively long time.

Further, in various instances, enhanced accuracy of results is desired. Such enhanced accuracy can be achieved through providing some amount of oversampling of the sequenced genome. For example, as described above, it may be desirable to process the subject's DNA in such a manner that at any given location of a sequence of nucleotides, there is an oversampling of that region. As indicated above, it may be desired to oversample any given region of the genome up to 10×, or 15×, or 20×, or 25×, or 30×, or 40×, 50×, 100×, 250× or even 500× or 1,000× or more. However, where the genome is oversampled, such as by 40×, the amount of reads to be processed is roughly 30 Million×40 (dependent on the length of the reads), which amounts to about 1.2 billion reads that need to be processed, when the entire genome is oversampled by 40×. Hence, although such oversampling typically results in greater accuracy, it is at a cost of taking more time and requiring more extensive processing resources as each section of the genome is covered by anywhere from 1 to 40 times. Moreover, for certain oncology applications in which a clinician is trying to distinguish between the mutated genome of cancer cells in the blood stream as distinct from the genome of healthy cells, oversampling of as much as 500×, or 1,000×, or 5,000×, or even 10,000× may be employed.

The present disclosure, therefore, is directed to such new technologies that may be implemented in one or a series of genomics and/or bioinformatics protocols for performing genetic analysis, such as secondary processing, on obtained genomic sequencing data or a portion thereof. The sequencing data may be obtained directly from an automated high throughput sequencer system, such as by a "Sequencing by Synthesis" 454 automated sequencer from ROCHE, a HiSeqxTen or a Solexia automated sequencer from ILLUMINA, a "Sequencing by Oligonucleotide Ligation and Detection" (SOLiD) or Ion Torrent sequencer by LIFE TECHNOLOGIES, and/or a "Single Molecule Fluorescent Sequencing" sequencer by HELICOS GENETIC ANALYSIS SYSTEMS, or the like, such as by a direct linkage with the sequencing processing unit, or the sequencing data may be obtained remotely, such as from a database, for instance, accessible via the internet or other remote location accessible through a wireless communications protocol, such as Wi-Fi, Bluetooth, or the like.

In certain aspects, these genetic analysis technologies may employ improved algorithms that may be implemented by software that is run in a less processing intensive and/or less time consuming manner and/or with greater percentage accuracy. For instance, in certain embodiments, improved algorithms for performing such secondary processing, as disclosed herein, is provided. In various particular embodiments, the improved algorithms are directed to more efficiently and/or more accurately performing one or more of mapping, aligning, and/or sorting functions, such as on a digital representation of DNA sequence data obtained from a sequencing platform, such as in a FASTQ file format obtained from an automated sequencer such as one of those set forth above.

In certain embodiments, improved algorithms directed to more efficiently and/or more accurately performing one or more of local realignment, duplicate marking, base quality score recalibration, variant calling, compression, and/or decompression functions are provided. Further, as described in greater detail herein below, in certain aspects, these genetic analysis technologies may employ on or more algorithms, such as improved algorithms, that may be implemented by hardware that is run in a less processing intensive and/or less time consuming manner and/or with greater percentage accuracy than various software implementations for doing the same.

In particular embodiments, a platform of technologies for performing genetic analyses are provided where the platform may include the performance of one or more of: mapping, aligning, sorting, local realignment, duplicate marking, base quality score recalibration, variant calling, compression, and/or decompression functions. In certain instances, the implementation of one or more of these platform functions is for the purpose of performing one or more of determining and/or reconstructing a subject's consensus genomic sequence, comparing a subject's genomic sequence to a referent sequence, e.g., a reference or model genetic sequence, determining the manner in which the subject's genomic DNA differs from the reference sequence, e.g., variant calling, and/or for performing a tertiary analysis on the subject's genomic sequence, such as for genome-wide variation analysis, gene function analysis, protein function analysis, e.g., protein binding analysis, quantitative and/or assembly analysis of genomes and/or transcriptomes, as well as for various diagnostic, and/or a prophylactic and/or therapeutic evaluation analyses.

Further, in various embodiments, a bioinformatics processing regime, as disclosed herein, may be employed for the purpose of creating one or more masks, such as a genome reference mask, a default mask, a disease mask, and/or an iterative feed back mask, which may be added to the mapper and/or aligner, e.g., along with a reference, wherein the mask set is configured so as to identify a particular area or object of interest. For instance, in one embodiment, the methods and apparatuses described herein may be employed so as to create genome reference mask, such as by creating a mask-set that can be loaded into the mapper and/or aligner along with a reference, wherein the mask set is configured so as to identify areas of high importance and/or relevance, e.g., to the practitioner or subject, and/or so as to identify areas having increased susceptibility to errors. In various embodiments, the mask-set may provide intelligent guidance to the mapper and/or aligner such as on which areas of the genome to focus on to improve quality. Masks, therefore, can be created in a layered manner to provide varying levels or iterations of guidance based on various specific applications. Each mask accordingly could identify the areas of interest and provide a minimum quality target for the area. Additionally, a default mask may be employed to provide guidance, such as on an identified, e.g., typical, "high value" areas of the genome. Such areas could include known coding areas, control areas, etc. as well as areas that are well known to produce errors. Further, a disease mask, or application specific mask, may be employed to the mask-set that identifies areas of high importance, such as areas that require very high levels of accuracy based on known markers, e.g., Cancer. Further still, iterative feedback masking may be employed, such as by adding a new, ad-hoc mask, that may be specifically designed by using feedback from a tertiary analysis system (like Cypher Genomics) that has identified areas of concern based on observed errors or inconsistencies.

As indicated above, in one aspect one or more of these platform functions, e.g., mapping, aligning, sorting, realignment, duplicate marking, base quality score recalibration, variant calling, compression, and/or decompression functions is configured for implementation in software. In another embodiment, one or more of these platform functions, e.g., mapping, aligning, sorting, local realignment, duplicate marking, base quality score recalibration, decompression, variant calling, compression, and/or decompression functions is configured for implementation in hardware.

Accordingly, in certain instances, methods are presented herein where the method involves the performance of an algorithm, such as an algorithm for performing one or more genetic analysis functions such as mapping, aligning, sorting, realignment, duplicate marking, base quality score recalibration, variant calling, compression, and/or decompression where the algorithm has been optimized in accordance with the manner in which it is to be implemented. In particular, where the algorithm is to be implemented in a software solution, the algorithm and/or its attendant processes, has been optimized so as to be performed faster and/or with better accuracy for execution by that media. Likewise, where the functions of the algorithm are to be implemented in a hardware solution, the hardware has been designed to perform these functions and/or their attendant processes in an optimized manner so as to be performed faster and/or with better accuracy for execution by that media. These methods, for instance, can be employed such as in an iterative variant calling procedure.

Hence, in one aspect, presented herein are systems, apparatuses, and methods for implementing bioinformatic protocols, such as for performing one or more functions for analyzing genetic data, such as genomic data, for instance, via one or more optimized algorithms and/or on one or more optimized integrated circuits, such as on one or more hardware processing platforms. Hence, in one instance, systems and methods are provided for implementing one or more algorithms for the performance of one or more steps for analyzing genomic data in a bioinformatics protocol, such as where the steps may include the performance of one or more of: mapping, aligning, sorting, local realignment, duplicate marking, base quality score recalibration, variant calling, compression, and/or decompression. In another instance, systems and methods are provided for implementing the functions of one or more algorithms for the performance of one or more steps for analyzing genomic data in a bioinformatics protocol, as set forth herein, wherein the functions are implemented on a hardware accelerator, which may or may not be coupled with one or more general purpose processors and/or super computers.

More specifically, in some instances, methods for performing secondary analytics on data pertaining to the genetic composition of a subject are provided. In one instance, the analytics to be performed may involve reference based reconstruction of the subject genome. For instance, referenced based mapping involves the use of a reference genome, which may be generated from sequencing the genome of a single or multiple individuals, or it may be an amalgamation of various people's DNA that have been combined in such a manner so as to produce a prototypical, standard reference genome to which any individual's DNA may be compared, for example, so as to determine and reconstruct the individual's genetic sequence and/or for determining the difference between their genetic makeup and that of the standard reference, e.g., variant calling.

More particularly, a reason for performing a secondary analysis on a subject's sequenced DNA is to determine how the subject's DNA varies from that of the reference. More specifically, to determine one, a multiplicity, or all the differences in the nucleotide sequence of the subject from that of the reference. For instance, the differences between the genetic sequences of any two random persons is 1 in 1,000 base pairs, which when taken in view of the entire genome of over 3 billion base pairs amounts to a variation of up to 3,000,000 divergent base pairs per person. Determining these differences may be useful such as in a tertiary analysis protocol, for instance, so as to predict the potential for the occurrence of a diseased state, such as because of a genetic abnormality, and/or the likelihood of success of a prophylactic or therapeutic modality, such as based on how a prophylactic or therapeutic is expected to interact with the subject's DNA or the proteins generated therefrom. In various instances, it may be useful to perform both a de novo and a reference based reconstruction of the subject's genome so as to confirm the results of one against the other, and to, where desirable, enhance the accuracy of a variant calling protocol.

In various instances, as set forth above, it may be useful in performing a primary sequencing protocol to produce oversampling for one or more regions of the subject's genome. These regions may be selected based on known areas of increased variability, suspected regions of variability, such as based on the condition of the subject, and/or on the entire genome generally. In its basic form, as indicated above, based on the type of sequencing protocols performed, sequencing produces readouts, e.g., reads, that are digital representations of the subject's genetic sequence code. These read lengths are typically designed based on the type of sequencing machinery being employed. For instance, the 454 automated sequencer from ROCHE, typically produces read lengths from 100 or 150 base pairs in length to about 1,000 base pairs; for ILLUMINA the read lengths are typically engineered to be from about 100 or 101 to about 150 base pairs in length for some of their technology, and 250 base pairs in length for other of their technology; for LIFE TECHNOLOGIES the read lengths are typically engineered to be from about 50 to about 60 base pairs in length for their SOLiD technology and from 35 to 450 base pairs in length for their Ion Torrent technology; and for the HELICOS GENETIC ANALYSIS SYSTEMS the read lengths may vary but may typically be less than 1,000 nucleotides in length.

However, because the processing of the DNA sample required to produce engineered read lengths of a specific size is both labor and chemistry intensive, and because the sequencing itself often depends on the functioning of the sequencing machinery, there is some possibility that errors may be made throughout the sequencing process thereby introducing an abnormality into that portion of the sequenced genome where the error occurred. Such errors can be problematic especially where a purpose for reconstructing the subject's genome is to determine how it or at least a portion of the genome varies from a standard or model reference. For instance, a machine or chemistry error resulting in the change of one nucleotide, e.g., in a read, for another will give a false indication of a variation that is not really there. This can result in an incorrect variant call and may further result in the false indication of a diseased state and the like. Accordingly, because of the possibility of machine, chemistry, and/or even human error in the execution of a sequencing protocol, in many instances, it is desirable to build redundancy into an analysis system, such as by oversampling portions of or the entire genome. More particularly, as an automated sequencer produces a FASTQ file calling out a sequence of reads having nucleotides at a given position along with the probability that the call for a given nucleotide being at the called position is actually incorrect, e.g., a base call, it is often desirable to employ methods, such as oversampling, for ensuring that base calls made by the sequencing processes can be detected and corrected.

Hence, in performing the methods herein described, in certain instances, a primary sequencing protocol is performed in such a manner so as to produce a sequenced genome where a portion or the entire genome is oversampled by about 10×, about 15×, about 20×, about 25×, about 30×, about 40×, such as about 50× or more. Accordingly, where the read lengths are engineered to be about 50-60 base pairs in length, this oversampling can result in about 2 to about 2.5 billion reads, or where the read lengths are about 100 or 101 base pairs in length, oversampling may result in about 1 to about 1.2 billion reads, and where the read lengths are about 1,000 base pairs in length, about 50 to about 100 million reads may be generated by the sequencer, such as where the oversampling is about 40×. More particularly, in such an instance, because of the 40× oversampling, at any given point in the genome it is expected that there will be 40 reads to cover any one position albeit, the given position might be at the beginning of one read, the middle of another, and the end of another, but it is expected to be covered about 40×.

Therefore, such oversampling produces regions of the sequenced genome that are covered by a multiplicity of reads, e.g., duplications, such as up to about 40 reads, for instance, where the oversampling is about 40×. These at least partial duplications are useful in determining whether any given variation in any particular read is in fact an actual genomic variation or rather a machine or chemistry artifact. Hence, oversampling can be employed to improve the accuracy in reconstructing the subject's genome, especially in instances where the subject's genome is to be compared against a reference genome so as to determine those instances where the subject's genetic sequence differs from that of the reference genetic sequence. In a manner such as this, as described in greater detail herein below, it can be confirmed that any given variation between the reconstructed sequence and the model is in fact due to the presence of an actual variant and not an error in the initial processing of sample DNA, or read alignment software, etc.

For instance, in building the genetic sequence of the individual's sequenced DNA, it must be determined what nucleotide goes where in the growing string of nucleotides. In order to determine what nucleotide goes where, the various reads can be organized and a pile up of reads covering duplicate locations can be built up. This allows for a comparison to be made of all the reads covering the same locations so as to more accurately determine if there is an actual variation at any given position or if there may be an error in any one read at the position in question in the pileup. For example, if there is only one or two of the reads out of the 40 that has a particular nucleotide at position X, and all 38 or 39 other reads agree on a different nucleotide being at that position, then the two outlying reads may be excluded as being in error, at least at this specific location.

More particularly, where there are a multiplicity of reads generated for any one location of the subject's genome, there are likely to be multiple overlaps or pile-ups for any given nucleotide position. These pile-ups represent the coverage for any particular location and may be useful for determining with better accuracy the correct sequence of the subject's genome. For instance, as indicated, sequencing results in the production of reads, and in various instances, the reads produced are over sampled, and so at various positions various particular reads will overlap. This overlapping is useful for determining the actual sample genome such as with a high probability of correctness.

The purpose, therefore, may be to scan over the reference genome incrementally multiple times, as described in greater detail herein below, so as to more accurately reconstruct the subject's genome, and where it is desirable to determine how the subject's genome differs from a different genome, e.g., a model genome, the use of pile-ups can more accurately identify errors, such as chemical, machine, or read errors, and distinguish them from actual variants. More specifically, where the subject has an actual variation at position X, the majority of reads in the pile up should verify, e.g., include, that variation. Statistical analysis procedures, such as those described herein, may then performed to determine the actual genetic sequence of the subject with all its variants from a reference genome.

For instance, where the subject's genetic sequence is to be rebuilt with respect to the use of a reference genome, once the reads, e.g., a pile-up of reads, have been generated, the next steps may be to map and/or align and/or sort the reads to one or more reference genomes (e.g., the more exemplary reference genomes available as models the better the analysis is likely to be) and thereby rebuild the genome of the subject, this results in a series of reads that have been mapped and/or aligned with the reference genome(s) at all possible positions along the chain where there is a match, and at each such position they are given a probability score as to the probability that they actually belong in that position.

Accordingly, in various instances, once the reads have been generated, their positions mapped, e.g., the potential locations in the reference genome to which the reads may map have been determined, and their sequential order aligned, the actual genetic sequence of the subject's genome may be determined, such as by performing a sorting function on the aligned data. Further, once the actual sample genome is known and compared to the reference genome, the variations between the two can be determined, a list of all the variations/deviations between the reference genome and the sample genome are determined and called out. Such variations between the two genetic sequences may be due to a number of reasons.

For instance, there may be a single nucleotide polymorphism (SNP), such as wherein one base in the subject's genetic sequence has been substituted for another; there may be more extensive substitutions of a plurality of nucleotides; there may be an insertion or a deletion, such as where one or a multiplicity of bases have been added to or deleted from the subject's genetic sequence, and/or there may be a structural variant, e.g., such as caused by the crossing of legs of two chromosomes, and/or there may simply be an offset causing a shift in the sequence. In various instances, a variant call file containing all the variations of the subject's genetic sequence to the reference sequence is generated. More particularly, in various embodiments, the methods of the disclosure include generating a variant call file (VCF) identifying one or more, e.g., all of the genetic variants in the individual whose DNA was sequenced, e.g., relevant to one or more reference genomes. The VCF in its basic form is a list of locations of variants and their type: e.g., chromosome 3, at position X, an "A" is substituted for a "T", etc.

However, as indicated above, in order to generate such a file, the genome of the subject must be sequenced and rebuilt prior to determining its variants. There are, however, several problems that may occur when attempting to generate such an assembly. As noted above, there may be problems with the chemistry, the sequencing machine, and/or human error that occurs in the sequencing process. Additionally, there may be genetic artifacts that make such reconstructions problematic. For instance, a problem with performing such assemblies is that there are sometimes huge portions of the genome that repeat themselves, such as long sections of the genome that include the same strings of nucleotides. Hence, because any genetic sequence is not unique everywhere, it may be difficult to determine where in the genome an identified read actually maps and aligns.

For instance, dependent on the sequencing protocol employed shorter or longer reads may be produced. Longer reads are useful in that the longer the read the less likely it is to show up in multiple locations in the genome. Having fewer possible locations to evaluate can also speed up the system. However, the longer the reads the more problematic they may be because the more likely they are to include a real or false variation, e.g., caused by an SNP, InDel (insertion or deletion), or a machine error, or the like, resulting in a no match between the read and the reference genome. On the other hand, shorter reads are useful because the shorter the read the less likely it is to cover a position that codes for a variant. A problem with shorter reads however is that the shorter the read the more likely it is to show up at multiple positions in the genome, thus requiring additional processing time and resources so as to determine which out of all possible positions is the most likely actual position to where it aligns. Ideally what may be achieved, such as by practicing the methods herein disclosed, is that a variant call file may be produced wherein a list of the sequenced genome (the query sequence) is generated that shows where all the variant base pairs are, making sure each variant called is an actual variant and not simply a chemistry or machine read or other human based error.

There are, therefore, two main possibilities for variation. For one, there is an actual variation at the particular location in question, for instance, where the person's genome is in fact different at a particular location than that of the reference, e.g., there is a natural variation due to an SNP (one base substitution), an Insertion or Deletion (of one or more nucleotides in length), and/or there is a structural variant, such as where the DNA material from one chromosome gets crossed onto a different chromosome or leg, or where a certain region gets copied twice in the DNA. Alternatively, a variation may be caused by there being a problem in the read data, either through chemistry or the machine, sequencer or aligner, or other human error. Accordingly, the methods disclosed herein may be employed in a manner so as to compensate for these types of errors, and more particularly so as to distinguish errors in variation due to chemistry, machine or human, and real variations in the sequenced genome. More specifically, the methods, apparatuses, and systems for employing the same, as here in described, have been developed so as to clearly distinguish between these two different types of variations and therefore to better ensure the accuracy of any call files generated so as to correctly identify true variants.

Further, in various embodiments, once the subject's genome has been reconstructed and/or a VCF has been generated, such data may then be subjected to tertiary processing so as to interpret it, such as for determining what the data means with respect to identifying what diseases this person may or may have the potential for suffer from and/or for determining what treatments or lifestyle changes this subject may want to employ so as to ameliorate and/or prevent a diseased state. For example, the subject's genetic sequence and/or their variant call file may be analyzed to determine clinically relevant genetic markers that indicate the existence or potential for a diseased state and/or the efficacy of a proposed therapeutic or prophylactic regimen may have on the subject. This data may then be used to provide the subject with one or more therapeutic or prophylactic regimens so as to better the subject's quality of life, such as treating and/or preventing a diseased state.

More particularly, medical science technologies have advanced in conjunction with the advancement of information technologies, which advancement has enhanced our ability to store and analyze medical data. Hence, once one or more of an individual's genetic variations are determined, such variant call file information can be used to develop medically useful information, which in turn can be used to determine, e.g., using various known statistical analysis models, health related data and/or medical useful information, e.g., for diagnostic purposes, e.g., diagnosing a disease or potential therefore, clinical interpretation (e.g., looking for markers that represent a disease variant), whether the subject should be included or excluded in various clinical trials, and other such purposes. As there are a finite number of diseased states that are caused by genetic malformations, in tertiary processing variants of a certain type, e.g., those known to be related to the onset of diseased states, can be queried for, such as by determining if one or more genetic based diseased markers are included in the variant call file of the subject.

Consequently, in various instances, the methods herein disclosed may involve analyzing, e.g., scanning, the VCF and/or the generated sequence, against a known disease sequence variant, such as in a data base of genomic markers therefore, so as to identify the presence of the genetic marker in the VCF and/or the generated sequence, and if present to make a call as to the presence or potential for a genetically induced diseased state. As there are a large number of known genetic variations and a large number of individual's suffering from diseases caused by such variations, in some embodiments, the methods disclosed herein may entail the generation of one or more databases linking sequenced data for an entire genome and/or a variant call file pertaining thereto, e.g., such as from an individual or a plurality of individuals, and a diseased state and/or searching the generated databases to determine if a particular subject has a genetic composition that would predispose them to having such diseased state. Such searching may involve a comparison of one entire genome with one or more others, or a fragment of a genome, such as a fragment containing only the variations, to one or more fragments of one or more other genomes such as in a database of reference genomes or fragments thereof.

Further, it is understood that the genetic sequences to be employed in these manners may be DNA, ssDNA, RNA, mRNA, rRNA, tRNA, or the like. Hence, although throughout the present disclosure various mention is made to various methods and apparatuses for analyzing genomic DNA, in various instances, the systems, apparatuses and methods disclosed herein are equally suitable for performing their respective functions, e.g., analysis, on all types of genetic material including DNA, ssDNA, RNA, mRNA, rRNA, tRNA, and the like. Additionally, in various instances, the methods of the disclosure may include analyzing the generated genetic sequence, e.g., DNA, ssDNA, RNA, mRNA, rRNA, tRNA, and the like, from the subject and determining therefrom the protein variations which are likely to be caused by the genetic sequence and/or determining and/or predicting the potential for a diseased state therefrom, such as due to an error in protein expression. It is to be noted that the genetic sequence obtained can represent an intron or an exon, for instance, the genetic sequence can be for a coding portion of the DNA only, such as where an exome is obtained and using known processing techniques only the coding regions, or non-coding regions, may be sequenced, which can lead to faster sequencing and/or faster processing times, albeit involving a more difficult sample preparation procedure.

Currently, such steps and analyses herein described are typically performed in various distinct and unrelated steps often employing different analytic machines at different locations. Accordingly, in various aspects the methods and systems of the disclosure are performed by a single apparatus and/or at one location, such as in conjunction with an automated sequencer or other apparatus configured to generate genetic sequence data. In various instances, a plurality of apparatuses may be employed at the same location, or a multiplicity of remote locations, and in some instances, the methods may involve two or more processing units being deployed at two or more locations.

For instance, in various aspects a pipeline may be provided wherein the pipeline includes performing one or more analytic functions, as described herein, on a genomic genetic sequence of one or more individuals, such as data obtained in a digital, e.g., FASTQ, file format from an automated sequencer. A typical pipeline to be executed may include one or more of sequencing genetic material, such as a portion or an entire genome, of one or more subjects, which genetic material may include DNA, ssDNA, RNA, rRNA, tRNA, and the like, and/or in some instances the genetic material may represent coding or non-coding regions, such as exomes, episomes of the DNA. The pipeline may include one or more of performing a base calling and/or error correction operation, such as on the digitized genetic data, and/or may include one or more of performing a mapping, an alignment, and/or a sorting function on the genetic data. In certain instances, the pipeline may include performing one or more of a realignment, a deduplication, a base quality or score recalibration, a reduction and/or compression, and/or a decompression on the digitized genetic data. In certain instances the pipeline may include performing a variant calling operation on the genetic data.

Therefore, in various instances, a pipeline of the disclosure may include one or more modules, wherein the modules are configured for performing one or more functions, such as a base calling and/or error correction operation and/or a mapping and/or an alignment and/or a sorting function on genetic data, e.g., sequenced genetic data. And in various instances, the pipeline may include one or more modules, wherein the modules are configured for performing one more of a local realignment, a deduplication, a base quality score recalibration, a variant calling, a reduction and/or compression, and/or a decompression on the genetic data. Many of these modules may either be performed by software or on hardware or remotely, e.g., via software or hardware, such as on the cloud or a remote server and/or server bank.

Additionally, many of these steps and/or modules of the pipeline are optional and/or can be arranged in any logical order and/or omitted entirely. For instance, the software and/or hardware disclosed herein may or may not include a base calling or sequence correction algorithm, such as where there may be concern that such functions may result in a statistical bias. Consequently the system will either include or will not include the base calling and/or sequence correction function, respectively, dependent on the level of accuracy and/or efficiency desired. And as indicated above, one or more of the pipeline functions may be employed in the generation of a genomic sequence of a subject such as through a reference based genomic reconstruction. Also as indicated above, in certain instances, the output from the pipeline is a variant call file indicating a portion or all the variants in a genome or a portion thereof.

Accordingly, as indicated above, the output of performing a sequencing protocol, such as one or more of those set forth above, is typically a digital representation of the subject's genetic material, such as in a FASTQ file format. However, an autorad that has been digitally transcribed may also be employed. More particularly, the output from a sequencing protocol may include a plurality of reads, where each read includes a sequence, e.g., a string, of nucleotides where the position of every nucleotide has been called, and a quality score representing the probability that the called nucleotide is wrong. However, the quality of these outputs may be improved by various pre-processing protocols so as to achieve higher quality of scores, which one or more of such protocols may be employed in the methods disclosed herein.

For instance, in certain instances, the raw FASTQ file data may be processed to clean up the initial base calls obtained from the sequencer/reader, such as in a primary processing stage, e.g., prior to the secondary processing described herein above. Specifically, the sequencer/reader typically analyzes the sequencing data, such as the fluorescent data indicating which nucleotide is at what position, and converts the image data into a base call with a quality score, such as where the quality score is based on the comparative brightness of the fluorescence at each position. A specialized algorithm may be employed, such as in a primary processing stage, to correctly analyze these distinctions in fluorescence so as to more accurately make the appropriate base call. As indicated above, this step may be included in a pipeline of steps and may be implemented via software or hardware or both, however, in this instance would be part of a primary processing platform.

An additional preprocessing step may include an error correction function, which may include an attempt to take the millions to billions of reads in the FASTQ file and correct some proportion of any mechanical sequencing error with the information pertaining to the base call and quality score available prior to any further processing such as mapping, alignment, and/or sorting functions, etc. For instance, the reads within the FASTQ file may be analyzed to determine if there are any sub-sequences in any of the reads that appear in other reads, which because of the duplicate coverage can increase confidence that the subsequences in the reads may be correct. This may be implemented by building a hash table containing all possible k-mers of a selected length, k, from every read, and storing with each one its frequency and also which bases immediately follow it and with what probability. Then, using the hash table each read can be rescanned. As each k-mer in a particular read is looked up in the hash table, and evaluation can be made as to whether the base immediately following that k-mer is likely to be correct or not. If it is unlikely, then it can be replaced with the most likely one to follow from the table. Subsequent k-mers for that read will then include the corrected base as the value at that position and the process is repeated. This can be highly effective in correcting errors because oversampling enables gathering accurate statistics for predicting what comes next after each k-mer. However, as indicated above, such corrections could add statistical biasing to the system, such as due to false corrections, to the data, and so these procedures can be skipped if desired.

Accordingly, in accordance with the aspects of the disclosure, in various instances, the methods, apparatuses, and/or systems of the disclosure, may include obtaining read data, that either have or have not been preprocessed, such as by being obtained directly from a FASTQ file of an automated sequencer, and subjecting the obtained data to one or more of a mapping, aligning, and/or sorting function. The performance of such functions may be useful, for instance, because, as set forth above, in various instances, the sequencing data typically generated by various automated sequencers, e.g., reads, have lengths that are substantially shorter than the entire genomic sequence being analyzed, and since the human genome typically has a multiplicity of repetitive sections, and is known to have various repeating patterns in it, there may be therefore a multiplicity of locations that any given read sequence may correspond to a segment in the human genome. Consequently, given all the possibilities a given read may match to the sequence of the genome, such as because of various repeating sequences in the genome, etc. the raw read data may not clearly indicate which one of the possibilities is in fact the correct location from which it was derived. Hence, for each read it will need to be determined to where in the genome the reads actually map. Additionally, it may also be useful to determine the sequential alignment of the reads, so as to determine the actual sequence identity of the subject, and/or it may also be useful to determine the chromosomal location for each portion of the sequence.

Accordingly, in various instances, the methods of the disclosure may be directed to mapping, aligning, and/or sorting the raw read data of the FASTQ files so as to find all the likely places that a given read may be aligned, and/or to determine the actual sequence identify of a subject, and/or to determine the chromosome location for each portion of the sequence. For example, mapping may be employed so as to map the generated reads to the reference genome and thereby find the location where each read appears to match well to the genome, e.g., finding all the places where there might be a good score for aligning any given read to the reference genome. Mapping therefore may involve taking one or more, e.g., all, of the raw or preprocessed reads received from the FASTQ file and comparing the reads with one or more reference genomes and determining where the read may match with the reference genome(s). In its basic from, mapping involves finding the location(s) in the reference genome where one or more of the FASTQ reads obtained from the sequencer appears to match.

Likewise, alignment may be employed so as to evaluate all the candidate locations of the individual reads against a window of the reference genome to determine where and how the read sequences best align to the genome. However, performing an alignment may be difficult due to substitutions, insertions, deletions, structural variations, and the like which may prevent the read from aligning exactly. There are, therefore, several different ways to get an alignment, but to do so may require making changes in the read, where each change that needs to be made to get the appropriate alignment results in a lower confidence score. For instance, any given read may have substitutions, insertions, and/or deletions as compared to the reference genome, and these variations need to be accounted for in performing an alignment.

Accordingly, along with the predicted alignment a probability score that the predicted alignment is correct may also be given. This score indicates the best alignment for any given read amongst multiple locations where that read may align. For example, the alignment score is predicated upon how well a given read matches a potential map location and may include stretching, condensing, and changing bits and pieces of the read so as to get the best alignment.

The score will reflect all the ways the read was changed so as to accommodate the reference. For instance, in order to generate an alignment between the read and the reference one or more gaps in the read may need to be inserted, wherein the insertion of each gap represents a deletion in the read over the reference. Likewise, deletions may need to be made in the read, wherein each deletion represents an insertion in the read over the reference. Additionally, various bases may need to be changed such as due to one or more substitutions. Each of these changes are made to make the read(s) more exactly align to the reference, but each change comes with a cost to the quality score, which score is a measure as to how well the entire read matches to some region of the reference. The confidence in such quality scores is then determined by looking at all the locations the read can be made to map to the genome and comparing the scores at each location, and choosing the one with the highest score. More particularly, where there are multiple positions with high quality scores, then confidence is low, but where the difference between the first and second best scores is large, then confidence is high. At the end, all the proposed reads and confidence scores are evaluated and the best fit is selected.

Once the reads are assigned a position relative to the reference genome, which consists of identifying to which chromosome the read belongs and its offset from the beginning of that chromosome, they may be sorted, such as by position. This enables downstream analyses to take advantage of the various oversampling protocols described herein. All of the reads that overlap a given position in the genome maybe be adjacent to each other after sorting and they can be piled up and readily examined to determine if the majority of them agree with the reference value or not. If they do not, as indicated above, a variant can be flagged.

As indicated above, the FASTQ file obtained from the sequencer is comprised of a plurality, e.g., millions to a billion or more, of reads consisting of short strings of nucleotide sequence data representing a portion or the entire genome of an individual. Mapping, in general, involves plotting the reads to all the locations in the reference genome to where there is a match. For example, dependent on the size of the read there may be one or a plurality of locations where the read substantially matches a corresponding sequence on the reference genome. Accordingly, the mapping and/or other functions disclosed herein may be configured for determining where out of all the possible locations one or more reads may match to in the reference genome is actually the true location to where they map.

It is possible to compare every read with every position in the 3.2 billion reference genome to determine where, if any, the reads match to the reference genome. This may be done, for instance, where the read lengths approach about 100,000 nucleotides, about 200,000 nucleotides, about 400,000 nucleotides, about 500,000 nucleotides, even about 1,000,000 or more nucleotides in length. However, where the reads are substantially shorter in length, such as where there are 50 million reads or more, e.g., 1 billion reads, this process could take a very long time and require a large amount of computing resources. Accordingly, there are several methods, such as described herein, that have been developed for aligning the FASTQ reads to the reference genome in a much quicker manner. For instance, as disclosed above, one or more algorithms may be employed so as to map one or more of the reads generated by the sequencer, e.g., in a FASTQ file, and match them to the reference genome, so as to determine where in the reference genome the subject reads potentially map.

For instance, in various methods, an index of the reference is generated, so that the reads or portions of the reads may be looked up in the index, retrieving indications of locations in the reference, so as to map the reads to the reference. Such an index of the reference can be constructed in various forms and queried in various manners. In some methods, the index may include a prefix and/or a suffix tree. In other various methods, the index may include a Burrows/Wheeler transform of the reference. In further methods, the index may include one or more hash tables, and a hash function may be performed on one or more portions of the reads in an effort to map the reads to the reference. In various instances, one or more of these algorithms may be performed sequentially or at the same time so as to accurately determine where one or more, e.g., a substantial portion or every, read correctly matches with the reference genome.

Each of these algorithms may have advantages and/or disadvantages. For example, a prefix and/or suffix Tree and/or a Burrows/Wheeler transformation may be performed on the sequence data in such a manner that the index of the reference genome is constructed and/or queried as a tree-like data structure, where starting from a single-base or short subsequence of a read, the subsequence is incrementally extended within the read, each incremental extension stimulating accesses to the index, tracing a path through the tree-like data structure, until the subsequence becomes unique enough, e.g., an optimal length has been attained, and/or a leaf node is reached in the tree-like data structure, the leaf or last-accessed tree node indicating one or more positions in the reference genome from which the read may have originated. These algorithms, therefore, typically do not have a fixed length for the read subsequences that may be mapped by querying the index. A hash function, however, often employs a fixed length comparison unit that may be the entire length of the read, but is often times a length that is some sub-portion thereof, which sub-portion is termed a seed. Such seeds can be shorter or longer, but unlike with the prefix and/or suffix trees and/or the Burrows/Wheeler transformations, the seeds of the reads employed in a hash function are typically of a preselected, fixed length.

A prefix and/or suffix tree is a data structure that is built up from the reference genome, such that each link from a parent node to a child node is labeled or associated with a nucleotide or sequence of nucleotides, and each path from a root node through various links and nodes traces a path whose associated aggregate nucleotide sequence matches some continuous subsequence of the reference genome. The node reached by such a path is implicitly associated with the reference subsequence traced by its path from the root. Proceeding from the root node, subsequences in a prefix tree grow forward in the reference genome, whereas subsequences in a suffix tree grow backward in the reference genome. Both a prefix tree and a suffix tree may be used in a hybrid prefix/suffix algorithm, so that subsequences may grow in either direction. Prefix and suffix trees may also contain additional links, such as jumping from a node associated with one reference subsequence to another node associated with a shorter reference subsequence.

For instance, a tree-like data structure serving as an index of the reference genome may be queried by tracing a path through the tree, corresponding to a subsequence of a read being mapped, that is built up by adding nucleotides to the subsequence, using the added nucleotides to select next links to traverse in the tree, and going as deep as necessary until a unique sequence has been generated. This unique sequence may also be termed a seed, and may represent a branch and/or root of the sequence tree data structure. Alternatively, the tree descent may be terminated before the accumulated subsequence is fully unique, so that a seed may map to multiple locations in the reference genome. Particularly, the tree may be built out for every starting position for the reference genome, then the generated reads may be compared against the branches and/or roots of the tree and these sequences may be walked through the tree to find where in the reference genome the read fits. More particularly, the reads of the FASTQ file may be compared to the branches and roots of the reference tree and once matched therewith the location of the reads in the reference genome may be determined. For example, a sample read may be walked along the tree until a position is reached whereby it is determined that the accumulated subsequence is unique enough so as to identify that the read really does align to a particular position in the reference, such as walking through the tree until a leaf node is reached.

A disadvantage, however, of such a prefix and/or suffix tree is that it is a huge data structure that must be accessed a multiplicity of times as the tree is walked so as to map the reads to the reference genome. An advantage of a hash table function, on the other hand, as described in greater detail herein below, is that once built, it typically only takes one look up to determine where, if anywhere, there may be a match between a seed and the reference. A prefix and/or suffix tree will typically take a plurality of look ups, e.g., 5, 10, 15, 20, 25, 50, 100, 1,000, or more, etc., in determining if and where there is a match. Further, due to the double helix structure of DNA, a reverse complement tree may also need to be built and searched, as the reverse complement to the reference genome may also need to be found. With respect to the above, the data tree is described as being built from the reference genome which is then compared with the reads from the subject's sequenced DNA, however, it is to be understood that the data tree may initially be built from either the reference sequence or the sample reads, or both, and compared one to the other as described above.

Alternatively, or in addition to employing a prefix or a suffix tree, a Burrows/Wheeler transform can be performed on the data. For instance, a Burrows/Wheeler transform may be used to store a tree-like data structure abstractly equivalent to a prefix and/or suffix tree, in a compact format, such as in the space allocated for storing the reference genome. In various instances, the data stored is not in a tree-like structure, but rather the reference sequence data is in a linear list that may have been scrambled into a different order so as to transform it in a very particular way such that the accompanying algorithm allows the reference to be searched with reference to the sample reads so as to effectively walk the "tree". An advantage of the Burrows/Wheeler transform, such as over a prefix and/or suffix tree, is that it typically requires less memory to store, and an advantage over a hash function is that it supports a variable seed length, and hence it can be searched until a unique sequence is determined and a match found. For instance, as with the prefix/suffix tree, however many nucleotides it takes for a given sequence to be unique, or to map to a sufficiently small number of reference positions, determines the length of the seed. Whereas for a hash table, the seeds are all of the same predetermined length. A disadvantage, however, for the Burrows/Wheeler transform is that it typically requires a multiplicity of lookups, such as two or more look ups, such as for every step down the tree.

Alternatively, or in addition to utilizing one or both a prefix/suffix tree and/or a Burrows/Wheeler transform on the reference genome and subject sequence data, so as to find where the one maps against the other, another such method involves the production of a hash table index and/or the performance of a hash function. The hash table index may be a large reference structure that is built up from sequences of the reference genome that may then be compared to one or more portions of the read to determine where the one may match to the other. Likewise, the hash table index may be built up from portions of the read that may then be compared to one or more sequences of the reference genome and thereby used to determine where the one may match to the other.

More particularly, in any of the mapping algorithms described herein, such as for implementation in any of the method steps herein disclosed, one or all three mapping algorithms, or others known in the art, may be employed, in software or hardware, so as to map one or more sequences of a sample of sequenced DNA with one or more sequences of one or more reference genomes. As described herein in greater detail below, all of these operations may be performed via software or by being hardwired, such as into an integrated circuit, such as on a chip, for instance as part of a circuit board. For instance, the functioning of one or more of these algorithms may be embedded onto a chip, such as into a FPGA (field programmable gate array) ASIC (application specific integrated circuit) chip, or Structured ASIC (application specific integrated circuit) chip, and may be optimized so as to perform more efficiently because of their implementation in such hardware.

Additionally, one or more, e.g., two or all three, of these mapping functions may form a module, such as a mapping module, that may form part of a system, e.g., a pipeline, that is used in a process for determining an actual entire genomic sequence, or a portion thereof, of an individual. The output returned from the performance of a mapping function may be a list of possibilities as to where one or more, e.g., each, read maps to one or more reference genomes. For instance, the output for each mapped read may be a list of possible locations the read may be mapped to a matching sequence in the reference genome. In various embodiments, an exact match to the reference for at least a piece, e.g., a seed of the read, if not all of the read may be sought. Accordingly, in various instances, it is not necessary for all portions of all the reads to match exactly to all the portions of the reference genome.

Further, one or all of these functions may be programmed in such a manner that exact or approximate matching and/or editing, such as editing of the results, may be performed. Hence, all of these processes can be configured to do inexact matching as well, where desired, such as in accordance with a preselected variance, such as 80% matching, 85% matching, 90% matching, 95% matching, 99% matching, or more. However, as described in greater detail herein below, inexact matching may be a lot more expensive such as in time and processing power requirements, because it may require any number of edits, e.g., where the edit may be a SNP or insertion or deletion of one or more bases, e.g., 1 or 2 or 3 or 5 or more edits, to be performed so as to achieve an acceptable match. Such editing is likely to be used more extensively in implementing hashing protocols or when implementing prefix and/or suffix trees and/or performing a Burrows/Wheeler transform.

With respect to hash tables, a hash table may be produced in many different ways. In one instance, a hash table may be built by breaking the reference genome into segments of standard length, e.g., seeds of about 16 to about 30 nucleotides or more in length, such as about 18 to about 28 nucleotides, formatting them into a searchable table, and making an index of all the reference segments from which sequenced DNA, e.g., one or more reads, or a portion thereof, may be compared to determine matching. More particularly, a hash table index may be generated by breaking down the reference genome into segments of nucleotide sequences of known, uniform length, e.g., seeds, and storing them in random order into individual cubicles in the reference table. This may be done for a portion or the entire reference genome so as to build an actual reference index table that may be used to compare portions of the reference genome with portions of one or more reads, such as from a FASTQ file, for the purpose of determining matching.

This method may then be repeated in approximately the same manner for a portion, e.g., a majority or all, of the reads in the FASTQ file, so as to generate seeds of the appropriate, e.g., selected, length. For instance, the reads of the FASTQ file may be used to produce seeds of a predetermined length, which seeds may be converted into binary form and fed through a hash function and fit into a hash table index where the binary form of the seeds may match up with the binary segments of the reference genome, so as to give the location as to where in the genome the sample seeds match with the position in the reference genome.

For example, where the read is approximately 100 bases long, a typical seed may be about half or a about a third, e.g., about 27 to about 30 bases, as long. Hence, in such an instance, for each read a multiplicity of seeds, e.g., approximately 3 or 4 seeds dependent on the length of the read and/or the length of the seeds, may be generated to cover the read. Each seed may then be converted into a binary form and/or then be fed into the hash table and a possible result as to its position with respect to the reference genome may be obtained. In such instances, the entire read need not be compared to every possible position in the entire reference genome, rather only a portion of the reads, e.g., one or more of the generated sample seeds per read, need only be compared such as to an index containing equivalent seed portions of the reference genome. Hence, in various instances, a hash table may be configured such that by only one memory look up it can typically be determined where the sample seed and therefore read is positioned relative to the reference genome. However, in certain instances, it may be desirable to perform a hash function and look up on one or more overlapping sections of seeds from one read. In such instances, the seeds to be generated may be formed in such a manner that at least a portion of their sequence overlaps one another. This may be useful for instance in getting around machine and/or human errors or differences between the subject and the reference genome and may promote exact matching.

In certain instances, the building of the hash table as well as the performance of one or more of the various comparisons is executed by the hash function. The hash function is in part a scrambler. It takes an input and gives what appears to be a random order to it. In this instance, the hash function scrambler breaks down the reference genome into segments of a preselected length and places them randomly in the hash table. The data may then be stored evenly across the whole storage space. Alternatively, the storage space may be segmented and/or storage therein may be weighted differently. More particularly, the hash function is a function that takes any input and gives a number, such as a binary pattern out, which number may typically random except that for any one given input the same output is always returned. Hence, even if two inputs that are fed into the hash table are almost the same, because they are not an exact match, two completely, randomly different outputs will be returned.

Further, since genetic material may be composed of four basic nucleotides, e.g., "A", "C", "G", and "T" (or "U" in the case of RNA), the individual nucleotides of the sequences, e.g., the reference segments and or reads, or portions thereof, to be fed into the hash table may be digitized and represented in binary format, such as where each of the four bases represents a two bit digital code, e.g., "A"=00, "C"=01, "G"=11, and "T"/"U"=10. In certain instances, it is this binary "seed" value that is then randomly placed in the hash table at a known location having a value equal to its binary representation. The hash function, therefore, works to break down the reference genome into binary representations of reference seeds and inserts each binary seed data into a random space, e.g., cubicle, in the hash table based on its numeric value. Along with this digital binary code, e.g., access key, each cubicle may also include the actual entry points to where the segment originated from in the actual reference genome, e.g., the reference position. The reference position therefore may be a number indicating the position of the original reference seed in the genome. This may also be done for overlapping positions, which are put into the table in random order but at known location, such as by the hash function. In a manner such as this, a hash table index may be generated, wherein the index includes the digital binary code for a portion or all of a plurality of segments of one or more reference genomes, which may then be referenced by one or more sequences of genetic material, e.g., one or more reads, or portions thereof, from one or more individuals.

When implementing the hash table and/or function as a module, such as a module in a pipeline of modules, on software (such as where the bit width is 2.times. the number of bases in the seed described above) and/or hardware, as referenced above, the hash table can be built so that the binary representation of the reference seeds can be any bit width desired. As the seeds can be long or short, the binary representations can be greater or lesser, but typically the seed length should be chosen so as to be long enough to be unique, but not too long that it is too hard to find matches between the seeds of the genome reference and the seeds of the sample reads, such as because of errors or variants. For instance, as indicated above, the human genome is made up of about 3.1 billion base pairs, and a typical read may be about 100 nucleotides in length. Hence, a useful seed length may be between about 16 or about 18 nucleotides or less in length to about 28 or about 30 nucleotides or more in length. For example, in certain instances, the seed length may be a segment of 20 nucleotides in length. In other instances, the seed length may be a segment of 28 nucleotides in length.

Consequently, where the seed length is a segment of 20 nucleotides, each segment may be represented digitally by a 40 bit output, e.g., a 40 bit binary representation of the seed. For example, where 2 bits are selected to represent each nucleotide, e.g., such as where A=00, C=01, G=10, and T=11, a seed of 20 nucleotides.times.2 bits per nucleotide=a 40 bit (5 byte) vector, e.g., number. Where the seed length may be 28 nucleotides in length, the digital, e.g., binary, representation of the seed may be a 56 bit vector. Hence, where the seed length is approximately 28 nucleotides in length, 56 bits can be employed to handle a 28 nucleotide seed length. More particularly, where the 56 bits represents the binary form of the seeds of the reference genome that have been randomly positioned in the hash table, a further 56 bits can be used to digitally represent the seeds of the read that are to be matched against the seeds of the reference. These 56 bits may be run through a polynomial that converts the 56 bits in to 56 bits out in a 1:1 correspondence. Without increasing or decreasing the number of bits of output, performing this operation randomizes the storage location of adjacent input values so that the various seed values will be uniformly distributed among all possible storage locations. This also serves to minimize collisions among values that hash to the same location. In particular, in a typical hash table implementation described herein, only a portion of the 56 bits is used as a lookup address to select a storage location and the remaining bits are stored in that location for confirmation of a match. If a hashing function were not used, a great many patterns having the same address bits, but different stored bits would have to share the same hash location.

More specifically, there is similarity between the way the hash table is constructed, e.g., by software and/or hardware placing the reference genome seeds randomly in the hash table, and the way the hash table is accessed by the seeds of the reads being hashed such that they both access the table in the same way. Hence, seeds of the reference and seeds of the sample read that are the same, e.g., have the same binary code, will end up in the same location, e.g., address, in the table because they access the hash table in the same manner, e.g., for the same input pattern. This is the fastest known method for performing a pattern match. Each lookup takes a nearly constant amount of time to perform. This may be contrasted with a Burrows-Wheeler method which may require many probes (the number may vary depending on how many bits are required to find a unique pattern) per query to find a match, or a binary search method that takes $\log_2(N)$ probes where N is the number of seed patterns in the table.

Further, even though the hash function can break the reference genome down into segments of seeds of any given length, e.g., 28 base pairs, and can then convert the seeds into a digital, e.g., binary, representation of 56 bits, not all 56 bits need be accessed entirely at the same time or in the same way. For instance, the hash function can be implemented in such a manner that the address for each seed is designated by a number less than 56 bits, such as about 20 to about 45 bits, such as about 25 to about 40 bits, such as about 28 to about 35 bits, including about 28 to about 30 bits may be used as an initial key or address so as to access the hash table.

For example, in certain instances, about 26 to about 29 bits may be used as a primary access key for the hash table, leaving about 27 to about 30 bits left over, which may be employed as a means for double checking the first key, e.g., if both the first and second keys arrive at the same cell in the hash table, then it is relatively clear that said location is where they belong. Specifically, in order to save space and reduce the memory requirements and/or processing time of the hash module, such as when the hash table and/or hash function are implemented in hardware, the about 26 to about 29 bits representing the primary access key derived from the original 56 bits representing the digitized seed of a particular sequenced read may be employed by the hashing function to comprise the primary address, leaving about 27 to about 30 bits that can be used in a double checking method.

More particularly, in various instances, about 26 to about 29 bits from the 56 bits representing the binary form of a reference seed may be employed to comprise a primary address, which designated 26 to 29 bits may then be given a randomized location in the hash table, which in turn may then be populated with the location of where the reference seed originally came from along with the remaining 27 to 30 bits of the seed so that an exact match may be ascertained. The query seeds representing the reads of the subject genome converted into binary form may also be hashed by the same function in such a manner that they as well are represented by 29 bits comprising a primary access key. If the 29 bits representing the reference seed are an exact match to the 29 bits representing the query seeds, they both will be directed to the same position in the hash table. If there was an exact match to the reference seed, then we expect to find an entry at that location containing the same remaining 27 to 30 bits. In such an instance, the 29 designated address bits of the reference sequence may then be looked up to identify the position in the reference to where the query read from which the query seed was derived, aligns.

However, with respect to the left over 27 to 30 bits, these bits may represent a secondary access key that may also be imported into the hash table as well, such as for the purpose of ensuring the results of the first 26 to 29 bits of the primary access key. Because the hash table represents a perfect 1:1 scrambling of the 28 nucleotide/56 bit sequence, and only about 26 to about 29 of the bits are used to determine the address, these 26 to 29 bits of the primary access key have basically been checked, thereby determining the correct address in a first go around. This data, therefore, does not need to be confirmed. However, the remaining about 27 to about 30 bits of the secondary access key must be checked. Accordingly, the remaining about 27 to 30 bits of the query seeds are inserted into the hash table as a means for completing the match. Such an implementation may be shorter than storing the 56 bit whole key, and thus, saves space and reduces over all memory requirements and processing time of the module.

The hash table, therefore, can be configured as an index where known sequences of one or more reference genomes that have been broken down into sequences of predetermined lengths, e.g., seeds, such as of 28 nucleotides in length, are organized into a table randomly, and one or more sequenced reads, or "seed" portions thereof, derived from the sequencing of a subject's genomic DNA or RNA, may be passed through the hash table index, such as in accordance with a hash function, so as to look up the seed in the index, and one or more positions, e.g., locations in the reference genome, may be obtained from the table where the sample seed matches positions in the reference genome. Using a brute force linear search to scan the reference genome for locations where a seed matches, over 3 billion locations would have to be checked. However, by using a hashing approach, each seed lookup can occur in approximately a constant amount of time. Often, the location can be ascertained in a single access. In cases where multiple seeds map to the same location in the table, a few additional accesses may be made to find the seed being currently looked up. Hence, even though there can be 30M or more possible locations for a given 100 nucleotide length read to match up to, with respect to a reference genome, the hash table and hash function can quickly determine where that read is going to show up in the reference genome. By using a hash table index, therefore, it is not necessary to search the whole reference genome to determine where the read aligns.

As indicted above, chromosomes have a double helix structure that is comprised of two opposed, complementary strands of nucleic acid sequences that are bound together so as to form the double helix. For instance, when the double helix structure is formed these complementary base pairs bind one with the other in accordance with the following formula: "A" binds to "T", and "G" binds to "C". Accordingly, this results in two equal and opposite strands of nucleic acid sequences that are the complement of each other. More particularly, the bases of a nucleotide sequence of one strand will be mirrored by their complementary bases on the opposed strand resulting in two complementary strands. However, transcription of DNA takes place in one direction only, starting from one end of the DNA and moving towards the other. Hence, as it turns out, for one strand of the DNA, transcription takes place in one direction, and for its complement strand, transcription takes place in the opposite direction. Consequently, the two strands of DNA sequences turn out to be reverse complemented, that is if the sequence order of one strand of the DNA is compared to the other what can be seen is two strands where the nucleotide letters of one strand are switched for their complement in the other strand, e.g., "As" for "Ts" and "Gs" for "Cs" and vice versa, and their order is reversed.

Because of the double helix structure of the DNA, during the sample prep step prior to sequencing the DNA, the chromosomes are pulled apart, e.g., de natured, separated into separate strands, and then lysed into smaller segments of a predetermined length, e.g., of 100-300 bases long, which are then sequenced. It is possible to separate the strands prior to sequencing so that only one strand is sequenced, but typically the strands of DNA are not separated and so both strands of DNA are sequenced. Accordingly, in such an instance, about half of the reads in the FASTQ file may be reverse complemented.

Of course, both strands of the reference genome, e.g., the complement and the reverse complement, may be processed and hashed as described above, however this would make the hash table twice as big, and make the performance of the hash function take twice as long, e.g., it could require about twice the amount of processing to compare both complement and reverse complemented sequences of the two genomic sequences. Accordingly, to save memory space, reduce processing power, and/or decrease the time of processing, in various instances, only one strand of the model genomic DNA need be stored in the hash table as a reference.

However, because in accordance with typical sequencing protocols, such as where the two strands of the subject DNA have not been isolated from one another, any read generated from the sequenced DNA can be from either strand, the complement or its reverse complement, it may be difficult to determine which strand is being processed, the complement of the reverse complement. More specifically, in various instances, since only one strand of the reference genome need be used to generate the hash table, half of the reads generated by the sequencing protocol may not match the particular strand, e.g., either the complement or its reverse complement, of the model genome reference, e.g., because half the time the read being processed is a reverse complement with respect to the hashed segments of the reference genome. Hence, only the reads generated from one strand of the DNA will match the indexed sequences of the reference genome, while the reads generated from the other strand will theoretically be their reverse complements and will not match anywhere in the reference genome. Further, an additional complication can be that for any given read that is reverse complemented to the stored reference genome strand, the read may still, erroneously, match to a portion of the reference genome, such as by mere chance. In view of the above, in order for mapping to proceed efficiently, in various instances, it not only must be determined where the read matches in the reference genome it must also be determined if the read is reverse complemented. Therefore, the hash table and/or function module should be constructed so as to be able to minimize these complications and/or the types of errors that may result therefrom.

For instance, as indicated above, in one instance, the hash table could be populated with both the complement and the reverse complement for the reference genome so that every read or its reverse complement of the subject's sequenced DNA can be matched to its respective strand in the genomic reference DNA. In such an instance, for any given seed in a read, the seed should theoretically match with one strand or the other, the complement or the reverse complement of the reference, assuming no errors or variations. However, storing both strands of the reference genome in the hash index can require about twice as much storage space (e.g., instead of 32 gigabytes 64 gigabytes may be necessary), and may require twice the amount of processing resources and/or twice as much time for processing. Further, such a solution doesn't solve the problem of palindromes that can match in both directions, e.g., the complement and reverse complement strands.

Accordingly, although the hash table index may be constructed to include both strands of the genomic reference sequence. In various instances, the hash table may be constructed so as to only include one strand of the model genome as a reference. This may be useful because storing the hash table in memory will require half of the storage and/or processing resources than would be required if both strands were to be stored and processed, and thus, the time required for a look up should also require less time. However, storing only one strand of the genome as a reference could cause complications because, as indicated above, where the sequenced subject DNA is double stranded, it is not typically known from which strand any given read was generated. In such an instance, therefore, the hash table should be constructed to account for the fact the read being mapped may be from either strand and thus can be the complement or reverse complement of the stored segments of the reference genome.

Accordingly, in various instances, such as where only one orientation of seeds from the reference are populated into the hash table, when performing the hash function on the seeds generated from the reads of the FASTQ file, the seed may first be looked up in its present orientation, and/or may then be reverse complemented and the reverse complement may be looked up. This may require two looks up in the hash index, e.g., twice as many, but one of the seed or its reverse complement should match its complementary segment in the reference genome, assuming no errors or variations, and it should reduce the overall processing resources, e.g., less memory is used, as well as reducing time, e.g., not as many sequences need to be compared.

More particularly, such as where a seed in one particular orientation is comprised of 28 nucleotides, e.g., digitally represented in a 56 bit binary format, as described above, the seed can be reverse complemented and the reverse complement can also be represented digitally in a 56 bit binary format. The binary format for each representation of the seed sequence and its complement results in a number, e.g., an integer, having a value represented by that number. These two values, e.g., the two integers, may be compared and the number with the higher or lower value, e.g., higher or lower absolute value, may be selected as the canonical choice of orientation and that is the one that can be stored in the hash table and/or subjected to the hash function. For instance, in certain instances, the number with the higher value may be selected for being processed by the hash function.

Another method that may be employed is to construct seeds wherein each seed is comprised of an odd number of bases. The canonical orientation to be selected then may be those strands having a middle base being an "A" or a "G", but not a "T" or a "C", or vice versa. The hash function then will be performed on the seeds meeting the requirements of the canonical orientation. In such a manner, it is only the two bits representing the middle base that needs to be compared to see which has the higher value and it is only the 2 bits of that sequence that are looked up. Hence, you only have to look at the bits representing the middle two bases. Typically, this can work well because if the seed is an odd length, then it always reverse complements the center base. However, although this may work for odd seed lengths, hashing those seeds having a higher, or lower, value, as described above, should work for all seed lengths, albeit such a method may require having to process, e.g., look up, more bits of data.

These methods may be performed for any number of seeds, e.g., all seeds of the reference and/or any number of seeds, e.g., all, derived from all or a portion of the reads of the FASTQ file. Approximately half of the time the binary representation of the seeds of a given orientation, e.g., the complement, will have a higher value, and approximately half the time the binary representation of the seeds of the opposite orientation, e.g., the reverse complement, will have the higher value. But, when looking at the binary numbers, whichever one has the higher value, that is the one that gets fed into the hash table. For instance, the binary integers for each read and its complement may be compared, and the sequence having the first 1 encountered is the one of the two strands selected to be stored as the strand in the hash table and/or be subjected to the hash function. If both strands have a first 1 in the same position, then the strand having the second 1 that comes first is selected, and so on. Of course, the read with the lower value may also be selected, in which case the strand having the first and/or larger number of initial 0's will be selected. An indication, e.g., a flag, may also be inserted into the hash table where the flag indicates which orientation, complement or reverse complement, the stored and/or hashed strand represents, e.g., a 1RC flag, if reverse complemented.

More particularly, when performing the hash function and accessing the hash table, seeds from the genomic reference DNA and seeds derived from the reads of the sequence data are subjected to these same operations, such as converted into binary form and compared with its reverse complement where the integers having the higher, or lower, values are selected as the canonical orientations and subjected to the hash function and fed into the hash table to be looked up and matched against each other. However, because it is the same operation being performed in substantially the same manner on the reference sequences and the read sequences, the same record will be derived, if the two sequences, the reference and the subject seeds, have the same sequence to begin with, even if one was reverse complemented, they will all be directed to the same cell in the hash table.

Consequently, if a certain seed in the reference having a given sequence in a particular orientation is converted to binary form and hashed, and then a seed derived from a sample read having the same sequence, but in its reverse orientation, e.g., reverse complemented, and it is subjected to the above protocols, because of the above disclosed methods, when the binary value is determined and the hash function performed, the look up will be directed to the very same address in the hash table as if the hash function were performed on the complimentary seed to begin with. Hence, in this manner it doesn't matter which orientation the seed being processed is in because it will always be directed to the same address.

Therefore, in a manner such as this, the methods herein disclosed are able to hash and thereby determine the location of the seed within the table despite its orientation, and because of the flag in the record it will also be known if any given seeds is reverse complemented. For instance, it will be known if the seed was flipped from the reference and it will also be known if the seed derived from the subject read had to be flipped as well. Consequently, if the decision was the same on both sides then the orientation is the same between the read and the reference. However, if one side is flipped and the other is not, then it can be concluded that the read maps reverse complemented to the reference. Hence, by using a hash table it may be determined where in the genome a given read, or portion thereof, e.g., a seed, matches and/or if it is reverse complimented. Further, it is to be understood that although the above is described with respect to generating the hash table from the reference genome and performing various ancillary hash function processes on the seeds generated from the reads, e.g., from a FASTQ file, the system can also be structured such that the hash table index is generated from seeds derived from the reads of the subject's sequenced DNA, and the various ancillary hash function processes, as herein described, are performed on seeds generated from the reference genome.

As set forth above, an advantage of employing a hash table and/or a hash function is that by employing the use of seeds, a majority of the reads of the sequenced DNA can be matched to the reference genome often by employing single hash lookups, and in various instances, not all seeds derived from a read need be hashed and/or looked up. Seeds may be of any suitable length, such as relatively short, e.g., 16 nucleotides or less, such as about 20 nucleotides, such as about 24 nucleotides, such as about 28 nucleotides, such as about 30 or about 40 or about 50, or 75 or about 100 nucleotides, or even up to 250 or 500, or 750, or even 999 or even about 1,000 nucleotides in length; or relatively long such as over about 1,000 nucleotides or over about 10,000, or over about 100,000 or over 1,000,000 or more nucleotides in length. However, as described above, there are some disadvantages to using seeds, such as in a hash table, in particular with respect to selecting seeds of the appropriate length.

For instance, any suitable seed length may be employed in a mapping function, however there are advantages and disadvantages of using relatively short or relatively long seed lengths. For example, the shorter the seed length the less likely it is to incorporate an error or a variation that can prevent finding a match within the hash table. However, the shorter the seed length, the less unique it is, and the more matching is to be expected between the seeds of the reference genome and the seeds derived from the reads of the subject's sequenced DNA. Further, the shorter the seed length the more lookups will have to be performed by the hash function, taking more time and increased processing power.

On the other hand, the longer the seed length the more unique it is and the less likely there is to be multiple matching positions between the seeds between the seeds of the reference and the query. Also, with a longer seed, there need be fewer seeds within the read, so fewer look ups, thereby taking less time and requiring less processing power. The longer the seed, however, the more likely it is that the seeds derived from the sequenced DNA may include an error, such as a sequencing error and/or may incorporate a variation as compared to the reference thus preventing a match from being made. Longer seeds further have the disadvantage of being more likely to hit the end of the read and/or the end of the chromosome. Hence, where a seed is only 20-100 nucleotides in length, there may be several matches within the hash table, however, where the seed is 1,000 or more nucleotides in length there may be much fewer matches, but there may be no matches at all.

There are some methods for helping to minimize these issues. One method is to ensure there is appropriate oversampling generated in the DNA processing steps prior to sequencing. For instance, as it is known that there is typically at least one variation within every 1,000 base pairs, the seed length may be chosen to maximize matches, while at the same time minimizing non-matches due to the incorporation of errors and/or variants. Additionally, the use of oversampling, such as in the pre-sequencing and/or sequencing steps, can be employed as a further method for minimizing various problems that are inherent to using seeds, such as within a hash function.

As indicated above, oversampling produces pileups. Pileups are those collections of reads that map in an overlapping fashion generally to the same place in the genome. For the majority of sample reads, such pileups may not be necessary, such as where the reads, and/or seeds generated therefrom, do not include a variant and/or do not map to multiple positions in the hash table (e.g., are not exactly duplicated in the genome). However, for those reads and/or seeds that may include a variant and/or an error and/or other mismatch between the seed and/or read and the reference genome, the production of pileups for any given region of the genome may be useful. For instance, even though only one exact hit between a seed generated from a read of the sample genome is necessary so as to be able to map the sample read to the reference genome, however, the fact that there may be a machine error or a true variant in the sample DNA sequence that could prevent such an exact match between the read and the reference from occurring, often times makes the production of overlapping pileups in the pre-sequencing and sequencing steps useful.

For example, for those instances where a sample seed does in fact contain a variant or an error, the production of read pileups may be useful in distinguishing between actual variance and machine and/or chemistry errors. In such an instance, a pileup can be employed to determine whether an apparent variation is in fact a real variation. For instance, if 95% of the reads in the pileup indicate that there is a "C" in a certain position, then odds are that is the correct call, even if the reference genome has a "T" at that location. In such an instance, the mismatch may be due to a SNP, e.g., a substitution of a "C" for a "T" in that position in the genome, where the genetic code for the individual actually varies from that of the reference. In such an instance, the depth of the pileup may be employed so as to compare the overlapping portions of the reads of the pileup at a position where there is variance, and based on the percentage of reads in the pileup having the variance, it can be determined whether the variance is in fact due to an actual variation in the sample sequence. Accordingly, the actual sequence of the reads that best fits the genomic sequence, may in part be determined based on what is reflected in the pileup depths. The disadvantage of using pileups, however, is that it requires more processing time to process all the excess reads and/or seeds generated thereby.

Another method for minimizing the issues inherent in short or long reads is to employ a secondary hash table along with or in conjunction with the first, e.g., primary hash table. For instance, a second hash table and/or hash function may be employed for those seeds that do not have any hits in the primary hash table, or for those seeds that have multiple hits in the primary hash table. For example, when comparing one seed with another there are several outcomes that may result. In one instance, a no hit, e.g., a no match anywhere between the two sequences, may result, in which case this suggests a possible error or variation such as in the seed of a read of the subject as compared against a seed derived from the reference genome. Or there may be one or a plurality of matches found. If a large number of matches are found, however, this could be problematic.

For instance, with respect to the primary hash table, if each seed in the reference being hashed appears only a few times, e.g., once, twice, or three times, etc. then there may not be a need for a secondary hash table and/or hash function. However, if one or more of the seeds occurs a greater number of times, e.g., 5, 10, 15, 20, 25, 50, 100, 1,000, or more times, this could be problematic. For example, there are known regions in the sequence of the human genome that have been determined to be mathematically significant in that they are repeated a multiplicity of times. Consequently, any seed mapping to one of these positions, may in fact inadvertently map to a multiplicity of these positions, such as where the seed comprises the nucleotides of the overlapping sequences. In such an instance, determining which out of all the possibilities the seed actually aligns to may be difficult. However, as these repeating regions are known, and/or become known, any seed that would typically map to one or more of these regions may be demarcated to be allocated to a secondary hash table for processing by the first or a secondary hash function, so as to not waste time and processing power trying to use a primary hashing function to determine something that is likely to be indeterminable.

More particularly, when comparing the seeds of the genomic reference to the seeds generated from the subject's genomic reads, anywhere from 1 to hundreds or even thousands of match positions may result. The present system, however, may be configured to handle a certain number of duplicative matches, such as without the need for further processing steps, such as where the number of matches is below about 50, or below about 40, or below about 30, such as below about 25 or about 20, such as below about 16 matches or below about 10 or about 5 matches. However, if there are more matches of viable hits than this that are returned, then the system can be configured to implement a secondary hash function, e.g., using a secondary hash table.

Accordingly, rather than placing such seeds known to have an increased likelihood of redundancy in the primary hash table, such seeds can be placed in a secondary hash table, or a secondary region in the first hash table. Additionally, in some instances, a record that doesn't communicate anything about the multiplicity of potential map positions for that seed, but rather communicates a command to access a secondary hash table, e.g., an extend record, can be placed in the primary hash table. For example, the extend record can be an instruction, such as an instruction to extend the primary, e.g. non unique or duplicative, seed length to a longer, more unique seed length, such as by adding on one or more additional bases next to it, e.g., on the end(s) of the seed, to make it a longer seed sequence that can then get hashed and looked up, such as in the secondary table.

The record can be configured such that it informs or otherwise instructs how much to extend the known redundant seed by a given amount, and may also instruct as to where and/or how to extend the seed. For instance, because the hash table is usually precomputed, e.g., originally constructed from the seeds generated from the reference genome(s), it may be known prior to constructing the table, which, if any, of the seeds generated from the reference genome are going to occur a multiplicity of times. Hence, in various instances, it may be predetermined which seeds are going to need to be shifted over to the secondary hash table. For example, when constructing the hash table index, the characteristics of the reference seed sequences being input into the hash table as an index are known, so for every potential seed it may be determined whether it's a case that is going to give a multiplicity of hits, e.g., from 10-10,000 hits.

More particularly, in various instances, an algorithm can be performed to determine all the predicted matches a given seed derived from the reference and/or the subject's reads may have. If it is determined that for any particular seed that it is likely to return a multiplicity of matches, a flag, e.g., a record, may be generated, such as within a cell of the hash table, indicating that this particular seed is a high frequency hit. In such an instance, the record can further instruct that the primary hashing of this seed, and such seeds like it, should be skipped over because it is not practical to perform the number, e.g., 20-10,000 or more evaluations on such a seed needed to accurately determine where the seed actually maps. In such an instance, the primary hash function may not be able to accurately determine which position out of all the possible positions to where the seed may match, is the one to where the read actually aligns, and thus for practical purposes, because the seed cannot accurately be mapped at this stage, the primary hash function may not be likely to return a useable result, such as a result indicating accurately where the seed actually matches in the genome.

In such an instance, the hash function algorithm may be configured to calculate what would need to be done to make the redundant seed more unique. For example, the secondary hash function may determine by how many bases the seed needs to be extended, and in what order, and in what location, so as to ensure that the seed is no longer redundant, but rather suitably unique so as to be hashed. Accordingly, the record may also include an instruction to extend the redundant seed, e.g., extend by two, by four, by six, etc., on one or both ends of the seed so as to achieve a predetermined level of uniqueness. In such a manner as this, seeds that at first appear to be identical can be determined to be non-identical.

For example, in some instances, a typical record can instruct that the duplicative seed be extended by up to X number of odd or even bases, but in some instances, extended by an even number of bases, such as from about 2 to 4 to about 8 to 16 to about 32 or about 64 or more bases, such as equally on each side. For instance, where the extension is to be by 64 bases, the record could instruct that 32 bases be added on each side of the seed. The number of bases by which the seed is to be extended is configurable and may be any suitable number dependent on how the system is constructed. In certain instances, the secondary hash function may be employed to determine by how many bases the seed should be extended so as to get a more reasonable number of match results back. Therefore, the extension may be to the point of relative uniqueness, such as to where there is only 1, 2, 3, or even up to 16 or 25 or 50 match positions where the pattern shows up. In various instances, extending the seed equally from both ends may be useful such as to avoid problems with reverse reads, but in various instances the seed may be extended by the addition of one or more bases unequally to both sides.

More particularly, such as in one example, if the seed includes 28 bases, and an extend record, such as an extend record positioned within a cell in the primary hash table, instructs the hash function to extend the seed, such as by 64 bases, then the record may further direct the hash function as to how to extend the seed, such as by adding 32 bases on each side of the seed. However, the extension can take place at any suitable position on the read and may be done in a symmetrical or asymmetrical fashion. In certain instances, the record may instruct the hash function to extend the seed symmetrically because in certain instances such a symmetrical extension may work better, such as with reverse complements, discussed herein. In such an instance, the same number of bases will be added such as to the opposite sides of the seed when extending. Although in other instances extension may be performed by adding an even or an odd number of bases in a non-symmetrical format, and hence, it is not necessary to extend the seed by same number of bases on each side. Typically, the primary hash table is configured such that it is not completely full. For example it is desirable to configure it not to exceed 80% or 90% of its capacity. This is to maintain high performance of the lookup rate. When there are a high number of collisions in hashing seeds to the same location when constructing the table, the storing mechanism will create a chain of references to other locations so that the lookup mechanism will be able to find the one assigned to the overflowed seed. The denser the table, the higher the number of collisions and the longer the chains to be followed to find the actual match.

In various instances, such as where the initial, redundant seed is 28 bases long, and the record instructs for it to be extended, such as from 18 to 32 to 64 bases, such as on each opposed side of the seed, the digital representation of the seed may be about 64 bases.times.2 bits per base=128 bits. Accordingly, dependent on how the mapping module is set up, this may be too big for the primary hash table to process. Hence, in certain instances, to deal with the need for such extensive processing, in certain embodiments, the secondary hashing module can be configured to store the information associated with larger seeds. Since the number of seeds requiring extension is a fraction of the total number of seeds, the secondary hash table may be smaller than the primary hash table. However, in other instances, such as to reduce the processing requirements of the module, e.g., to save bits, the known redundant portion of the sequence, e.g., the primary sequence, may be replaced by a preselected variable such as of a predetermined sequence length. In such an instance, since the redundant sequence is already known and identified, it does not need to be digitally represented in its entirety. Rather, in various instances, all that is really needed to be done is to substitute the known, redundant sequence with a known variable sequence, and all that really needs to be looked up are the extension portions, e.g., wings, that have been added to either side of the variable sequence, since those are the only portions of the initial sequence that are non-redundant and new. Hence, in certain instances, the primary sequence may be replaced by a shorter unique identifier code (such as a 24 bit proxy instead of 56 bit representation) and then the extension bases can be added to the proxy, such as a 36 bit extension (e.g., totaling 60 bits) that can then be put into the extend record in the primary table. In a manner such as this, the disadvantages of having too short and/or too long of reads can be minimized and the benefit of having only one or a few look ups in the hash table can be maintained.

As indicated above, the implementation of the above described hash function may be executed in software of hardware. An advantage of implementing the hash module in hardware is that the processes may be accelerated and therefore performed in a much faster manner. For instance, where software may include various instructions for performing one or more of these various functions, the implementation of such instructions often requires data and instructions to be stored and/or fetched and/or read and/or interpreted, such as prior to execution. As indicated above, however, and described in greater detail herein below, a chip can be hardwired to perform these functions without having to fetch, interpret, and/or perform one or more of a sequence of instructions. Rather, the chip may be wired to perform such functions directly. Accordingly, in various aspects, the disclosure is directed to a custom hardwired machine that may be configured such that portions or all of the above described hashing module may be implemented by one or more network circuits, such as integrated circuits hardwired on a chip, such as an FPGA, ASIC or Structured ASIC.

For instance, in various instances, the hash table index may be constructed and the hash function may be performed on a chip, and in other instances, the hash table index may be generated off of the chip, such as via software run by a host CPU, but once generated it is loaded onto and employed by the chip, such as in running the hash module. In certain instances, the chip may include any suitable number of gigabytes, such as 8 gigabytes, such as 16 gigabytes, such as 32 gigabytes, such as 64 gigabytes, such as about 128 gigabytes. In various instances, the chip may be configurable such that the various processes of the hash module are performed employing only a portion or all the memory resources. For example, where a custom reference genome may be built, a large portion of the memory may be dedicated to storing the hash reference index and/or for storing reads and/or for reserving space for other functional modules to use, such as where 16 gigabytes are dedicated to storing the reads, 8 gigabytes may be dedicated to storing the hash index and another 8 gigabytes may be dedicated to other processing functions. In another example, where 32 gigabytes are dedicated to storing reads, 26 gigabytes may be dedicated for storing the primary hash table, 2.5 gigabytes may be dedicated for storing the secondary table, and 1.5 gigabytes may be dedicated for the reference genome.

In certain embodiments, the secondary hash table may be constructed so as to have a digital presence that is larger than the primary hash table. For instance, in various instances, the primary hash table can be configured to store hash records of 8 bytes each with 8 records per hash bucket totaling 64 bytes per bucket, and the secondary hash table can be configured to store 16 hash records totaling 128 bytes per bucket. For each hash record containing overflow hash bits matching the same bits of the hash key a possible matching position in the reference genome is reported. For the primary hash table therefore, up to 8 positions may be reported. For the secondary hash table up to 16 positions may be reported.

Regardless of being implemented in hardware or software, in many instances, it may be useful to structure the hash table to avoid collisions. For instance, there may be multiple seeds that, because of various system artifacts will want to be inserted into the hash table at the same place regardless of whether there is a match there or not. Such instances are termed collisions. Often times, collisions can be avoided, in part, by the way the hash table is structured. Accordingly, in various instances the hash table may be structured so as to avoid collisions, and therefore may be configured to include one or more virtual hash buckets.

In various instances, the hash table can be structured such that it is represented in an 8 byte, 16 byte, 32 byte, 64 byte, 128 byte format, or the like. But in various exemplary embodiments it may be useful to represent the hash table in a 64 byte format. This may be useful, for instance, where the hash function is to make use of accessing a memory, such as a DRAM, e.g., in a standard DIMM or SODIMM form factor, such as where the minimum burst size is typically 64 bytes. In such an instance, the design of the processor for accessing a given memory will be such that the number of bytes needed to form a bucket in the hash table is also 64, and therefore a maximized efficiency may be realized. However, if the table were to be structured in a 32 byte format, this would be inefficient because about half the bytes delivered in a burst would contain information not needed by the processor. That would cut the effective byte delivery rate in half. Conversely, if the number of bytes used to form a bucket in the hash table is a multiple of the minimum burst size, e.g., 128, there is no performance penalty as long as the processor actually needs all of the information returned in a single access. Therefore, in instances where the optimal burst size of the memory access is at a given size, e.g., 64 bytes, the hash table can be structured so burst size of the memory is optimally exploited, such as where the bytes allocated for representing bins in the hash table and processed by the mapping function, e.g., 64 bytes, are coincident with the burst size of the memory. Consequently, where the memory bandwidth is a constraint, the hash table can be structured so as to optimally exploit such constraints.

Further, it is to be noted, that although a record may be crammed into 8 bytes, the hash function can be constructed such that it is not the case that 8 bytes from the table are read so as to process one record, as this could be inefficient. Rather, all 8 records in a bucket can be read at once, or some sub-portion thereof. This may be useful in optimizing the processing speed of the system as, given the architecture described above, it would cost the same time at the same speed to process all 8 records as it would for simply processing 1 record. Accordingly, in certain instances, the mapping module may include a hash table that itself may include one or more subsections, e.g., virtual sections or buckets, wherein each bucket may have 1 or more slots, such as 8 slots, such that one or more different records can be inserted therein such as to manage collisions. However, in certain circumstances, one or more of such buckets may fill up with records, so a means may be provided for storing additional records in other buckets and recording information in the original bucket indicating that the hash table lookup mechanism needs to look further to find a match.

Hence, in certain instances it may also be useful to employ one or more additional methods such as for managing collisions, one such method may include one or more of linear probing and/or hash chaining. For instance, if it is not known what exactly is being searched in the hash table or a portion thereof, such as in one bucket of the hash table, and the particular bucket is full, then the hash lookup function can be configured such that if one bucket is full and is searched and the desired record not found, then the function can be directed to step to the next bucket, e.g., the +1 bucket, and that bucket can then be checked. In such a manner, all buckets can be searched when looking for a particular record. Such searching, therefore, can be performed sequentially looking through one bucket to another until what is being looked for is found or it becomes clear that it is not going to be found, such as where an empty slot in at least one of the buckets is found. Particularly, where each bucket is filled sequentially, and each bucket is searched according to the sequence of filling, if an empty slot is found, such as when searching sequentially through buckets looking for a particular record, then the empty slot could be indicative of the record not existing, because if it did exist, it would at least have been positioned in the empty slot, if not in the preceding buckets.

More particularly, where 64 bytes are designated for storing the information in a hash bucket wherein 8 records are contained, upon receiving a fetched bucket, the mapping processor can operate on all 8 records simultaneously to determine which are matches and which are not. For instance, when performing a look up such as of a seed from a read obtained from the sequenced sample DNA against a seed generated from the reference genome, the digital representation of the sample seed can be compared against the reference seeds in all, e.g., 8, records so as to find a match. In such an instance, several outcomes may result. A direct match may be found. A sample seed may go into the hash table and, in some instances, no match is found, e.g., because it is just not exactly the same as any corresponding seed in the reference, such as because there was a machine or sequencing error with respect to that seed or the read from which it is generated, or because the person has a genetic sequence that is different from the reference genome. Or a the seed may go into the hash table and a plurality of matches may be returned, such where the sample seed matches to 2, 3, 5, 10, 15, 20, or more places in the table. In such an instance, multiple records may be returned all pointing to various different locations in the reference genome where that particular seed matches, the records for these matches may either be in the same bucket, or a multiplicity of buckets may have to be probed to return all of the significant, e.g., match, results.

In certain instances, such as where space may become a limiting factor in the hash table, e.g., in the hash table buckets, an additional mechanism for resolving collisions and/or for saving space may implemented. For instance, when space becomes limited, such as when more than 8 records need to be stored in a bucket, or when for other instances it is desirable, a hash chaining function may be performed. Hash chaining can involve, for example, replacing a record containing a specific position location in the genomic sequence with a record containing a chain pointer that instead of pointing to a location in the genome points to some other address, e.g., a second bucket in the current hash table e.g. a primary or a secondary hash table. This has the advantage over the linear probing method of enabling the hash lookup mechanism to directly access the bucket containing the desired record rather than checking buckets sequentially in order.

Such a process may be useful given the system architecture. For instance, the primary seeds being hashed, such as in a primary lookup, are positioned at a given location in the table, e.g., their original position, whereas the seeds being chained are being put in a position that may be different from their original bucket. Hence, as indicated above, a first portion of the digitally represented seed, e.g., about 26 to about 29 bits, can be hashed and may be looked up in a first step. And, in a second step, the remaining about 27 to about 30 bits can be inserted into the hash table, such as in a hash chain, as a means for confirming the first pass. Accordingly, for any seed, its original address bits may be hashed in a first step, and the secondary address bits may be used in a second, confirmation step. Hence, the first portion of the seeds can be inserted into primary record location, and the second portion may be fit into the table in secondary record chain location. And, as indicated above, in various instances, these two different record locations may be positionally separated, such as by a chain format record. Therefore, in any destination bucket of chaining a chain format record may positionally separate the entries/records that are for local primary first bucket accesses and probing and those records that are for the chain.

Such hash chains can be continued for a multiplicity of lengths. An advantage of such chaining is that where one or more of the buckets include one or more, e.g., 2, 3, 4, 5, 6, or more empty record slots, these empty slots can be used to store the hash chain data. Accordingly, in certain instances, hash chaining may involve starting with an empty slot in one bucket and chaining that slot to another slot in another bucket, where the two buckets may be at remote locations in the hash table. Additional care may be taken to avoid confusion between records placed in a remote bucket as part of a hash chain, and "native" records that hash directly into the same bucket. As usual, the remaining about 27 to about 30 bits of the secondary access key are checked against corresponding about 27 to 30 bits stored in the records placed remotely in the chained bucket, but due to the distant placement of the chained bucket from the original hash bucket, confirming these about 27 to 30 bits would not be enough to guarantee that a matching hash record corresponds to the original seed reaching this bucket by chaining, as opposed to some other seed reaching the same bucket by direct access. (e.g., confirming the about 27 to 30 bits may be a full verification when the about 26 to 29 bits used for hash table addressing are implicitly checked by proximity to the initial hash bucket accessed.)

To prevent retrieving a wrong hash record without needing to store entire hash keys in the records, a positional system may be used in a chained bucket. Accordingly, a chained bucket must contain a chain continuation format record, which contains a further chain pointer to continue the bucket chain if required; this chain continuation record must appear in a slot of the bucket after all "native" records corresponding to direct hash access, and before all remote records belonging to the chain. During queries, before following any chain pointer, any records appearing after a chain continuation record should be ignored, and after following any chain pointer, any records appearing before a chain continuation record should be ignored.

For example, where the buckets are about 75%-85% full, 8 buckets may be scanned and only 15-25 slots may be found that can be used, whereas with hash chaining these slots may be found over 2 or 3 or 4 buckets. In such an instance, the number of probe or chain steps required to store a hash record matters because it influences the speed of the system. At run time, if probing is necessary to find the record, a multiplicity of hash look up accesses, e.g., a 64 byte bucket read, may need to be performed which slows the system down. Hash chaining helps to minimize the average number of accesses that have to be performed, because more excess hash records can generally be populated per chained bucket, which can be selected from a wide region, than per probing bucket, which must be sequentially next. Therefore, a given number of excess hash records can typically be populated into a shorter sequence of chained buckets than the necessary sequence of probing buckets, which likewise limits the number of accesses required to locate those excess records in a query. Nevertheless, probing remains valuable for smaller quantities of excess hash records, because probing does not require a bucket slot to be sacrificed for a chain pointer.

For example, after it has been determined where all the possible matches are for the seeds against the reference genome, it must be determined which out of all the possible locations a given read may match to is in fact the correct position to which it aligns. Hence, after mapping there may be a multiplicity of positions that one or more reads appear to match in the reference genome. Consequently, there may be a plurality of seeds that appear to be indicating the exact same thing, e.g., they may match to the exact same position on the reference, if you take into account the position of the seed in the read.

The actual alignment, therefore, must be determined for each given read. This determination may be made in several different ways. In one instance, all the reads may be evaluated so as to determine their correct alignment with respect to the reference genome based on the positions indicated by every seed from the read that returned position information during the hash lookup process. However, in various instances, prior to performing an alignment, a seed chain filtering function may be performed on one or more of the seeds. For instance, in certain instances, the seeds associated with a given read that appear to map to the same general place as against the reference genome may be aggregated into a single chain that references the same region. All of the seeds associated with one read may be grouped into one or more seed chains such that each seed is a member of only one chain. It is such chain(s) that then cause the read to be aligned to each indicated position in the reference genome. Specifically, in various instances, all the seeds that have the same supporting evidence indicating that they all belong to the same general location(s) in the reference may be gathered together to form one or more chains. The seeds that group together, therefore, or at least appear as they are going to be near one another in the reference genome, e.g., within a certain band, will be grouped into a chain of seeds, and those that are outside of this band will be made into a different chain of seeds.

Once these various seeds have been aggregated into one or more various seed chains, it may be determined which of the chains actually represents the correct chain to be aligned. This may be done, at least in part, by use of a filtering algorithm that is a heuristic designed to eliminate weak seed chains which are highly unlikely to be the correct one. Generally, longer seed chains, in terms of length spanned within the read, are more likely to be correct, and furthermore, seed chains with more contributing seeds are more likely to be correct. In one example, a heuristic may be applied wherein a relatively strong "superior" seed chain, e.g. long or having many seeds, filters out a relatively weak "inferior" seed chain, e.g. short or having few seeds. In one variation, the length of an inferior chain determines a threshold length, e.g. twice as long, such that a superior chain of at least the threshold length can filter it out. In another variation, the seed count of an inferior chain determines a threshold seed count, e.g. five times as many seeds, such that a superior chain of at least the threshold seed count can filter it out. In another variation, the length of an inferior chain determines a threshold seed count, e.g. two times the seed count minus the seed length, such that a superior chain of at least the threshold seed count can filter it out. In some variations, such as when chimeric alignments of reads are desired, only superior seed chains substantially overlapping inferior seed chains within the read may filter them out.

This process weeds out those seeds that have a low probability of having identified a region of the reference genome where a high quality alignment of the read can be found. It, therefore, may be useful because it reduces the number of alignments that need to be performed for each read thereby accelerating the processing speed and saving time. Accordingly, this process may be employed, in part, as a tuning feature, whereby when greater speed is desired, e.g., high speed mode, more detailed seed chain filtering is performed, and where greater overall accuracy is desired, e.g., enhanced accuracy mode, less seed chain filtering is performed, e.g., all the seed chains are evaluated.

In various embodiments, seed editing may be performed, such as prior to a seed chain filtering step. For instance, for each read, if all of the seeds of that read are subjected to a mapping function and none of them returned a hit, then there may be a high probability that there was one or more errors in the read, for instance, an error that the sequencer made. In such an instance, an editing function, such as a one-change editing process, e.g., an SNP editing process, can be performed on each seed, such as where a no match outcome was returned. For example, at position X, a one change edit function may instruct that the designated nucleotide be substituted for one of the other 3 nucleotides and it is determined whether a hit, e.g., a match, is obtained by making that change, e.g., a SNP substitution. This one-change editing may be performed in the same manner on every position in the seed and/or on every seed of the read, e.g., substituting each alternative base for each position in the seed. Additionally, where one change is made in one seed, the effects that change would have on every other overlapping seed may be determined in view of that one change.

Such editing may also be performed for inserts, such as where one of the four nucleotides is added at a given insert position, X, and it is determined if a hit was obtained by making the substitution. This may be done for all four nucleotides and/or for all positions (X, X+1, X+2, X+3, etc.) in the seed and/or all the seeds in the reads. Such editing may also be performed for deletions, such as where one of the four nucleotides is deleted at a given position, X, in the seed, and it is determined if a hit was obtained by making the deletion. This may then be repeated for all positions X+1, X+2, X+3, etc. Such editing, however, can result in a lot of extra processing work and time, such as by requiring a multiplicity of additional lookups, such as 2, or 3, or 4, or 5, or 10, or 50, or 100, or 200, etc. Nevertheless, such extra processing and time may be useful if by such editing an actual hit can be determined, e.g., a match made, where before there was no match. In such an instance, it can then typically be determined that an error was made and further that it was corrected, thereby salvaging the read.

Additionally, a further heuristic may be employed so as to determine whether an editing function should be performed or not, whereby the algorithm performs a calculation to determine the probability that a hit will be obtained if such editing were to be performed. If a certain threshold probability is met, such as 85% likelihood, then such seed chain editing may be performed. For instance, the system can generate various statistics on the seed chains, such as calculating how many high frequency hits are present and/or how many seed chains contain high frequency hits, and thereby determine if seed chain editing is likely to make a difference in determining matches. For example, if it is determined that there are a large proportion of high frequency hits, then, in such an instance, seed chain editing may be skipped because it is unlikely to make various of the sequences unique enough to give a hit within a reasonable number of hash table look ups, such as 100 or fewer, 50 or fewer, 40 or fewer, 30 or fewer, 20 or fewer, or 10 or fewer. Such statistics can be reviewed and it may then be determined whether to do seed editing or not. For instance, if the statistics show that for any one read, if half the positions show no match, and the others show high frequency matches, then it is probably worth doing seed editing, because where no matches are returned, there is probably an error, but if a lot of high frequency matches are returned it may simply not be worth performing seed editing.

The outcome from performing one or more of these mapping, filtering, and/or editing functions is a list of reads which includes for each read a list of all the possible locations to where the read may matchup with the reference genome. Hence, a mapping function may be performed so as to quickly determine where the reads of the FASTQ file obtained from the sequencer map to the reference genome, e.g., to where in the whole genome the various reads map. However, if there is an error in any of the reads or a genetic variation, you may not get an exact match to the reference and/or there may be several places one or more reads appear to match. It, therefore, must be determined where the various reads actually align with respect to the genome as a whole.

Accordingly, after mapping and/or filtering and/or editing, the location positions for a large number of reads have been determined, where for some of the individual reads a multiplicity of location positions have been determined, and it now needs to be determined which out of all the possible locations is in fact the true or most likely location to which the various reads align. Such aligning may be performed by one or more algorithms, such as a dynamic programming algorithm that matches the mapped reads to the reference genome and runs an alignment function thereon.

An exemplary aligning function compares one or more, e.g., all of the reads, to the reference, such as by placing them in a graphical relation to one another, e.g., such as in a table, e.g., a virtual array or matrix, where the sequence of one of the reference genome or the mapped reads is placed on one dimension or axis, e.g., the horizontal axis, and the other is placed on the opposed dimensions or axis, such as the vertical axis. A conceptual scoring wave front is then passed over the array so as to determine the alignment of the reads with the reference genome, such as by computing alignment scores for each cell in the matrix.

The scoring wave front represents one or more, e.g., all, the cells of the matrix, or a portion of those cells, which may be scored independently and/or simultaneously according to the rules of dynamic programming applicable in the alignment algorithm, such as Smith-Waterman, and/or Needleman-Wunsch, and/or related algorithms. For example, taking the origin of the matrix (corresponding to the beginning of the read and/or the beginning of a reference window of the conceptual scoring wave front) to be at the top-left corner, first only the top-left cell at coordinates (0,0) of the matrix may be scored, e.g., a 1-cell wave front; next, the two cells to the right and below at coordinates (0,1) and (1,0) may be scored, e.g., a 2-cell wave front; next the three cells at (0,2), (1,1), and (2,0) may be scored, e.g., a 3-cell wave front. These exemplary wave fronts may then extend diagonally in straight lines from bottom-left to top-right, and the motion of the wave front from step to step is diagonally from top-left to bottom-right through the matrix. Alignment scores may be computed sequentially or in other orders, such as by computing all the scores in the top row from left to right, followed by all the scores in the next row from left to right, etc. In this manner the diagonally sweeping diagonal wave front represents an optimal sequence of batches of scores computed simultaneously or in parallel in a series of wave front steps.

For instance, in one embodiment, a window of the reference genome containing the segment to which a read was mapped is placed on the horizontal axis, and the read is positioned on the vertical axis. In a manner such as this an array or matrix is generated, e.g., a virtual matrix, whereby the nucleotide at each position in the read may be compared with the nucleotide at each position in the reference window. As the wave front passes over the array, all potential ways of aligning the read to the reference window are considered, including if changes to one sequence would be required to make the read match the reference sequence, such as by changing one or more nucleotides of the read to other nucleotides, or inserting one or more new nucleotides into one sequence, or deleting one or more nucleotides from one sequence.

An alignment score, representing the extent of the changes that would be required to be made to achieve an exact alignment, is generated, wherein this score and/or other associated data may be stored in the given cells of the array. Each cell of the array corresponds to the possibility that the nucleotide at its position on the read axis aligns to the nucleotide at its position on the reference axis, and the score generated for each cell represents the partial alignment terminating with the cell's positions in the read and the reference window. The highest score generated in any cell represents the best overall alignment of the read to the reference window. In various instances, the alignment may be global, where the entire read must be aligned to some portion of the reference window, such as using a Needleman-Wunsch or similar algorithm; or in other instances, the alignment may be local, where only a portion of the read may be aligned to a portion of the reference window, such as by using a Smith-Waterman or similar algorithm.

The size of the reference window may be any suitable size. For instance, since a typical read may be from about 100 to about 1,000 nucleotides long, the length of the reference window accordingly, in some instances, may be from about 100 to 1,000 nucleotides long or longer. However, in some instances, the length of the reads may be greater, and/or the length of the reference window can be greater such as about 10,000, 25,000, 50,000, 75,000, 100,000, 200,000 nucleotides long or more. It may be advantageous for the reference window to be padded somewhat longer than the read, such as including 32 or 64 or 128 or 200 or even 500 extra nucleotides in the reference window beyond the extremes of the reference genome segment to which the read was mapped, such as to permit insertions and/or deletions near the ends of the read to be fully evaluated. For instance, if only a portion of the read was mapped to a segment of the reference, extra padding may be applied to the reference window corresponding to the unmapped portions of the read, or longer by some factor, such as 10% or 15% or 20% or 25% or even 50% or more, so as to allow the unmapped portions of the read space to fully align to the reference window. In some instances, however, the length of the reference window may be selected to be shorter than the length of the reads, such as where a long portion of the read is not mapped to the reference, such as more or less than 1000 nucleotides at one end of the read, such as in order to focus the alignment on the mapped portion.

The alignment wave front may be of unlimited length, or limited to any suitable fixed length, or of variable length. For instance, all cells along the entire diagonal line of each wave front step extending fully from one axis to the other axis may be scored. Alternatively, a limited length, such as 64 cells wide, may be scored on each wave front step, such as by tracing a diagonally 64-cell wide band of scored cells through the matrix, and leaving cells outside of this band unscored. In some instances, it may be unnecessary to calculate scores far from a band around the true alignment path, and substantial work may be saved by computing scores only in a limited bandwidth, using a fixed length scoring wave front, as herein described.

Accordingly, in various instances, an alignment function may be performed, such as on the data obtained from the mapping module. Hence, in various instances, an alignment function may form a module, such as an alignment module, that may form part of a system, e.g., a pipeline, that is used, such as in addition with a mapping module, in a process for determining the actual entire genomic sequence, or a portion thereof, of an individual. For instance, the output returned from the performance of the mapping function, such as from a mapping module, e.g., the list of possibilities as to where one or more or all of the reads maps to one or more positions in one or more reference genomes, may be employed by the alignment function so as to determine the actual sequence alignment of the subject's sequenced DNA.

Such an alignment function may at times be useful because, as described above, often times, for a variety of different reasons, the sequenced reads do not always match exactly to the reference genome. For instance, there may be an SNP (single nucleotide polymorphism) in one or more of the reads, e.g., a substitution of one nucleotide for another at a single position; there may be an "indel," insertion or deletion of one or more bases along one or more of the read sequences, which insertion or deletion is not present in the reference genome; and/or there may be a sequencing error (e.g., errors in sample prep and/or sequencer read and/or sequencer output, etc.) causing one or more of these apparent variations. Accordingly, when a read varies from the reference, such as by an SNP or indel, this may be because the reference differs from the true DNA sequence sampled, or because the read differs from the true DNA sequence sampled. The problem is to figure out how to correctly align the reads to the reference genome given the fact that in all likelihood the two sequences are going to vary from one another in a multiplicity of different ways.

Accordingly, in various instances, the input into an alignment function, such as from a mapping function, such as a prefix/suffix tree, or a Burrows/Wheeler transform, or a hash table and/or hash function, may be a list of possibilities as to where one or more reads may match to one or more positions of one or more reference sequences. For instance, for any given read, it may match any number of positions in the reference genome, such as at 1 location or 16, or 32, or 64, or 100, or 500, or 1,000 or more locations where a given read maps to in the genome. However, any individual read was derived, e.g., sequenced, from only one specific portion of the genome. Hence, in order to find the true location from where a given particular read was derived, an alignment function may be performed, e.g., a Smith-Waterman gapped alignment, a Needleman-Wunsch alignment, etc., so as to determine where in the genome one or more of the reads was actually derived, such as by comparing all of the possible locations where a match occurs and determining which of all the possibilities is the most likely location in the genome from which the read was sequenced, on the basis of which location's alignment score is greatest.

As indicated, typically, an algorithm is used to perform such an alignment function. For example, a Smith-Waterman and/or a Needleman-Wunsch alignment algorithm may be employed to align two or more sequences against one another. In this instance, they may be employed in a manner so as to determine the probabilities that for any given position where the read maps to the reference genome that the mapping is in fact the position from where the read originated. Typically these algorithms are configured so as to be performed by software, however, in various instances, such as herein presented, one or more of these algorithms can be configured so as to be executed in hardware, as described in greater detail herein below.

In particular, the alignment function operates, at least in part, to align one or more, e.g., all, of the reads to the reference genome despite the presence of one or more portions of mismatches, e.g., SNPs, insertions, deletions, structural artifacts, etc. so as to determine where the reads are likely to fit in the genome correctly. For instance, the one or more reads are compared against the reference genome, and the best possible fit for the read against the genome is determined, while accounting for substitutions and/or indels and/or structural variants. However, to better determine which of the modified versions of the read best fits against the reference genome, the proposed changes must be accounted for, and as such a scoring function may also be performed.

For instance, a scoring function may be performed, e.g., as part of an overall alignment function, whereby as the alignment module performs its function and introduces one or more changes into a sequence being compared to another, e.g., so as to achieve a better or best fit between the two, for each change that is made so as to achieve the better alignment, a number is detracted from a starting score, e.g., either a perfect score, or a zero starting score, in a manner such that as the alignment is performed the score for the alignment is also determined, such as where matches are detected the score is increased, and for each change introduced a penalty is incurred, and thus, the best fit for the possible alignments can be determined, for example, by figuring out which of all the possible modified reads fits to the genome with the highest score. Accordingly, in various instances, the alignment function may be configured to determine the best combination of changes that need to be made to the read(s) to achieve the highest scoring alignment, which alignment may then be determined to be the correct or most likely alignment.

In view of the above, there are, therefore, at least two goals that may be achieved from performing an alignment function. One is a report of the best alignment, including position in the reference genome and a description of what changes are necessary to make the read match the reference segment at that position, and the other is the alignment quality score. For instance, in various instances, the output from a the alignment module may be a Compact Idiosyncratic Gapped Alignment Report, e.g., a CIGAR string, wherein the CIGAR string output is a report detailing all the changes that were made to the reads so as to achieve their best fit alignment, e.g., detailed alignment instructions indicating how the query actually aligns with the reference. Such a CIGAR string readout may be useful in further stages of processing so as to better determine that for the given subject's genomic nucleotide sequence, the predicted variations as compared against a reference genome are in fact true variations, and not just due to machine, software, or human error.

As set forth above, in various embodiments, alignment is typically performed in a sequential manner, wherein the algorithm receives read sequence data, such as from a mapping module, pertaining to a read and one or more possible locations where the read may potentially map to the one or more reference genomes, and further receives genomic sequence data, such as from one or more memories, pertaining to the one or more positions in the one or more reference genomes to which the read may map. In particular, in various embodiments, the mapping module processes the reads, such as from a FASTQ file, and maps each of them to one or more positions in the reference genome to where they may possibly align. The aligner then takes these predicted positions and uses them to align the reads to the reference genome, such as by building a virtual array by which the reads can be compared with the reference genome.

In performing this function the aligner evaluates each mapped position for each individual read and particularly evaluates those reads that map to multiple possible locations in the reference genome and scores the possibility that each position is the correct position. It then compares the best scores, e.g., the two best scores, and makes a decision as to where the particular read actually aligns. For instance, in comparing the first and second best alignment scores, the aligner looks at the difference between the scores, and if the difference between them is great, then the confidence score that the one with the bigger score is correct will be high. However, where the difference between them is small, e.g., zero, then the confidence score in being able to tell from which of the two positions the read actually is derived is low, and more processing may be useful in being able to clearly determine the true location in the reference genome from where the read is derived. Hence, the aligner in part is looking for the biggest difference between the first and second best confidence scores in making its call that a given read maps to a given location in the reference genome. Ideally, the score of the best possible choice of alignment is significantly greater than the score for the second best alignment for that sequence.

There are many different ways an alignment scoring methodology may be implemented, for instance, each cell of the array may be scored or a sub-portion of cells may be scored, such as in accordance with the methods disclosed herein. Typically, each alignment match, corresponding to a diagonal step in the alignment matrix, contributes a positive score, such as +1, if the corresponding read and reference nucleotides match; and a negative score, such as −4, if the two nucleotides mismatch. Further, each deletion from the reference, corresponding to a horizontal step in the alignment matrix, contributes a negative score, such as −7, and each insertion into the reference, corresponding to a vertical step in the alignment matrix, contributes a negative score, such as −7.

In various instances, scoring parameters for nucleotide matches, nucleotide mismatches, insertions, and deletions may have any various positive or negative or zero values. In various instances, these scoring parameters may be modified based on available information. For instance, in certain instances, alignment gaps (insertions or deletions) are penalized by an affine function of the gap length, for example −7 for the first deleted (resp. inserted) nucleotide, but only −1 for each additional deleted (resp. inserted) nucleotide in continuous sequence. In various implementations, affine gap penalties may be achieved by splitting gap (insertion or deletion) penalties into two components, such as a gap open penalty, e.g. −6, applied to the first step in a gap; and a gap extend penalty, e.g. −1, applied to every or further steps in the gap. Affine gap penalties may yield more accurate alignments, such as by letting alignments containing long insertions or deletions achieve appropriately high scores. Further, each lateral move may have the same or different costs, such as the same cost per step, and/or where gaps occur, such gaps can come at a higher or lower costs, such that the cost for lateral movements of the aligner may be less expensive than the costs for gaps. Accordingly, in various embodiments, affine gap scoring may be implemented, however, this can be expensive in software and/or hardware, because it typically requires a plurality, e.g., 3 scores, for each cell to be scored, and hence, in various embodiments affine gap scoring is not implemented.

In various instances, scoring parameters may also be sensitive to "base quality scores" corresponding to nucleotides in the read. Some sequenced DNA read data, in formats such as FASTQ, may include a base quality score associated with each nucleotide, indicating an estimated probability that the nucleotide is incorrect, e.g. due to a sequencing error. In some read data, base quality scores may indicate the likelihood that an insertion and/or deletion sequencing error is present in or adjacent to each position, or additional quality scores may provide this information separately. More accurate alignments, therefore, may be achieved by making scoring parameters, including any or all of nucleotide match scores, nucleotide mismatch scores, gap (insertion and/or deletion) penalties, gap open penalties, and/or gap extend penalties, vary according to a base quality score associated with the current read nucleotide or position. For example, score bonuses and/or penalties could be made smaller when a base quality score indicates a high probability a sequencing or other error being present. Base quality sensitive scoring may be implemented, for example, using a fixed or configurable lookup-table, accessed using a base quality score, which returns corresponding scoring parameters.

In a hardware implementation in an integrated circuit, such as an FPGA, ASIC or Structured ASIC, a scoring wave front may be implemented as a linear array of scoring cells, such as 16 cells, or 32 cells, or 64 cells, or 128 cells or the like. Each of the scoring cells may be built of digital logic elements in a wired configuration to compute alignment scores. Hence, for each step of the wave front, for instance, each clock cycle, or some other fixed or variable unit of time, each of the scoring cells, or a portion of the cells, computes the score or scores required for a new cell in the virtual alignment matrix. Notionally, the various scoring cells are considered to be in various positions in the alignment matrix, corresponding to a scoring wave front as discussed herein, e.g., along a straight line extending from bottom-left to top-right in the matrix. As is well understood in the field of digital logic design, the physical scoring cells and their comprised digital logic need not be physically arranged in like manner on the integrated circuit.

Accordingly, as the wave front takes steps to sweep through the virtual alignment matrix, the notional positions of the scoring cells correspondingly update each cell, for example, notionally "moving" a step to the right, or for example, a step downward in the alignment matrix. All scoring cells make the same relative notional movement, keeping the diagonal wave front arrangement intact. Each time the wave front moves to a new position, e.g., with a vertical downward step, or a horizontal rightward step in the matrix, the scoring cells arrive in new notional positions, and compute alignment scores for the virtual alignment matrix cells they have entered.

In such an implementation, neighboring scoring cells in the linear array are coupled to communicate query (read) nucleotides, reference nucleotides, and previously calculated alignment scores. The nucleotides of the reference window may be fed sequentially into one end of the wave front, e.g., the top-right scoring cell in the linear array, and may shift from there sequentially down the length of the wave front, so that at any given time, a segment of reference nucleotides equal in length to the number of scoring cells is present within the cells, one successive nucleotide in each successive scoring cell.

Accordingly, each time the wave front steps horizontally, another reference nucleotide is fed into the top-right cell, and other reference nucleotides shift down-left through the wave front. This shifting of reference nucleotides may be the underlying reality of the notional movement of the wave front of scoring cells rightward through the alignment matrix. Hence, the nucleotides of the read may be fed sequentially into the opposite end of the wave front, e.g. the bottom-left scoring cell in the linear array, and shift from there sequentially up the length of the wave front, so that at any given time, a segment of query nucleotides equal in length to the number of scoring cells is present within the cells, one successive nucleotide in each successive scoring cell.

Likewise, each time the wave front steps vertically, another query nucleotide is fed into the bottom-left cell, and other query nucleotides shift up-right through the wave front. This shifting of query nucleotides is the underlying reality of the notional movement of the wave front of scoring cells downward through the alignment matrix. Accordingly, by commanding a shift of reference nucleotides, the wave front may be moved a step horizontally, and by commanding a shift of query nucleotides, the wave front may be moved a step vertically. Accordingly, to produce generally diagonal wave front movement, such as to follow a typical alignment of query and reference sequences without insertions or deletions, wave front steps may be commanded in alternating vertical and horizontal directions.

Accordingly, neighboring scoring cells in the linear array may be coupled to communicate previously calculated alignment scores. In various alignment scoring algorithms, such as a Smith-Waterman or Needleman-Wunsch, or such variant, the alignment score(s) in each cell of the virtual alignment matrix may be calculated using previously calculated scores in other cells of the matrix, such as the three cells positioned immediately to the left of the current cell, above the current cell, and diagonally up-left of the current cell. When a scoring cell calculates new score(s) for another matrix position it has entered, it must retrieve such previously calculated scores corresponding to such other matrix positions. These previously calculated scores may be obtained from storage of previously calculated scores within the same cell, and/or from storage of previously calculated scores in the one or two neighboring scoring cells in the linear array. This is because the three contributing score positions in the virtual alignment matrix (immediately left, above, and diagonally up-left) would have been scored either by the current scoring cell, or by one of its neighboring scoring cells in the linear array.

For instance, the cell immediately to the left in the matrix would have been scored by the current scoring cell, if the most recent wave front step was horizontal (rightward), or would have been scored by the neighboring cell down-left in the linear array, if the most recent wave front step was vertical (downward). Similarly, the cell immediately above in the matrix would have been scored by the current scoring cell, if the most recent wave front step was vertical (downward), or would have been scored by the neighboring cell up-right in the linear array, if the most recent wave front step was horizontal (rightward). Similarly, the cell diagonally up-left in the matrix would have been scored by the current scoring cell, if the most recent two wave front steps were in different directions, e.g., down then right, or right then down, or would have been scored by the neighboring cell up-right in the linear array, if the most recent two wave front steps were both horizontal (rightward), or would have been scored by the neighboring cell down-left in the linear array, if the most recent two wave front steps were both vertical (downward).

Accordingly, by considering information on the last one or two wave front step directions, a scoring cell may select the appropriate previously calculated scores, accessing them within itself, and/or within neighboring scoring cells, utilizing the coupling between neighboring cells. In a variation, scoring cells at the two ends of the wave front may have their outward score inputs hard-wired to invalid, or zero, or minimum-value scores, so that they will not affect new score calculations in these extreme cells.

A wave front being thus implemented in a linear array of scoring cells, with such coupling for shifting reference and query nucleotides through the array in opposing directions, in order to notionally move the wave front in vertical and horizontal steps, and coupling for accessing scores previously computed by neighboring cells in order to compute alignment score(s) in new virtual matrix cell positions entered by the wave front, it is accordingly possible to score a band of cells in the virtual matrix, the width of the wave front, such as by commanding successive steps of the wave front to sweep it through the matrix. For a new read and reference window to be aligned, therefore, the wave front may begin positioned inside the scoring matrix or, advantageously, may gradually enter the scoring matrix from outside, beginning e.g., to the left, or above, or diagonally left and above the top-left corner of the matrix.

For instance, the wave front may begin with its top-left scoring cell positioned just left of the top-left cell of the virtual matrix, and the wave front may then sweep rightward into the matrix by a series of horizontal steps, scoring a horizontal band of cells in the top-left region of the matrix. When the wave front reaches a predicted alignment relationship between the reference and query, or when matching is detected from increasing alignment scores, the wave front may begin to sweep diagonally down-right, by alternating vertical and horizontal steps, scoring a diagonal band of cells through the middle of the matrix. When the bottom-left wave front scoring cell reaches the bottom of the alignment matrix, the wave front may begin sweeping rightward again by successive horizontal steps, until some or all wave front cells sweep out of the boundaries of the alignment matrix, scoring a horizontal band of cells in the bottom-right region of the matrix.

In a variation, increased efficiency may be obtained from the alignment wave front by sharing its scoring cells between two successive alignment operations. A next alignment matrix having been established in advance, as the top-right portion of the wave front exits the bottom-right region of the current alignment matrix, it may enter, immediately, or after crossing a minimum gap such as one cell or three cells, the top-right region of the next alignment matrix. In this manner, the horizontal wave front sweep out of one alignment matrix can be the same motion as the horizontal wave front sweep into the next alignment matrix. Doing this may include the reference and query bases of the next alignment to be fed into those scoring cells crossing into the next alignment matrix, and can reduce the average time consumed per alignment by the time to execute a number of wave front steps almost equal to the number of alignment cells in the wave front, e.g., such as 64 or 63 or 61 steps, which may take e.g. 64 or 63 or 61 clock cycles.

The number of scoring cells in an implementation of an alignment wave front may be selected to balance various factors, including alignment accuracy, maximum insertion and deletion length, area, cost, and power consumption of the digital logic, clock frequency of the aligner logic, and performance of the overall integrated circuit. A long wave front is desirable for good alignment accuracy, especially because a wave front of N cells can align across indels approximately N nucleotides long, or slightly shorter. But a longer wave front costs more logic, which consumes more power. Further, a longer wave front can increase wire routing complexity and delays on the integrated circuit, leading to lower maximum clock frequencies, reducing net aligner performance. Further still, if an integrated circuit has a limited size or power consumption, using a longer wave front may require less logic to be implemented on the IC elsewhere, such as replicating fewer entire wave fronts, or other aligner or mapper logic components, this decreasing net performance of the IC. In one particular embodiment, 64 scoring cells in the wave front may give an acceptable balance of these factors.

Accordingly, where the wave front is X, e.g., 64 scoring cells wide, the scored band in the alignment matrix will likewise be 64 cells wide (measured diagonally). The matrix cells outside of this band do not necessarily need to be processed nor their scores calculated, provided that the optimal (best-scoring) alignment path through the matrix stays within the scored band. In a relatively small matrix, therefore, used to align relatively short reads, e.g., 100 nucleotide or 250 nucleotide reads, this may be a safe assumption, such as if the wave front sweeps a perfect diagonal along the predicted aligned position of the read.

However, in some instances, such as in a large alignment matrix used to align long reads, e.g., 1000 or 10,000 or 100,000 nucleotides, there may be a substantial risk of accumulated indels causing the true alignment to deviate from a perfect diagonal, sufficiently far in aggregate that it may escape the scored band. In such instances, it may be useful to steer the wave front so that the highest set of scores will be near the center of the wave front. Consequently, as the wave front performs its sweep, if the highest scores start to move one way or the other, e.g., left to right, the wave front is shifted over to track this move. For instance, if the highest scores are observed in scoring cells substantially up-right from the center of the wave front, the wave front may be steered some distance straight rightward by successive horizontal steps, until the highest scores return near the center of the wave front.

Accordingly, an automatic steering mechanism may be implemented in the wave front control logic, to determine a steering target position within the length of the wave front, based on current and past scores observed in the wave front scoring cells, and to steer the wave front toward this target if it is off-center. More particularly, the position of the maximum score in the most recently scored wave front position may be used as a steering target. This is an effective method in some instances. In some instances, however, the maximum score position may be a poor steering target. For instance, with some combinations of alignment scoring parameters, when a long indel commences, and scores accordingly begin to decline, a pattern of two higher-score peaks with a lower-score valley between them can form along the wave front, the two peaks drifting apart as the indel continues.

Because it cannot be easily determined whether the event in progress is an insertion or a deletion, it is important for the wave front to track diagonally until successful matching commences again, either some distance to the right for a deletion, or some distance downward for an insertion. But if two spreading score peaks form, one of them is likely to be slightly higher than the other, and could pull the automatic steering in that direction, causing the wave front to lose the alignment if the actual indel was in the other direction. A more robust method, therefore, may be to subtract a delta value from the maximum observed wave front score to determine a threshold score, identify the two extreme scoring cells at least equal to this threshold score, and use the midpoint between these extreme cells as the steering target. This will tend to guide diagonally between a two-peak score pattern. Other steering criteria can readily be applied, however, which serve to keep higher scores near the center of the wave front. If there is a delayed reaction between obtaining scores from wave front scoring cells and making a corresponding steering decision, hysteresis can advantageously be applied to compensate for steering decisions made in the intervening time, to avoid oscillating patterns of automatic wave front steering.

One or more of such alignment procedures may be performed by any suitable alignment algorithm, such as a Needleman-Wunsch alignment algorithm and/or a Smith-Waterman alignment algorithm that may have been modified to accommodate the functionality herein described. In general both of these algorithms and those like them basically perform, in some instances, in a similar manner. For instance, as set forth above, these alignment algorithms typically build the virtual array in a similar manner such that, in various instances, the horizontal top boundary may be configured to represent the genomic reference sequence, which may be laid out across the top row of the array according to its base pair composition. Likewise, the vertical boundary may be configured to represent the sequenced and mapped query sequences that have been positioned in order, downwards along the first column, such that their nucleotide sequence order is generally matched to the nucleotide sequence of the reference to which they mapped. The intervening cells may then be populated with scores as to the probability that the relevant base of the query at a given position, is positioned at that location relative to the reference. In performing this function, a swath may be moved diagonally across the matrix populating scores within the intervening cells and the probability for each base of the query being in the indicated position may be determined.

With respect to a Needleman-Wunsch alignment function, which generates optimal global (or semi-global) alignments, aligning the entire read sequence to some segment of the reference genome, the wave front steering may be configured such that it typically sweeps all the way from the top edge of the alignment matrix to the bottom edge. When the wave front sweep is complete, the maximum score on the bottom edge of the alignment matrix (corresponding to the end of the read) is selected, and the alignment is back-traced to a cell on the top edge of the matrix (corresponding to the beginning of the read). In various of the instances disclosed herein, the reads can be any length long, can be any size, and there need not be extensive read parameters as to how the alignment is performed, e.g., in various instances, the read can be as long as a chromosome. In such an instance, however, the memory size and chromosome length may be limiting factor.

With respect to a Smith-Waterman algorithm, which generates optimal local alignments, aligning the entire read sequence or part of the read sequence to some segment of the reference genome, this algorithm may be configured for finding the best scoring possible based on a full or partial alignment of the read. Hence, in various instances, the wave front-scored band may not extend to the top and/or bottom edges of the alignment matrix, such as if a very long read had only seeds in its middle mapping to the reference genome, but commonly the wave front may still score from top to bottom of the matrix. Local alignment is typically achieved by two adjustments. First, alignment scores are never allowed to fall below zero (or some other floor), and if a cell score otherwise calculated would be negative, a zero score is substituted, representing the start of a new alignment. Second, the maximum alignment score produced in any cell in the matrix, not necessarily along the bottom edge, is used as the terminus of the alignment. The alignment is backtraced from this maximum score up and left through the matrix to a zero score, which is used as the start position of the local alignment, even if it is not on the top row of the matrix.

In view of the above, there are several different possible pathways through the virtual array. In various embodiments, the wave front starts from the upper left corner of the virtual array, and moves downwards towards identifiers of the maximum score. For instance, the results of all possible aligns can be gathered, processed, correlated, and scored to determine the maximum score. When the end of a boundary or the end of the array has been reached and/or a computation leading to the highest score for all of the processed cells is determined (e.g., the overall highest score identified) then a backtrace may be performed so as to find the pathway that was taken to achieve that highest score.

For example, a pathway that leads to a predicted maximum score may be identified, and once identified an audit may be performed so as to determine how that maximum score was derived, for instance, by moving backwards following the best score alignment arrows retracing the pathway that led to achieving the identified maximum score, such as calculated by the wave front scoring cells. This backwards reconstruction or backtrace involves starting from a determined maximum score, and working backward through the previous cells navigating the path of cells having the scores that led to achieving the maximum score all the way up the table and back to an initial boundary, such as the beginning of the array, or a zero score in the case of local alignment.

During a backtrace, having reached a particular cell in the alignment matrix, the next backtrace step is to the neighboring cell, immediately leftward, or above, or diagonally up-left, which contributed the best score that was selected to construct the score in the current cell. In this manner, the evolution of the maximum score may be determined, thereby figuring out how the maximum score was achieved. The backtrace may end at a corner, or an edge, or a boundary, or may end at a zero score, such as in the upper left hand corner of the array. Accordingly, it is such a back trace that identifies the proper alignment and thereby produces the CIGAR strand readout, e.g., 3M, 2D, 8M, 41, 16M, etc., that represents how the sample genomic sequence derived from the individual, or a portion thereof, matches to, or otherwise aligns with, the genomic sequence of the reference DNA.

Accordingly, once it has been determined where each read is mapped, and further determined where each read is aligned, e.g., each relevant read has been given a position and a quality score reflecting the probability that the position is the correct alignment, such that the nucleotide sequence for the subject's DNA is known, then the order of the various reads and/or genomic nucleic acid sequence of the subject may be verified, such as by performing a back trace function moving backwards up through the array so as to determine the identity of every nucleic acid in its proper order in the sample genomic sequence. Consequently, in some aspects, the present disclosure is directed to a back trace function, such as is part of an alignment module that performs both an alignment and a back trace function, such as a module that may be part of a pipeline of modules, such as a pipeline that is directed at taking raw sequence read data, such as form a genomic sample form an individual, and mapping and/or aligning that data, which data may then be sorted.

To facilitate the backtrace operation, it is useful to store a scoring vector for each scored cell in the alignment matrix, encoding the score-selection decision. For classical Smith-Waterman and/or Needleman-Wunsch scoring with linear gap penalties, the scoring vector can encode four possibilities, which may optionally be stored as a 2-bit integer from 0 to 3, for example: 0=new alignment (null score selected); 1=vertical alignment (score from the cell above selected, modified by gap penalty); 2=horizontal alignment (score from the cell to the left selected, modified by gap penalty); 3=diagonal alignment (score from the cell up and left selected, modified by nucleotide match or mismatch score). Optionally, the computed score(s) for each scored matrix cell may also be stored (in addition to the maximum achieved alignment score which is standardly stored), but this is not generally necessary for backtrace, and can consume large amounts of memory. Performing backtrace then becomes a matter of following the scoring vectors; when the backtrace has reached a given cell in the matrix, the next backtrace step is determined by the stored scoring vector for that cell, e.g.: 0=terminate backtrace; 1=backtrace upward; 2=backtrace leftward; 3=backtrace diagonally up-left.

Such scoring vectors may be stored in a two-dimensional table arranged according to the dimensions of the alignment matrix, wherein only entries corresponding to cells scored by the wave front are populated. Alternatively, to conserve memory, more easily record scoring vectors as they are generated, and more easily accommodate alignment matrices of various sizes, scoring vectors may be stored in a table with each row sized to store scoring vectors from a single wave front of scoring cells, e.g. 128 bits to store 64 2-bit scoring vectors from a 64-cell wave front, and a number of rows equal to the maximum number of wave front steps in an alignment operation.

Additionally, for this option, a record may be kept of the directions of the various wavefront steps, e.g., storing an extra, e.g., 129.sup.th, bit in each table row, encoding e.g., 0 for vertical wavefront step preceding this wavefront position, and 1 for horizontal wavefront step preceding this wavefront position. This extra bit can be used during backtrace to keep track of which virtual scoring matrix positions the scoring vectors in each table row correspond to, so that the proper scoring vector can be retrieved after each successive backtrace step. When a backtrace step is vertical or horizontal, the next scoring vector should be retrieved from the previous table row, but when a backtrace step is diagonal, the next scoring vector should be retrieved from two rows previous, because the wavefront had to take two steps to move from scoring any one cell to scoring the cell diagonally right-down from it.

In the case of affine gap scoring, scoring vector information may be extended, e.g. to 4 bits per scored cell. In addition to the e.g. 2-bit score-choice direction indicator, two 1-bit flags may be added, a vertical extend flag, and a horizontal extend flag. According to the methods of affine gap scoring extensions to Smith-Waterman or Needleman-Wunsch or similar alignment algorithms, for each cell, in addition to the primary alignment score representing the best-scoring alignment terminating in that cell, a 'vertical score' should be generated, corresponding to the maximum alignment score reaching that cell with a final vertical step, and a 'horizontal score' should be generated, corresponding to the maximum alignment score reaching that cell with a final horizontal step; and when computing any of the three scores, a vertical step into the cell may be computed either using the primary score from the cell above minus a gap-open penalty, or using the vertical score from the cell above minus a gap-extend penalty, whichever is greater; and a horizontal step into the cell may be computed either using the primary score from the cell to the left minus a gap-open penalty, or using the horizontal score from the cell to the left minus a gap-extend penalty, whichever is greater. In cases where the vertical score minus a gap extend penalty is selected, the vertical extend flag in the scoring vector should be set, e.g. '1', and otherwise it should be unset, e.g. '0'. In cases when the horizontal score minus a gap extend penalty is selected, the horizontal extend flag in the scoring vector should be set, e.g. '1', and otherwise it should be unset, e.g. '0'. During backtrace for affine gap scoring, any time backtrace takes a vertical step upward from a given cell, if that cell's scoring vector's vertical extend flag is set, the following backtrace step must also be vertical, regardless of the scoring vector for the cell above. Likewise, any time backtrace takes a horizontal step leftward from a given cell, if that cell's scoring vector's horizontal extend flag is set, the following backtrace step must also be horizontal, regardless of the scoring vector for the cell to the left.

Accordingly, such a table of scoring vectors, e.g. 129 bits per row for 64 cells using linear gap scoring, or 257 bits per row for 64 cells using affine gap scoring, with some number NR of rows, is adequate to support backtrace after concluding alignment scoring where the scoring wavefront took NR steps or fewer. For example, when aligning 300-nucleotide reads, the number of wavefront steps required may always be less than 1024, so the table may be 257.times.1024 bits, or approximately 32 kilobytes, which in many cases may be a reasonable local memory inside the IC. But if very long reads are to be aligned, e.g. 100,000 nucleotides, the memory requirements for scoring vectors may be quite large, e.g. 8 megabytes, which may be very costly to include as local memory inside the IC. For such support, scoring vector information may be recorded to bulk memory outside the IC, e.g. DRAM, but then the bandwidth requirements, e.g. 257 bits per clock cycle per aligner module, may be excessive, which may bottleneck and dramatically reduce aligner performance.

Accordingly, it is desirable to have a method for disposing of scoring vectors before completing alignment, so their storage requirements can be kept bounded, e.g. to perform incremental backtraces, generating incremental partial CIGAR strings for example, from early portions of an alignment's scoring vector history, so that such early portions of the scoring vectors may then be discarded. The challenge is that the backtrace is supposed to begin in the alignment's terminal, maximum scoring cell, which unknown until the alignment scoring completes, so any backtrace begun before alignment completes may begin from the wrong cell, not along the eventual final optimal alignment path.

Accordingly, a method is given for performing incremental backtrace from partial alignment information, e.g. comprising partial scoring vector information for alignment matrix cells scored so far. From a currently completed alignment boundary, e.g., a particular scored wave front position, backtrace is initiated from all cell positions on the boundary. Such backtrace from all boundary cells may be performed sequentially, or advantageously, especially in a hardware implementation, all the backtraces may be performed together. It is not necessary to extract alignment notations, e.g., CIGAR strings, from these multiple backtraces; only to determine what alignment matrix positions they pass through during the backtrace. In an implementation of simultaneous backtrace from a scoring boundary, a number of 1-bit registers may be utilized, corresponding to the number of alignment cells, initialized e.g., all to '1' s, representing whether any of the backtraces pass through a corresponding position. For each step of simultaneous backtrace, scoring vectors corresponding to all the current '1' s in these registers, e.g. from one row of the scoring vector table, can be examined, to determine a next backtrace step corresponding to each '1' in the registers, leading to a following position for each '1' in the registers, for the next simultaneous backtrace step.

Importantly, it is easily possible for multiple '1' s in the registers to merge into common positions, corresponding to multiple of the simultaneous backtraces merging together onto common backtrace paths. Once two or more of the simultaneous backtraces merge together, they remain merged indefinitely, because henceforth they will utilize scoring vector information from the same cell. It has been observed, empirically and for theoretical reasons, that with high probability, all of the simultaneous backtraces merge into a singular backtrace path, in a relatively small number of backtrace steps, which e.g. may be a small multiple, e.g. 8, times the number of scoring cells in the wavefront. For example, with a 64-cell wavefront, with high probability, all backtraces from a given wavefront boundary merge into a single backtrace path within 512 backtrace steps. Alternatively, it is also possible, and not uncommon, for all backtraces to terminate within the number, e.g. 512, of backtrace steps.

Accordingly, the multiple simultaneous backtraces may be performed from a scoring boundary, e.g. a scored wavefront position, far enough back that they all either terminate or merge into a single backtrace path, e.g. in 512 backtrace steps or fewer. If they all merge together into a singular backtrace path, then from the location in the scoring matrix where they merge, or any distance further back along the singular backtrace path, an incremental backtrace from partial alignment information is possible. Further backtrace from the merge point, or any distance further back, is commenced, by normal singular backtrace methods, including recording the corresponding alignment notation, e.g., a partial CIGAR string. This incremental backtrace, and e.g. partial CIGAR string, must be part of any possible final backtrace, and e.g. full CIGAR string, that would result after alignment completes, unless such final backtrace would terminate before reaching the scoring boundary where simultaneous backtrace began, because if it reaches the scoring boundary, it must follow one of the simultaneous backtrace paths, and merge into the singular backtrace path, now incrementally extracted.

Therefore, all scoring vectors for the matrix regions corresponding to the incrementally extracted backtrace, e.g., in all table rows for wave front positions preceding the start of the extracted singular backtrace, may be safely discarded. When the final backtrace is performed from a maximum scoring cell, if it terminates before reaching the scoring boundary (or alternatively, if it terminates before reaching the start of the extracted singular backtrace), the incremental alignment notation, e.g. partial CIGAR string, may be discarded. If the final backtrace continues to the start of the extracted singular backtrace, its alignment notation, e.g., CIGAR string, may then be grafted onto the incremental alignment notation, e.g., partial CIGAR string.

Furthermore, in a very long alignment, the process of performing a simultaneous backtrace from a scoring boundary, e.g., scored wave front position, until all backtraces terminate or merge, followed by a singular backtrace with alignment notation extraction, may be repeated multiple times, from various successive scoring boundaries. The incremental alignment notation, e.g. partial CIGAR string, from each successive incremental backtrace may then be grafted onto the accumulated previous alignment notations, unless the new simultaneous backtrace or singular backtrace terminates early, in which case accumulated previous alignment notations may be discarded. The eventual final backtrace likewise grafts its alignment notation onto the most recent accumulated alignment notations, for a complete backtrace description, e.g. CIGAR string.

Accordingly, in this manner, the memory to store scoring vectors may be kept bounded, assuming simultaneous backtraces always merge together in a bounded number of steps, e.g. 512 steps. In rare cases where simultaneous backtraces fail to merge or terminate in the bounded number of steps, various exceptional actions may be taken, including failing the current alignment, or repeating it with a higher bound or with no bound, perhaps by a different or traditional method, such as storing all scoring vectors for the complete alignment, such as in external DRAM. In a variation, it may be reasonable to fail such an alignment, because it is extremely rare, and even rarer that such a failed alignment would have been a best-scoring alignment to be used in alignment reporting.

In an optional variation, scoring vector storage may be divided, physically or logically, into a number of distinct blocks, e.g. 512 rows each, and the final row in each block may be used as a scoring boundary to commence a simultaneous backtrace. Optionally, a simultaneous backtrace may be required to terminate or merge within the single block, e.g. 512 steps. Optionally, if simultaneous backtraces merge in fewer steps, the merged backtrace may nevertheless be continued through the whole block, before commencing an extraction of a singular backtrace in the previous block. Accordingly, after scoring vectors are fully written to block N, and begin writing to block N+1, a simultaneous backtrace may commence in block N, followed by a singular backtrace and alignment notation extraction in block N−1. If the speed of the simultaneous backtrace, the singular backtrace, and alignment scoring are all similar or identical, and can be performed simultaneously, e.g., in parallel hardware in an IC, then the singular backtrace in block N−1 may be simultaneous with scoring vectors filling block N+2, and when block N+3 is to be filled, block N−1 may be released and recycled.

Thus, in such an implementation, a minimum of 4 scoring vector blocks may be employed, and may be utilized cyclically. Hence, the total scoring vector storage for an aligner module may be 4 blocks of 257×512 bits each, for example, or approximately 64 kilobytes. In a variation, if the current maximum alignment score corresponds to an earlier block than the current wavefront position, this block and the previous block may be preserved rather than recycled, so that a final backtrace may commence from this position if it remains the maximum score; having an extra 2 blocks to keep preserved in this manner brings the minimum, e.g., to 6 blocks. In another variation, to support overlapped alignments, the scoring wave front crossing gradually from one alignment matrix to the next as described above, additional blocks, e.g. 1 or 2 additional blocks, may be utilized, e.g., 8 blocks total, e.g., approximately 128 kilobytes. Accordingly, if such a limited number of blocks, e.g., 4 blocks or 8 blocks, is used cyclically, alignment and backtrace of arbitrarily long reads is possible, e.g., 100,000 nucleotides, or an entire chromosome, without the use of external memory for scoring vectors.

It is to be understood, such as with reference to the above, that although a mapping function may in some instances have been described, such as with reference to a mapper, and/or an alignment function may have in some instances been described, such as with reference to an aligner, these different functions may be performed sequentially by the same architecture, which has commonly been referenced in the art as an aligner. Accordingly, in various instances, both the mapping function and the aligning function, as herein described may be performed by a common architecture that may be understood to be an aligner, especially in those instances wherein to perform an alignment function, a mapping function need first be performed.

The output from the alignment module is a SAM (Text) or BAM (e.g., binary version of a SAM) file along with a mapping quality score (MAPA), which quality score reflects the confidence that the predicted and aligned location of the read to the reference is actually where the read is derived. Accordingly, once it has been determined where each read is mapped, and further determined where each read is aligned, e.g., each relevant read has been given a position and a quality score reflecting the probability that the position is the correct alignment, such that the nucleotide sequence for the subject's DNA is known as well as how the subject's DNA differs from that of the reference (e.g., the CIGAR string has been determined), then the various reads representing the genomic nucleic acid sequence of the subject may be sorted by chromosome location, so that the exact location of the read on the chromosomes may be determined. Consequently, in some aspects, the present disclosure is directed to a sorting function, such as may be performed by a sorting module, which sorting module may be part of a pipeline of modules, such as a pipeline that is directed at taking raw sequence read data, such as form a genomic sample form an individual, and mapping and/or aligning that data, which data may then be sorted.

More particularly, once the reads have been assigned a position, such as relative to the reference genome, which may include identifying to which chromosome the read belongs and/or its offset from the beginning of that chromosome, the reads may be sorted by position. Sorting may be useful, such as in downstream analyses, whereby all of the reads that overlap a given position in the genome may be formed into a pile up so as to be adjacent to one another, such as after being processed through the sorting module, whereby it can be readily determined if the majority of the reads agree with the reference value or not. Hence, where the majority of reads do not agree with the reference value a variant call can be flagged. Sorting, therefore, may involve one or more of sorting the reads that align to the relatively same position, such as the same chromosome position, so as to produce a pileup, such that all the reads that cover the same location are physically grouped together; and may further involve analyzing the reads of the pileup to determine where the reads may indicate an actual variant in the genome, as compared to the reference genome, which variant may be distinguishable, such as by the consensus of the pileup, from an error, such as a machine read error or error an error in the sequencing methods which may be exhibited by a small minority of the reads.

Once the data has been obtained there are one or more other modules that may be run so as to clean up the data. For instance, one module that may be included, for example, in a sequence analysis pipeline, such as for determining the genomic sequence of an individual, may be a local realignment module. For example, it is often difficult to determine insertions and deletions that occur at the end of the read. This is because the Smith-Waterman or equivalent alignment process lacks enough context beyond the indel to allow the scoring to detect its presence. Consequently, the actual indel may be reported as one or more SNPs. In such an instance, the accuracy of the predicted location for any given read may be enhanced by performing a local realignment on the mapped and/or aligned and/or sorted read data.

In such instances, pileups may be used to help clarify the proper alignment, such as where a position in question is at the end of any given read, that same position is likely to be at the middle of some other read in the pileup. Accordingly, in performing a local realignment the various reads in a pileup may be analyzed so as to determine if some of the reads in the pile up indicate that there was an insertion or a deletion at a given position where an other read does not include the indel, or rather includes a substitution, at that position, then the indel may be inserted, such as into the reference, where it is not present, and the reads in the local pileup that overlap that region may be realigned to see if collectively a better score is achieved then when the insertion and/or deletion was not there. Accordingly, if there is an improvement, the whole set of reads in the pileup may be reviewed and if the score of the overall set has improved then it is clear to make the call that there really was an indel at that position. In a manner such as this, the fact that there is not enough context to more accurately align a read at the end of a chromosome, for any individual read, may be compensated for. Hence, when performing a local realignment, one or more pileups where one or more indels may be positioned are examined, and it is determined if by adding an indel at any given position the overall alignment score may be enhanced.

Another module that may be included, for example, in a sequence analysis pipeline, such as for determining the genomic sequence of an individual, may be a duplicate marking module. For instance, a duplicate marking function may be performed so as to compensate for chemistry errors that may occur during the sequencing phase. For example, as described above, during some sequencing procedures nucleic acid sequences are attached to beads and built up from there using labeled nucleotide bases. Ideally there will be only one read per bead. However, sometimes multiple reads become attached to a single bead and this results in an excessive number of copies of the attached read. This phenomenon is known as read duplication.

Such read duplication may throw off the statistics and create a statistical bias because instead of having an equal representation of all reads, various reads have been duplicated, such as because of the duplicate template sequences attached to more than one bead are over represented. Accordingly, these may be determined because any read that aligns to the exact same position, and has the exact same length, is likely a duplicate. Once this is identified by the system, only one read need be subjected to further processing and the others may be marked as duplicates and, therefore, can be discarded or ignored. A typical situation where this occurs is where there is not enough genetic material to process from the very beginning and the system attempts to overcompensate for that.

Another module that may be included, for example, in a sequence analysis pipeline, such as for determining the genomic sequence of an individual, may be a base quality score recalibrater. For instance, every base of every read has a Phred score that indicates the probability that the called base at that position is incorrect. For example, the Phred score for any base is due in part to the nature of the base that precedes it and the error profile will be different depending on which base precedes the base in question. Further, there is a greater likelihood of an error occurring at the ends of a read, e.g., such as where at the ends of the reads the chemistry is starting to lose its performance. A base quality score recalibration is a covariant analysis that may go back and measures the empirical quality of the base quality score as a function of all those things by which it varies.

In various instances, it involves two passes, the first gathers all the actual, empirical measured data and statistics on the error rate observed as a function of all the variables, and the second pass involves the actual recalibration of the scores by flowing all the reads through a filter modifying the quality scores for every single base as a function of the variables based on what was actually empirically measured in the data set. This compensates for all the differences in the data due to the various variables and cleans up that data and score. The purpose of all this cleanup is to ensure the best possible variant calling is achieved. Many variant callers base their decisions in part on the reported quality of each of the nucleotides that pile up at each position in the genome. If the quality scores are not accurate, there could easily result a wrong call.

Another module that may be included, for example, in a sequence analysis pipeline, such as for determining the genomic sequence of an individual, may be a compression module, that executes a compression function. As indicated above, it may be useful at some point to take the generated and processed data and transmit it to a remote location, such as the cloud, and hence, the data may need to be compressed at a particular stage of processing, whereby once compressed it may be transmitted and/or otherwise uploaded, such as on to the cloud or to a server farm, etc., for instance, for the performance of the variant calling module. The results once obtained may then be decompressed and/or stored in the memory, on a data base on the cloud, such as an electronic health and/or research database, and the like, which in turn, can be made available for tertiary processing, etc.

Accordingly, as set forth herein above, in various aspects, this present disclosure is directed to systems, apparatuses, and methods for implementing genomics and/or bioinformatic protocols such as, in various instances, for performing one or more functions for analyzing genetic data on an integrated circuit, such as implemented in a hardware processing platform. For example, in one aspect, a bioinformatics system is provided, wherein the system may involve the performance of various bioanalytical functions that have been optimized so as to be performed faster and/or with increased accuracy in a hardware implementation. Accordingly, in various instances, the methods and systems herein described may include the performance of one or more algorithms for executing these functions, wherein the algorithms may be implemented in a hardware solution, such as where the algorithm has been optimized so as to be implemented by an integrated circuit formed of one or more hardwired digital logic circuits. In such an instance, the hardwired digital logic circuits may be interconnected, such as by one or a plurality of physical electrical interconnects, and may be arranged to function as one or more processing engines. In various instances, a plurality of hardwired digital logic circuits are provided, which hardwired digital logic circuits are configured as a set of processing engines, wherein each processing engine is capable of performing one or more steps in the bioinformatics genetic analysis protocol.

More particularly, in one instance, a system for executing a sequence analysis pipeline such as on genetic sequence data is provided. The system may include one or more of an electronic data source, a memory, and an integrated circuit. For instance, in one embodiment, an electronic data source is included, where in the electronic data source may be configured for providing one or more digital signals, such as a digital signal representing one or more reads of genetic data, for example, where each read of genomic data includes a sequence of nucleotides. Further, the memory may be configured for storing one or more genetic reference sequences, and may further be configured for storing an index, such as an index of the one or more genetic reference sequences.

Further still, in various instances, one or more of the plurality of physical electrical interconnects may include an input, such as to the integrated circuit, and may further be connected with the electronic data source, so as to be able to receive the one or more reads of genomic data. In various embodiments, the hardwired digital logic circuits may be arranged as a set of processing engines, such as where each processing engine is formed of a subset of the hardwired digital logic circuits, and is configured so as to perform one or more steps in the sequence analysis pipeline, such as on digitized genetic data, e.g., on the plurality of reads of genomic data. In such instances, each subset of the hardwired digital logic circuits may be in a wired configuration so as to perform the one or more steps in the sequence analysis pipeline, such as where the one or more steps may include performing one or more of: a base calling and/or error correction operation, such as on the digitized genetic data, and/or may include one or more of performing a mapping, an alignment, and/or a sorting function on the genetic data. In certain instances, the pipeline may include performing one or more of a realignment, a deduplication, a base quality score recalibration, a reduction and/or compression, and/or a decompression on the digitized genetic data. In certain instances the pipeline may include performing a variant calling operation on the genetic data.

Accordingly, in various embodiments, the systems, apparatuses, and methods for implementing genomics and/or bioinformatic protocols, as herein described, may involve taking processes that may have typically been performed on software, and embedding those functions into an integrated circuit, such as on a chip, for instance as part of a circuit board, such as where the functions have been optimized to enhance its performance on the chip. Hence, in one embodiment, as can be seen with respect to FIG. 1 a chip is provided wherein the chip has been designed so as to efficiently perform the functions of the pipeline. In various particular embodiments the chip may be a field programmable gate array (FPGA), an application specific integrated circuit (ASIC), or a structured application specific integrated circuit (sASIC), or the like.

For instance, the functioning of one or more of these algorithms may be embedded onto a chip, such as into an FPGA or ASIC or structured ASIC chip, and may be optimized so as to perform more efficiently because of their implementation in such hardware. Accordingly, in one embodiment a FPGA chip is provided wherein the chip is capable of being configurable, e.g., its programming may be changed, so as to be more adaptable in meeting a given user's needs with respect to performing the various genomic functions detailed herein. In such an instance, the user can change and/or modify the algorithms employed dependent on the key parameters desired to be emphasized in the overall system, such as to give additional functionality or change out what was first presented on the chip, e.g., such as re-configuring the chip to employ a different algorithm. Further, in another embodiment a structured ASIC chip is provided wherein the chip is capable of being configurable such as to a limited extent, e.g., some of its programming may be changed, so as to be more adaptable in meeting a given user's needs with respect to performing the various genomic functions detailed herein. In accordance with another embodiment an ASIC is provided, such as where the FPGA or sASIC is converted to an ASIC chip where its functionality may be locked down into the chip. In such an instance, various parameters, such as various parameters regarding the function of one or more of the algorithms set forth herein, may be user selected, for instance, governing how the various modules are supposed to function, but the way those modules actually function is locked in.

In various embodiments, as seen with respect to FIG. 1, the chip may be part of a circuit board, such as part of an expansion card, for instance, a peripheral component interconnect (PCI) card, including a PCIe card, which in various embodiments may be associated, such as, communicably coupled, e.g., electrically connected, with an automated sequencer device so as to function part and parcel with the sequencer, such as where the data files, e.g., FASTQ files, generated by the sequencer is transferred directly over to the chip, such as for secondary genomic processing, such as immediately subsequent to the FASTQ file generation and/or primary processing, e.g., immediately after the sequencing function has been performed.

Accordingly, in certain instances, a PCI card is provided wherein the PCI card may include a chip with a PCIe bus, where the chip may include one or more of: a configuration manager, such as a configuration control (Cent-Com); a direct memory access engine (e.g., a driver); an API; a client level interface (CLI), a library; a memory, such as a random access memory (RAM) or a dynamic random access memory (DRAM); and/or a chip level interconnect, such as a DDR3. For instance, in various instances a configuration manager may be included wherein the configuration manager is driven, such as by a parameter file. In such an instance the configuration manager may be adapted so as to configure the various modules of the pipeline. In various instances, it may be user editable, and thereby allow a user to determine which modules of the pipeline are going to be used, e.g., from all of them to a subset of less than all of them, such as for a particular dataset, such as a particular set of FASTQ files.

For example, in various embodiments, the functioning of the pipeline is very configurable such that one or more of the modules, such as structured into the chip, may be run or not run, as desired. Further, each module in use can also be configured so as to run in accordance with one or more preselected parameters, which the user may have control over, such as regarding how the module is going to perform and behave. Hence, there may be two different sets of configuration files, such as one that controls the basic operations of the system as a whole, and may be hidden from the user, and another that is capable of being manipulated by the user, thereby allowing the user to select various of the parameters by which one or more of the subsystems, e.g., modules, of the chip will be run.

Further still, various of the above described modules may be hardwired into the chip, or may be external to the chip, but positioned in a coupling relationship therewith, such as on a PCI board, or they may be located remotely from the chip, such as on a different PCI board, or even on a different server, such as on a server that may be accessed via the cloud. For instance, in certain implementations, one or more of the above described modules may be hardwired onto a chip and the chip installed onto the circuit board of a stand-alone device, or coupled to a sequencer, whereby the user configures and runs the system directly by themselves according to their own preselected parameters. Alternatively, as indicated herein, one or more of the above described modules may be present on a system that is accessible via the cloud, wherein the directing of the functioning of the pipeline, and/or the modules thereof, may include the user logging on to a server, e.g., a remote server, and transmitting data to and therefrom, and thereby selects which modules to be run on the data set. In certain instances, one or more of the modules may be performed remotely, such as via the cloud accessed server.

In various instances, in configuring the system, the chip, e.g., the chip on an expansion card, such as a PCI card, may be included in a server, whereby the server runs the various applications of the system. In certain instances, the server may have a terminal connectable there with, whereby a windows interface may be presentable to the user such that the user may select the modules to be run and the parameters by which they are to be run, such as by selecting a box from a menu of boxes. In other instances, however, the parameter file may be a text file detailing categories by module under file names that the user can then edit, so as to select which modules will be run in accordance with which parameters. For instance, in various embodiments, each chip may include all or a selection of the modules, such as one or more of: a base calling, error correcting, a mapping, an alignment, a sorting, a local realignment, a duplicate marking, a recalibration, a variant calling, a compression, and/or a decompression module, from which the user may select which modules will run, when, and to various extents how it will run, without changing the functioning of the underlying algorithms by which the individual modules are operated.

Additionally, in various instances, a direct memory access (DMA) engine in the chip, and a DMA driver, may be included wherein the DMA driver includes code that runs in the kernel. Accordingly, the DMA driver may be the foundation of the overall operating system. For instance, where the kernel runs in a literal addressing space, layered above that may be a virtual user space. This operating system software, therefore operates in between these layers managing the mapping from the virtual to the physical space. More particularly, the kernel represents the lowest level of code that gives the platform access to the PCI, e.g., PCIe, bus, to which the chip is coupled. Accordingly, since, in various embodiments, the chip may be configured as an expansion card with a PCIe expansion bus, which expansion card may be coupled with various hardware of a device, such as a sequencer, the DMA driver may function so as to communicate with the hardware of the sequencer, and may further be configured for running at the kernel level on the CPU, so as to also communicate with the DMA engine in the chip, and/or be configured for operating in the virtual user space so as to receive instructions from the user.

To facilitate this communication within the chip and/or between the chip and one or more cards, every single configurable parameter of a module may be assigned to a register address. In such an instance, the card may have its own address space, which address space may be different from the address space for one or more memories, such as 64 gigabytes of memory, and/or additionally every module may have registers and local memory associated with it, each with its own address space. Accordingly, the driver knows where everything is, all the addresses, and knows how to communicate between the chip, the PCI card, and/or the hardware of the server. Further, knowing where all the addresses are and communicating with an API the driver can read the parameter file that a user generates, and can look up for that parameter where the file is actually located in the host computer system and will read and interpret the value in the file and will deliver that value in the right register in the right place in the chip. Hence, the driver may handle delivering the selected parameter instructions, such as with respect to various user selected configurations, and ships that data to the chip via the DMA engine to configure any of its processing functions.

Further, in various instances, an API may be included wherein the API is configured so as to include a list of function calls that the user can make, so as to configure and operate the system. For instance, an API may be defined in a header file that describes the functionality and determines how to call a function, such as the parameters that are passed, the inputs and outputs, what comes in, what goes out, and what gets returned. For example, in various embodiments, one or more of the elements of the pipeline may be configurable such as by instructions entered by a user and/or one or more third party applications. These instructions may be communicated to the chip via the API which communicates with the driver, instructing the driver as to which parts of the chip, e.g., which modules are to be activated, when, and in what order, given a preselected parameter configuration.

As indicated above, the DMA driver runs at the kernel level, and has its own very low level, basic API that provides access to the hardware and functions so as to access applicable registers and modules. On top of this layer is built a virtual layer of service functions, that form the building blocks that are used for a multiplicity of functions that send files down to the kernel and gets results back, and further performs more higher level functions. On top of that layer is an additional layer that uses those service functions, which is the API level that a user will interface with and it functions primarily for configuration, downloading files, and uploading results. Such configuration may include communicating with registers and also performing function calls.

For example, as described herein above, one function call may be to generate the hash table via the hashing algorithm. Specifically, because in certain embodiments this function may be based on a reference genome, once for every reference genome, the hash tables that are used in the mapper may need to be constructed, based on the reference, there is therefore a function call that performs this function, which function call will accept a file name of where the reference file is stored and it will then generate one or more data files that contain the hash table and the reference. Another function call may be to load the hash table that was generated via the hashing algorithm and transfer that down to the memory on the chip, and/or put it at the right spot where the hardware is expecting them to be. Of course, the reference itself will need to be downloaded onto the chip, as well for the performance of the alignment function, and the configuration manager can perform that function such as by loading everything that needs to be there in order for the modules of the chip to perform their functions into a memory on to the chip or attached to the chip.

Additionally, the API may be configured to allow the chip to interface with the circuit board of the sequencer, when included therewith, so as to receive the FASTQ sequencing files directly from the sequencer such as immediately once they have been generated and then transfers that information to the configuration manager which then directs that information to the appropriate memory banks in the hardware that makes that information available to the pertinent modules of the hardware so that they can perform their designated functions on that information so as to call bases, map, align, sort, etc. the sample DNA with respect to the reference genome.

Further still, a client level interface (CLI) may be included wherein the CLI may allow the user to call one or more of these functions directly. In various embodiments, the CLI may be a software application that is adapted to configure the use of the hardware. The CLI, therefore, may be a program that accepts instructions, e.g., arguments, and makes functionality available simply by calling an application program. As indicated above, the CLI can be command line based or GUI (graphical user interface) based. The line based commands happen at a level below the GUI, where the GUI includes a windows based file manager with click on function boxes that delineate which modules will be used and the parameters of their use. For example, in operation, if instructed, the CLI will locate the reference, will determine if a hash table and/or index needs to be generated, or if already generated locate where it is stored, and direct the uploading of the generated hash table and/or index, etc.

These type of instructions may appear as user options at the GUI that the user can select the chip to perform.

Furthermore, a library may be included wherein the library may include pre-existing, editable, configuration files, such as files orientated to the typical user selected functioning of the hardware, such as with respect to a portion or whole genome analysis, for instance, for ancestry analysis, or disease diagnostics, or drug discovery, or protein profiling, etc. These types of preset parameters, such as for performing such analyses, may be stored in the library. For example, if the platform herein described is employed such as for oncology research, the preset parameters may be configured differently than if the platform were directed simply to researching a genealogy.

More particularly, for oncology, accuracy may be an important factor, therefore, the parameters of the system may be set to ensure increased accuracy albeit in exchange for possibly a decrease in speed. However, for other genomics applications, speed may be the key determinant and therefore the parameters of the system may be set to maximize speed, which however may sacrifice some accuracy. Accordingly, in various embodiments, often used parameter settings for performing different tasks can be preset into the library to facilitate ease of use. Such parameter settings may also include the necessary software applications employed in running the system. For instance, the library may contain the code that executes the API, and may further include sample files, scripts, and any other ancillary information necessary for running the system. Hence, the library may be configured for compiling software for running the API as well as various executables.

In various instances, the chip may also include a memory, such as a Random Access Memory (RAM) or a Dynamic Rapid Access Memory with e.g. a DDR3 interface, such as a memory that may be used for facilitating the performance of the various modules described herein, for instance, the mapper, aligner, and/or sorter. For example, the DRAM may be where the reference, the hash table, and/or the hash table index, and/or reads may be stored. Further, the memory may be used for facilitating the performance of various other modules described herein, for instance, the deduper, local realigner, base quality score recalibrator, variant caller, compressor, and/or decompresor. For example, the DRAM may be where sorted reads, annotated reads, compressed reads, and/or variant calls may be stored. Further, the memory may be configured so as to include a separate interface for each of the various memory modules employed by the aligner and/or any other module, such as where each memory may include a file layer and logical layer. As indicated above, because there may be multiple memories and/or multiple modules, a chip level interconnect may be included so as to facilitate communication through the chip.

Accordingly, in various instances, an apparatus of the disclosure may include a chip, wherein the chip includes an integrated circuit that is formed of a set of hardwired digital logic circuits that may be interconnected by one or more physical electrical interconnects. In various embodiments, the one or more physical electrical interconnects include an input to the integrated circuit that may be connected with an electronic data source for receiving data. Further, in certain embodiments, the hardwired digital logic circuits may be arranged as a set of processing engines, such as wherein each processing engine may be formed of a subset of the hardwired digital logic circuits, which are configured to perform one or more of the steps in the sequence analysis pipeline. More particularly, each subset of the hardwired digital logic circuits may be in a wired configuration so as to perform the one or more steps in the sequence analysis pipeline.

In various instances, the set of processing engines may include one or more of a mapping module, an alignment module, and/or a sorting module, such as where the one or more of these modules are in the wired configuration. For instance, a mapping module may be included, where in the wired configuration, the mapping module may access an index, such as of one or more genetic reference sequences, e.g., from a memory, such as via one or more of the plurality of physical electronic interconnects, so as to map the plurality of reads to one or more segments of the one or more genetic reference sequences. Further, in various instances, an alignment module may be included, wherein the wired configuration, the alignment module may access the one or more genetic reference sequences, e.g., from the memory, such as via one or more of the plurality of physical electronic interconnects, so to align the plurality of reads to the one or more segments of the one or more genetic reference sequences. Further still, in various instances, a sorting module may be included, wherein the wired configuration, the sorting module may access the one or more aligned sequences, e.g., from the memory, such as via one or more of the plurality of physical electronic interconnects, so to sort the plurality of reads to a chromosome, such as from the one or more genetic reference sequences. In like manner, in various instances, one or more of local realignment, duplicate marking, base quality score recalibration, and/or variant calling modules may be included in the chip, such as in the wired configuration consistent as with the modules described above, so as to perform their respective functions.

As indicated above, in various instances one or more integrated circuits of the disclosure may be configured as one or more chips such as one or more of an ASIC, a FPGA, and/or a structured ASIC chip. For instance, an integrated circuit is characteristically a set of electronic circuits on a wafer or "chip" of semiconductor material, such as silicon. Typically integrated circuits include circuit elements that may be inseparably associated and electrically interconnected. A prototypical digital integrated circuit includes a variety of circuit elements such as one or more of logic gates, flip-flops, multiplexers, and other various circuit elements that are configured and/or configurable for functioning in circuit such as a microprocessor, or other microcontroller, such as for binary processing of "zero" and "one" signals, for instance, in the performance of one or more of the operations of the disclosure.

More particularly, one or more mask-programmable logic gates may be configured or programmed for performing a logical operation, such as implementing a Boolean function, on one or more logical inputs so as to produce a single logical output. Such logic gates may be configured using one or more diodes or transistors in such a manner that the gate operates as an electronic switch. In various instances, logic gates can be cascaded in a manner akin to the way that Boolean functions can be composed, thereby allowing the construction of a physical model of all of Boolean logic and, therefore, all of the algorithms and mathematics that can be described with Boolean logic, such as those described herein, may be implemented in the logic gates of the integrated circuits of the present disclosure. In various embodiments, a collection of gates may be present on the wafer in such a manner as to form a gate array, such as a gate array circuit.

In various instances, an integrated circuit may also include one or more flip-flops. A flip-flop may be a circuit, or at least a part thereof, that is configured as a latch. Typically, a flip-flop has two stable states and can change from one to the other such as by signals applied to one or more control inputs, and, therefore, a flip-flop will have one or two outputs. In use, flip-flops are employed to store state information, and consequently, may be deployed as a basic storage element, such as in sequential logic operations. The integrated may also include a multiplexer. A multiplexer may be configured for selecting one of several input signals, such as digital (or analog) input signals, and further may be configured for forwarding the selected input to an output. In this manner, a multiplexer may be used to increase the amount of data that can be sent over a network within a certain amount of time and bandwidth.

In certain instances, as recited herein, a typical integrated circuit can include anywhere from one to millions of such circuit elements configured for performing operations, such as those operations presently disclosed, wherein the various circuit elements occupy only a few square millimeters of space. The small size of these circuits allows high speed, low power dissipation, and reduced manufacturing cost.

Such integrated circuits may be fabricated using a variety of different technologies but, in general, are usually constructed as a monolithic integrated circuit. For instance, a typical integrated circuit, e.g., a semiconductor, may be fabricated in a layer process, such as a layer process that includes about three main process steps, such as imaging, deposition and etching. In various instances, one or more of these process steps may be supplemented by further processing steps such as doping, cleaning, and the like. For example, in a typical fabrication procedure, a wafer, such as a mono-crystal silicon wafer may be provided for use as a substrate upon which the integrated circuit is to be constructed, e.g., printed. Photolithography may then be employed to print on the wafer so as to mark different areas of the substrate that may then be doped and/or printed with tracks, such as with a metal insulator such as aluminum.

Typically, an integrated circuit is composed of one or a plurality of overlapping layers, such as where each layer is defined by photolithography. Some layers may form diffusion layers, marking where various dopants have diffused into the substrate, and other layers define where additional ions may be implanted. Additional layers may define the conductors (e.g., polysilicon, metal layers, and the like) as well as the connection layers between the conducting layers. For instance, a transistor may be formed wherever the gate layer (polysilicon or metal) crosses a diffusion layer, and in various instances, meandering stripes may be used to form on-chip resistors. Exemplary integrated circuits may include: an ASIC, an FGPA, and/or a Structured ASIC.

Often times, integrated circuits are fabricated for general use. However, in various instances, such as some of those described herein, an integrated circuit may be customized, such as to form an application-specific integrated circuit or "ASIC." An ASIC, generally referred to as a "standard cell ASIC," is an integrated circuit that has been customized for a particular use, rather than for a general-purpose use. Typically an ASIC may have a large number of logic gates, such as in some instances, over 100 million gates, which gates can be configured for preforming a multiplicity of different operations such as being configured as microprocessors and/or memory blocks, including ROM, RAM, EEPROM, flash memory, and other large building blocks, such as for the purpose of performing the operations herein disclosed. A unique feature of an ASIC is that because it is a chip that is constructed for performing a specific set of applications, the chip may be fabricated in such a manner as to be customizable, such as by employing a gate-array design protocol.

For instance, a gate array or uncommitted logic array (ULA) may be used in the design and manufacture of application-specific integrated circuits (ASICs). In such an instance, an ASIC may be manufactured from a prefabricated chip that has active devices like gates, e.g., NAND-gates, which at first may be unconnected, but may at a later time be interconnected, such as according to the gate-array design protocol, for example, by adding metal layers, such as in the factory. Accordingly, with respect to producing an ASIC, a gate array circuit may be prefabricated on a silicon chip circuit that upon production has no particular function, but does include one or more of transistors, standard NAND or NOR logic gates, and may have further other active devices that may be placed at predefined positions and manufactured on the wafer, which wafer in this instance may be termed a "master slice." Hence, the creation of a circuit having the determined specified functions may be accomplished by adding a final surface layer or layers of metal interconnects to the chips on the master slice late in the manufacturing process, and joining these elements to allow the function of the chip to be customized as desired, e.g., in accordance with the design protocol.

More particularly, a gate-array design protocol employs a manufacturing method where the various diffused layers, e.g., transistors and other active circuit elements, such as those described above, are predefined and constructed on general use wafers but are stored prior to metallization such that various of the circuit elements remain unconnected. In such an instance, the chip may then, at a later point in time, be customized in accordance with various specific use parameters such as by a physical design process that defines the interconnections of the final device. For instance, gate array master slices are usually prefabricated and stockpiled in large quantities waiting for customization. An application circuit must be built on the gate array in such a manner that the circuit has enough gates, wiring and I/O pins so as to perform the desired functions. Since requirements vary, gate array wafers often come in standard families, including larger members having more, e.g., all, resources, but being correspondingly more expensive, and somewhat smaller members having a limited selection of resources, but also being less expensive. The right wafer standard should be chosen based on the number of resources required to perform the selected functions. The amount of resources to be deployed may fairly easily be determined, such as by counting how many gates and I/Os pins are needed, however, the amount of routing tracks needed may vary considerably and should therefore be selected carefully. However, because the master slice is somewhat prefabricated, the design and fabrication, according to the individual design protocol specifications, may be finished in a shorter time compared with standard cell or full custom (FPGA) design. In a manner such as this, the gate array approach reduces the mask costs, since fewer custom masks need to be produced. In addition manufacturing test tooling lead time and costs are also reduced, since the same test fixtures may be used for all gate array products manufactured on the same die size.

In such an instance, the manufacture of such a standard cell ASIC may include anywhere from two to nine, or ten, or twelve, or more deposition layers, such as where one or more, e.g., all, of the subsequent metal layers run perpendicular to the one below it. Such fabrication methods are useful because they provide for a somewhat customized chip design in a relatively short construction time period because the final metallization process can be performed quickly. However, such gate-array ASICs are often a compromise as mapping a given design onto a "stock" wafer does not typically give 100% utilization. Another disadvantage with respect to an ASIC is the non-recurring engineering (NRE) cost that can run into the millions of dollars. Nevertheless, the per unit production cost of an ASIC can be quite low, comparatively.

An alternative to a standard cell ASIC for the production of customizable chips is a field-programmable gated array or "FPGA." An FPGA employs programmable logic blocks and interconnects that are re-writeable thereby allowing the same FPGA to be designed and at least partially re-designed so as to be used in many different applications, or the same applications in a multiplicity of different ways over time. More specifically, a field-programmable gate array is an integrated circuit that is designed to be configured one or a multiplicity of times, such as by a customer or a designer, e.g., after manufacturing.

Typically, FPGAs have large resources of logic gates and/or memory, e.g., RAM, blocks that can be configured to implement complex digital computations. For instance, FPGAs contain programmable logic components called "logic blocks", as well as a multiplicity, e.g., a hierarchy, of reconfigurable interconnects that allow the blocks to be "wired together." More particularly, FGPAs may have a multiplicity of changeable logic gates that can be inter-wired in a variety of different configurations, so as to form logic blocks that can be configured to perform a wide variety of complex combinational functions, such as those with respect to performing the operations herein detailed. In various instances, the logic blocks of an FPGA may be configured to include memory elements such as simple flip-flops or more complete memory blocks such as ROM or RAM. As FPGA designs employ very fast I/Os and bidirectional data buses it may, in certain instances, be difficult to verify the correct timing of valid data within setup and hold times. Accordingly, in some instances, the appropriate floor planning may enable resource allocations within an FPGA to meet these time constraints. FPGAs, therefore, may be used to implement any logical function that a standard cell ASIC could perform. However, the ability to update the functionality after shipping, partial re-configuration of a portion of the design, and the low non-recurring engineering costs relative to an ASIC design (notwithstanding the generally higher per unit cost), offer advantages for many applications.

In some instances, the coarse-grained architectural approach of a typical FPGA fabrication may be performed in such a manner as to combine the logic blocks and interconnects of traditional FPGAs with embedded microprocessors and related peripherals to form a complete "system on a programmable chip". In certain instances, an FPGA of the disclosure may have the ability to be reprogrammed at "run time," and may, in accordance with the methods disclosed herein, allow for reconfigurable computing or the production of reconfigurable systems, e.g., a CPU that can reconfigure itself to suit the operations disclosed herein. In some instances, software-configurable microprocessors may be employed to provide an array of processor cores and FPGA-like programmable cores that may be present on the same chip.

A common FPGA architecture may include an array of configurable logic blocks, I/O pads, and/or one or more routing channels. Typically, a logic block may include one or a plurality of logical cells, where a typical cell may include a 4-input LUT, a Full adder (FA), and/or flip-flop, and the like, which function to produce an output. In various instances, the output can be either synchronous or asynchronous. An application circuit may be mapped into an FPGA and the number of logic blocks, I/Os, and routing tracks to be included can be determined from the design, the number of which may vary. It is to be noted that since unused routing tracks may increase the cost and decrease the performance of the integrated circuit without providing any benefit, the number of routing tracks should be enough such that its processes fit in terms of lookup tables (LUTs) and I/Os to be routed without being in excess. Further, since clock signals are normally routed via special-purpose dedicated routing networks (e.g., global buffers) they and other such signals may be separately managed.

An FPGA, as herein disclosed, may also include higher level functionality fixed into the silicon, such as one or more multipliers, generic DSP blocks, embedded processors, high speed I/O logic, and/or embedded memories. Inclusion of these common functions embedded into the silicon wafer reduces the area required and gives those functions increased speed. It is to be noted that the disclosed FPGAs may be used for systems validation including pre-silicon validation, post-silicon validation, and firmware development, such as to validate the final design prior to the production of "for use" chips, such as standard cell ASIC or Structured ASIC chips, which may represent the final end product.

In the production of an exemplary integrated circuit, such as an FPGA, etc., having the requisite functionality as herein described, one or more of the following steps may be followed, in any logical sequence. First, a hardware description language (HDL) or a schematic design may be provided. An electronic design automation tool, e.g., a CAD, can then be employed to generate a technology-mapped netlist. The netlist can then be fitted to the actual FPGA architecture such as by using a process called place-and-route in accordance with the appropriate place-and-route software. Once the design and validation process is complete, the binary file generated may be used to (re)configure the FPGA.

In a typical design protocol flow, the design may be simulated at multiple stages throughout the design process. Initially the RTL description, such as in VHDL or Verilog, may be simulated by creating test benches to simulate the system and observe results. In certain instances, the synthesis engine may map the proposed design to the netlist, and after the synthesis engine has mapped the design to a netlist, the netlist may be translated to a gate level description. At this stage a simulation may be performed, e.g., again, to confirm the synthesis proceeded without errors. The design may then be laid out in the FPGA, at which point propagation delays may be added, and a simulation may be run, e.g., again, with these values back-annotated onto the netlist, such as prior to final validation and further fabrication, such as in the generation of one or more ASIC or structured ASIC based chips.

Accordingly, a hybrid between an ASIC and a FPGA is a structured ASIC, which falls between an FPGA and an ASIC. The traditional "standard cell ASIC", disclosed above, is typically expensive, e.g., extremely expensive, and time consuming to develop. For instance, in developing a standard cell ASIC a large set of photolithographic masks may be produced for each standard cell ASIC design. However, after this up-front investment in the initial development has been made, the typical production costs become very low, and the operating parameters with respect to power, frequency, and logic capacity can readily be optimized.

Alternatively, unlike Standard cell ASICs, the typical FPGA and/or CLPD, containing programmable logic, are relatively fast and cheap to develop, largely because the pre-existing devices are programmed electronically, and no photolithographic masks are required. However, with respect to operating parameters, such as power, frequency, and logic capacity, these are poor in comparison to a standard cell ASIC, and per-unit costs can be very high, particularly for large-capacity devices.

Structured ASICs, on the other hand, are a compromise between these two. Unlike gate arrays, structured ASICs tend to include predefined or configurable memories and/or analog blocks. Hence, development cost is much lower than for standard cell, because only a few photolithographic masks must be produced for each structured ASIC design, such as for configurable metal layers. And, although per-unit production costs are significantly higher than standard cell, they are still far lower than FPGA unit costs. With respect to power and frequency, these are a compromise between standard cell and FPGAs, but their logic capacity is similar to the largest FPGAs. Hence, in many instances, structured ASICs may be a technology that can reduce the up-front cost and time to develop a new custom integrated circuit. See Table 1.

TABLE 1

|  | FPGA | Structured ASIC | Standard Cell ASIC |
| --- | --- | --- | --- |
| Silicon area | Very high | Low | Very low |
| Power utilization | High | Low | Very low |
| Operating frequency | Low | High | High |
| Logic capacity | Medium | Medium | High |
| Development cost | Very low | Low | High |
| Per-unit cost | Very high | Low | Very low |

Figure 9:
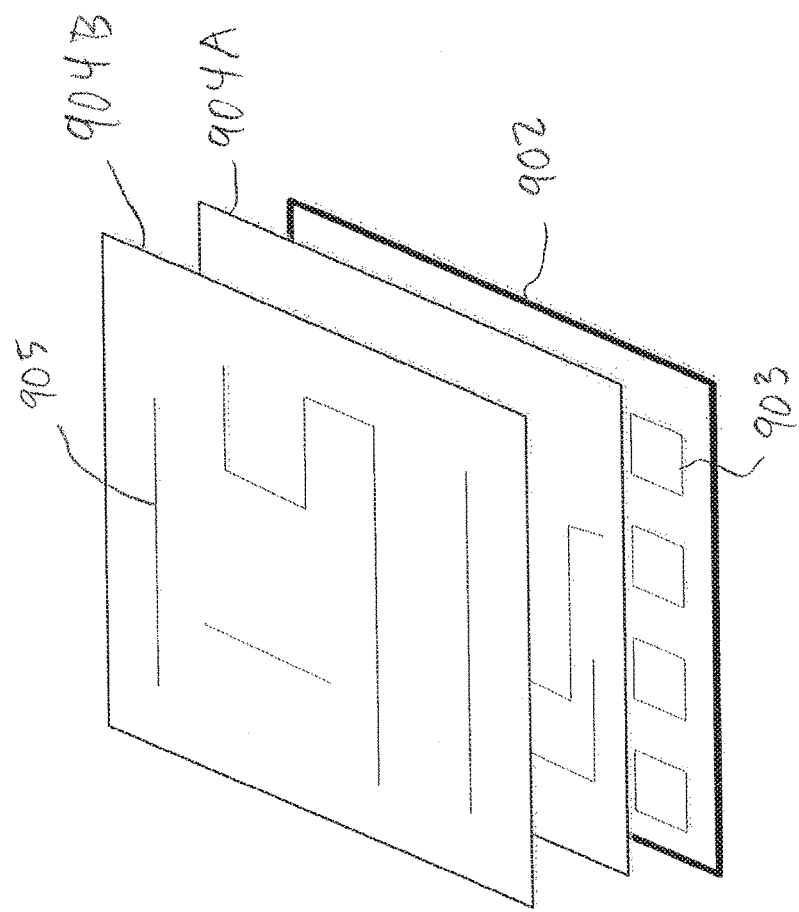
FIG. 9 illustrates an exemplary design and fabrication of an integrated circuit, such as a structured ASIC.

With respect to design and fabrication of a structured ASIC, and as shown in FIG. 9, before a series of structured ASICs can be developed, a "master slice" 902 may first be developed, such as by using standard cell ASIC methodology. As indicated above, the master slice may include most of the typical integrated circuit layers, such as one or more transistors, memories or memory cells, input/output cells, phase-locked loops, or other clock generators, and the like. Optionally a master slice may contain flip-flops, latches, and/or multi-transistor combinational gates. Some amount of local wiring between components may be included in the master slice, but much of the wiring to implement a full logic design may be omitted, such as to be added later. Note that a master slice can theoretically be constructed to include any logic suitable for standard cell ASICs, potentially including large complex modules, and operating parameters (power, frequency, logic capacity) of master slice logic are optimal, just as for standard cell ASICs. Photolithographic masks may be produced for master slice content, the mask set being similar or somewhat smaller than a standard cell ASIC mask set. Accordingly, the master slice 902 includes a set of digital logic circuits 903 that may or may not yet be hardwired to function in a particular way.

Following construction of the master slice 903, a series of one or more complete structured ASICs may be implemented, such as by building upon the same master slice. Typically many structured ASIC designs utilize the same master slice, to amortize the cost of the master slice over many projects. Each individual structured ASIC design may be implemented by determining a set of new wired connections between components (transistors, etc.) in the master slice, which will effectively build the master slice components into higher level gates, flip flops, latches, memories, and large complex logic modules. Accordingly, these determined wired connections 905 may be implemented in a small number of additional "configurable" metal layers 904A and 904B fabricated on top of the master slice, such as by connecting metal pads, or vias, in the master slice, for instance, by wires in the configurable metal layers. These additional metal layers are called "configurable" because they can be customized to each structured ASIC design project; however, they are fixed at fabrication time and cannot be rewired electronically except as the implemented logic design provides. There can be any number of configurable metal layers 904.

Most any conceivable logic design can thus be implemented using a master slice and appropriate wiring metal layers, as long as the master slice contains enough logic resources (transistors, memories, etc.) to form all the required logic design elements. The number of configurable metal layers varies from one structured ASIC design flow to another, but typically may be between 1 and 5 configurable metal layers more or less. A small additional set of photolithographic masks may be produced, corresponding to the configurable metal layers, and in device fabrication, the full mask set (master slice masks and configurable metal layer masks) may be used to build wafers of complete structured ASIC dice. Alternatively, master slice wafers might be pre-fabricated in bulk, and metal layers added in a later fabrication step to complete wafers of specific structured ASIC designs.

Advantageously, a structured ASIC master slice can be designed in one step, e.g., by a first designer, while specific structured ASIC logic designs based on that master slice may be designed, in a second step, such as by various other designers utilizing services of the structured ASIC designer. In particular, the various parties may typically be responsible for "front end" logic design specific to the desired integrated circuit functionality, such as RTL (register transfer logic) code development, simulation, emulation, regression testing, debugging, and the like; while the structured ASIC designer may typically be responsible for "back end" design flow, including synthesis, place and route, static timing analysis, test logic insertion, and/or tapeout. An additional party, e.g., a foundry, may be employed to produce physical photolithographic masks, fabricate wafers, and/or test and/or package the device dice. In various instances, a structured ASIC designer may also design custom master slices for a particular application class, such as to contain logic resource types or quantities customized to those applications.

Accordingly, by virtue of there being pre-defined metal layers (thus reducing manufacturing time) and pre-characterization of what is on the silicon wafer, e.g., master slice, (thus reducing design cycle time) the cycle time and design cycle time in the structured ASIC may be reduced as compared to typical ASIC manufacturing processes. For instance, in a cell based ASIC design or FPGA, e.g., gate-array, design the user may often have to design power, clock, and test structures themselves. However, in a structured ASIC these may be predefined which can save production time and expense as compared to cell based or gate-array profiles.

Particularly, the design task for structured ASIC's is to map the circuit into a fixed arrangement of known cells. More particularly, the comparative architecture of a structured ASIC typically may include two main levels, such as both structured elements and an array of structured elements.

Such structured elements may include both combinational and sequential function blocks, which can function as either logical or storage elements. Additionally, with respect to arrays of structural elements, uniform or non-uniform array styles may be employed such as in a fixed arrangement of structured elements.

Consequently, in a structured ASIC design, the logic mask-layers of the device may be predefined. In such an instance, design differentiation and customization may be achieved such as by creating custom metal layers that create custom connections between predefined lower-layer logic elements. Likewise, the design tools used for structured ASIC can be substantially lower in cost and easier (faster) to use than cell-based tools, because they do not have to perform all the functions that cell-based tools do. More particularly, pre-existing standard cell-based CAD tools may be used in the design process. In some instances, however, CAD tools designed specifically for structured ASIC's may be used. Product specific placement tools may also be used. Further, as disclosed herein, new and improved algorithms have been developed so as to exploit the modularity of structured ASIC's, and better account for a more clock aware design. Additionally, the methods herein disclosed may be employed so as to enhance the evaluation and analysis processes as discussed above.

In these manners the structured ASIC technology may act as a bridge filling the gap between field-programmable gate arrays and standard ASIC designs. More specifically, because only a small number of chip layers need be custom-produced, structured ASIC designs may have much smaller non-recurring expenditures (NRE) than "standard-cell" or "full-custom" chips, which require that a full mask set be produced for every design. Accordingly, a structured ASIC offers high performance (a characteristic of a typical ASIC), and low NRE cost (a characteristic of FPGA). Hence, a Structured ASIC fabrication process can be employed so as to allow the end product to be introduced quickly to market, to have lower cost, and to be more easily designed.

In some instances, however, a FPGA, may be advantageous in that the interconnects and logic blocks are programmable after fabrication. This offers a high flexibility of design and ease of debugging in prototyping. However, the capability of FPGAs to implement large circuits is sometimes limited, in both size and speed, which in some circumstances, may be due to the inherent complexity in programmable routing and/or significant space that may be occupied by the various included programming elements. On the other hand, ASICs also have some disadvantages, such as an expensive design flow, due in part to the fact that every different design typically needs a complete different set of masks. The structured ASIC, therefore, may be a solution between these two. It may basically have the same structure as a FPGA, but may be mask-programmable, such as in an ASIC, instead of being field-programmable, by configuring one or several via layers between metal layers. For instance, one or more, e.g., each SRAM configuration bit can be replaced by a choice of either including or not including a via or between various metal contacts.

For example, with respect to the architecture of a structured ASIC, a typical architecture may often times be fine-grained, medium grained, and/or hierarchical. A fine-grained architecture may include many connections in and out of a structured element, whereas higher granularities reduce connections to the structured element but may also decrease the functionality it can support. Each individual design will benefit differently at varying granularities. More particularly, in a fine-grained architecture, the architecture may include structured elements that contain unconnected discrete components, such as transistors, resistors, and other control elements that can later be connected. In a medium grained architecture, the architecture of the structured elements may include generic logic as well as gates, MUX's, LUT's and/or storage elements, such as flip-flops. Alternatively, in a hierarchical architecture, the architecture may include mini structured elements, for instance that contain gates, MUX's, and LUT's, but do not typically contain storage elements like flip-flops. In other instances, the mini element may be combined with registers or flip-flops.

With respect to implementing a structured ASIC the various fabrication steps may include one or more of register transfer level design (RTL); logical synthesis, so as to map the RTL into structured elements; design for test insertion, so as to improve testability and fault coverage; placement, so as to map each structured element onto an array element and to place each element into a fixed arrangement; physical synthesis in such a manner that improves the timing of the layout, and optimizes the placement of each element; clock synthesis in a manner that distributes the clock network and minimizes the clock skew and delay; as well as routing or otherwise inserting the wiring between the various elements. In various instances, these steps may be performed in any logical order and in a manner to make the design process, such as with respect to logical synthesis, less complex, as well as to help build up a more complete target structured ASIC library that enhances what specifically can be implemented from the design.

Furthermore, it has become common for some designers of processor cores to license the processor design to various customers so as to embed in their own silicon devices. Such embedded cores may include ARM, PowerPC, Krait, etc. as general-purpose processors, and may also include more specialized processors such as graphics processors (GPUs) or vector processors. Embedded processor cores may be large, complex logic modules, pipelined to run at high operating frequencies such as about 1 or 2 GHz to about 3 to 6 GHz, or more. In order to achieve such high frequencies, careful physical layout and routing may be used for processor cores and associated cache memory; and as a result, embedded processor technology may often be supplied as a "hard macro" (such as for defining precise placement and routing of the subcomponents) for a particular silicon fabrication process.

However, such an embedded processor core may be a suboptimal candidate for implementation in a structured ASIC using configurable metal layers. Hard macros do not generally apply to structured ASIC configurable layers, and even if an embedded processor were implemented as closely as possible to its hard macro in the configurable metal layers, it would likely be frequency limited (e.g. 30% or 50% of nominal operating frequency), and would likely consume very large portions of the available master slice resources. The relative area inefficiency of structured ASIC fabric as compared to standard cell could cause the embedded processor to cover a significantly larger physical silicon area, and in combination with reduced operating frequency, the performance to area (or cost) ratio could be much lower than a standard cell implementation of the same embedded core.

However, it is practical to implement embedded one or more processor cores efficiently in a structured ASIC master slice, such as by using a standard cell design methodology, as disclosed herein, including the use of hard macros. These would retain full operating frequency and performance, and consume only normal silicon area. The processor core and/or cache input and output wires could be connected to other resources in the master slice, or advantageously, exposed to configurable metal layer routing, to enable the embedded cores to be connected to any infrastructure and logic modules implemented in each particular structured ASIC design. In a manner such as this, the embedded processor cores become master slice resources available to many various structured ASIC designs later implemented using the master slice.

Embedded processor cores in a structured ASIC can be connected to logic infrastructure so that software (firmware) running on the cores can share and access various memory and other resources, on-chip and off-chip, and to communicate with any or all other logic modules on the chip, via memory and/or directly. In this manner, the processor cores can operate in parallel with other logic modules, and/or cooperate with other logic modules to complete joint work, such as by the processor cores requesting tasks to be performed by other modules, or other modules requesting tasks to be performed by the processor cores, or both.

When Bio-IT acceleration modules (such as to perform mapping, alignment, sorting, duplicate marking, base quality score recalibration, local re-alignment, variant calling, compression, decompression, etc. as described herein) are implemented in a structured ASIC along with embedded processor cores, the resulting system on a chip (SOC) has important advantages, especially in a combination of speed and flexibility. Extreme speed may be achieved by the hardware acceleration modules, and extreme flexibility may be achieved by the full programmability of the processor cores. By reprogramming the processor cores, the bio-IT algorithms executed can be easily modified, but these algorithms can run orders of magnitude faster than in traditional CPUs because computationally intensive operations may be offloaded to hardware accelerators. Communication and memory organization can be optimized for cooperative processor-accelerator work. Additional software algorithm acceleration can be obtained by additional hardware modules designed to pre-process or post-process data used by the processor cores, such as organizing reads overlapping a reference genome locus into a pileup data structure, for presentation to the processor cores. In some processor architectures, instruction sets can be extended to utilize connected hardware resources; in the Bio-IT SOC environment, new processor instructions can be defined to access Bio-IT hardware acceleration functions.

As summarized in Table 2, below, a structured ASIC, therefore, has several prefabricated advantages, such as over an ASIC or FPGA. For instance, the various components may be "almost" connected, such as in a variety of pre-defined configurations, and multiple global and local clocks may be prefabricated. This means, therefore, that signal integrity and timing issues should inherently be addressed. Additionally, only a few metal layers may be needed for fabrication. Further, unlike standard FPGAs, the structured ASIC should have a capacity, performance, and power consumption closer to that of a standard cell ASIC. This should allow for easier and faster design processes and times as well as reduced NRE costs than in standard cell ASIC's, and should drastically reduce turnaround time. Further still, no skew problems should need to be addressed.

TABLE 2

|  | FPGA | Structured ASIC | Standard Cell ASIC |
| --- | --- | --- | --- |
| Silicon area | Very high | Low | Very low |
| Power utilization | High | Low | Very low |
| Operating frequency | Low | High | High |
| Logic capacity | Medium | Medium | High |
| Development cost | Very low | Low | High |
| Per-unit cost | Very high | Low | Very low |

A structured ASIC, therefore, has several different beneficial properties, including one or more of: low NRE cost, lower requirements for implementation engineering efforts, lower mask tooling charges, such as over an ASIC, with the additional benefits of high performance, low power consumption, fewer fabrication layers, less complexity, in a pre-made cell block configuration that is available for placing circuit elements, together which leads to a quicker production time. There are, however, some disadvantages to structured ASICs, for instance, there are sometimes a lack of adequate design tools, which tools and processing may be expensive and need to be altered from traditional ASIC tools. Further, these new architectures are still being subjected to formal evaluations and comparative analyses. And, there may be tradeoffs between 3-, 4-, and 5-input LUT's, and/or between sizes of distributed RAM.

Accordingly, in view of the above, there are both advantages and disadvantages to ASICs, FPGAs, and Structured ASICs. For instance, standard cell ASICs may be difficult to design, need a long development time, have a high NRE cost. However, an ASIC may also support large designs, support complex designs, have a high performance at a low power consumption, which therefore could result in a low or lower Per-Unit Cost (at high volume). On the other hand, FPGAs may be easy to design, involve a short development time, and a low NRE cost. However, FPGAs may have a limited design size and/or complexity, may have limited performance, and a high power consumption, which may result in a high or higher Per-Unit Cost. In many instances, a structured ASIC may be designed to maximize these benefits and minimize these disadvantages. For instance, generally speaking there may be about a 100:33:1 ratio between the number of gates in a given area for standard cell ASIC's, structured ASIC's, and FPGA's; a 100:75:15 ratio for performance (based on clock frequency); and a 1:3:12 ratio for power, respectively.

For instance, in certain embodiments, structured ASICs represent a lower cost way to make a custom microchip. However, there may be a tradeoff in efficiency and/or cost per unit, however, with a lower NRE to make. An ASIC may be fabricated by a typical vendor (e.g., TOSHIBA makes a series of "master slices" on which upper metal layers can be added), which fabricator can make a CM Gate, including transistors and memory blocks, that may be fixed, but not at first wired together (e.g., they may start out as discreet separate units). During the fabrication process the layers may be mixed and matched so as to build the chip. For instance, bottom layers may connect to I/Os, while upper layers may have additional wires to connect the flip-flops together, so as to create the transistors. In a typical TOSHIBA design one to four metal layers may be added, e.g., for adding onto the "master slice". Thus, with respect to a structured ASIC, logic may be prebuilt, but the connecting wires may be made of a custom partial mask set. Not all of the masks need to be made at once. More particularly, predetermined mask subset may be fabricated so as to implement transistors/gates/flipflops/memories, etc. Additional metal layers may be added, specific to a particular design, to connect the transistors/gates/flipflops/memories to perform the functionality described herein.

In various embodiments, additional elements may be added to the master slice, such as hard processor cores (ARM cores), which may not be as efficient to add ARM cores on top within metal layers, but may be built in physically exact way to achieve appropriate frequencies, etc. Additionally, one or more embedded processor cores may be established inside the master slice. May include pins that can be connected to additional logic defined for the processing, such as for the mapper, aligner, sorter, and additional accelerated functions for processing, such as in a Bio-IT functions. Other functionalities in the master slice may include base calling logic, such as for sequencing technologies. In various instances, the integrated circuit, e.g., structured ASIC, may be integrated in to the automated, e.g., next-gen, sequencer, and may receive one or more FASTQ files directly there from. Such an integrated circuit can involve any of the primary processing of next-generation DNA sequencers, such as image processing, signal processing, and/or base calling, such as in the master slice. In such instances, one or more of the BioIT functions may be put into one or more configurable layers (e.g., inexpensive mask layers), such as which may include base calling logic, which may be put into the master slice, then one or more complete sASICs with one or more of the mapper, aligner, sorter, etc., may be formed in the configurable layers. One or more masking layers may also be included, so as to create different functionality.

As indicated above, in various instances a chip of the disclosure may be configured as an expansion card, such as where the chip includes a PCIe bus and is positioned so as to be in communication with one or more memories, such as being surrounding by memories, such as being substantially surrounded by memories, such as being entirely surrounded by memories. In various embodiments, the chip may be a dense and/or fast FPGA chip that in various instances, may be convertible to an ASIC or an sASIC. In various instances, the chip may be a structured ASIC that is convertible into an ASIC. In some instances, the chip may be an ASIC.

As indicated above, the modules herein disclosed may be implemented in the hardware of the chip, such as by being hardwired therein, and in such instances their implementation may be such that their functioning may take place at a faster speed as compared to when implemented in software, such as where there are minimal instructions to be fetched, read, and/or executed. Hence, given the unique hardware implementation, the modules of the disclosure may function directly in accordance with their operations parameters, such as without needing to fetch, read, and/or execute instructions. Additionally, memory requirements and processing times may be reduced, such as where the communications within chip is via files rather than through accessing a memory. Of course, in some instances, the chip and/or card may be sized so as to include more memory, such as more on board memory, so as to enhance parallel processing capabilities, thereby resulting in even faster processing speeds. For instance, in certain embodiments, a chip of the disclosure may include an embedded DRAM, so that the chip does not have to rely on external memory, which would therefore result in a further increase in processing speed, such as where a Burrows-Wheeler algorithm may be employed, instead of a hash table and hash function, which may in various instances, rely on external, e.g., host memory. In such instances, the running of the entire pipeline can be accomplished in 6 minutes or less, such as from start to finish.

As indicated above, there are various different points where any given module can be positioned on the hardware, or be positioned remotely therefrom, such as on a server accessible on the cloud. Where a given module is positioned on the chip, e.g., hardwired into the chip, its function may be performed by the hardware, however, where desired, the module may be positioned remotely from the chip, at which point the platform may include the necessary instrumentality for sending the relevant data to a remote location, such as a server accessible via the cloud, so that the particular module's functionality may be engaged for further processing of the data, in accordance with the user selected desired protocols. Accordingly, part of the platform may include a web-based interface for the performance of one or more tasks pursuant to the functioning of one or more of the modules disclosed herein. For instance, where mapping, alignment, and/or sorting are all modules that may occur on the chip, in various instances, one or more of local realignment, duplicate marking, base quality core recalibration, and/or variant calling may take place on the cloud.

Additionally, in various embodiments, all of mapping, aligning, and sorting, may take place on the chip, and local realignment, duplicate marking, and/or base quality score recalibration may, in various embodiments, also take place on the chip, and in various instances, various compression protocols, such as BAM and CRAM, may also take place on the chip. However, once the data is compressed it may be sent up to the cloud, such as for the performance of the variant calling module. This might be useful especially given the fact that variant calling can be a moving target, e.g., there is not one standardized agreed upon algorithm that the industry uses. Hence, different algorithms can be employed to achieve a different type of result, and as such having a cloud based module for the performance of this function may be useful for allowing the flexibility to select which algorithm is useful at any particular given moment, and also as for serial and/or parallel processing. Accordingly, any one of the modules disclosed herein can be implemented as either hardware, e.g., on the chip, or software, e.g., on the cloud, but in certain embodiments, all of the modules may be configured so that their function may be performed on the chip, or all of the modules may be configured so that their function may be performed remotely, such as on the cloud, or there will be a mixture of modules wherein some are positioned on the chip and some are positioned on the cloud. Further, as indicated, in various embodiments, the chip itself may be configured so as to function in conjunction with, and in some embodiments, in immediate operation with a genetic sequencer.

More specifically, in various embodiments, an apparatus of the disclosure may be a chip, such as a chip that is configured for processing genomics data, such as by employing a pipeline of data analysis modules. According, as can be seen with respect to FIG. 1, a genomics pipeline processor chip 100 is provided along with associated hardware of a genomics pipeline processor system 10. The chip 100 has one or more connections to external memory 102 (at "DDR3 Mem Controller"), and a connection 104 (e.g., "PCIe Interface") to the outside world, such as a host computer 106, for example. A crossbar 108 (e.g., switch) provides access to the memory interfaces to various requestors. DMA engines 110 transfer data at high speeds between the host and the processor chip's 100 external memories 102 (via the crossbar 108), and/or between the host and a central controller 112. The central controller 112 controls chip operations, especially coordinating the efforts of multiple processing engines. The processing engines are formed of a set of hardwired digital logic circuits that are interconnected by physical electrical interconnects, and are organized into engine clusters 114. In some implementations, the engines in one cluster share one crossbar port, via an arbiter. The central controller 112 has connections to each of the engine clusters. Each engine cluster 114 has a number of processing engines for processing genomic data, including a mapper 120 (or mapping module), an aligner 122 (or aligning module), and a sorter 124 (or sorting module). An engine cluster 114 can include other engines or modules, as well.

In accordance with one data flow model consistent with implementations described herein, the host sends commands and data via the DMA engines 110 to the central controller 112, which load-balances the data to the processing engines. The processing engines return processed data to the central controller 112, which streams it back to the host via the DMA engines 110. This data flow model is suited for mapping and alignment.

In accordance with an alternative data flow model consistent with implementations described herein, the host streams data into the external memory, either directly via DMA engines 110 and the crossbar 108, or via the central controller 112. The host sends commands to the central controller 112, which sends commands to the processing engines, which instruct the processing engines as to what data to process. The processing engines access input data from the external memory, process it, and write results back to the external memory, reporting status to the central controller 112. The central controller 112 either streams the result data back to the host from the external memory, or notifies the host to fetch the result data itself via the DMA engines 110.

Figure 2:
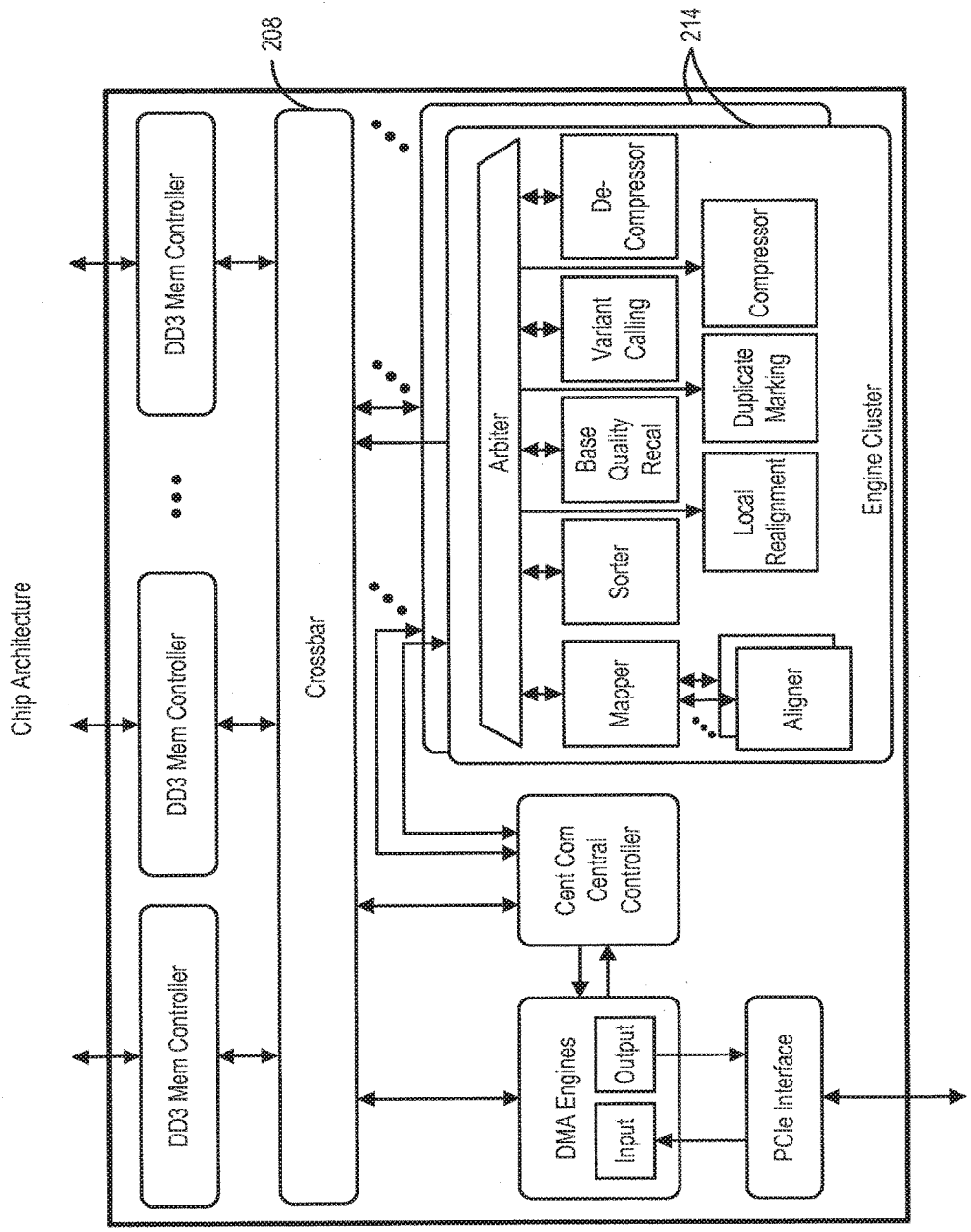
FIG. 2 is a block diagram of a hardware processor architecture in accordance with another implementation.

FIG. 2 illustrates a genomics pipeline processor system 20, showing a full complement of processing engines inside an engine cluster 214. The pipeline processor system 20 may include one or more engine clusters 214. In some implementations, the pipeline processor system 20 includes four our more engine clusters 214. The processing engines or processing engine types can include, without limitation, a mapper, an aligner, a sorter, a local realigner, a base quality recalibrater, a duplicate marker, a variant caller, a compressor and/or a decompressor. In some implementations, each engine cluster 214 has one of each processing engine type. Accordingly, all processing engines of the same type can access the crossbar 208 simultaneously, through different crossbar ports, because they are each in a different engine cluster 214. Not every processing engine type needs to be formed in every engine cluster 214. Processing engine types that require massive parallel processing or memory bandwidth, such as the mapper (and attached aligner(s)) and sorter, may appear in every engine cluster of the pipeline processor system 20. Other engine types may appear in only one or some of the engine clusters 214, as needed to satisfy their performance requirements or the performance requirements of the pipeline processor system 20.

Figure 3:
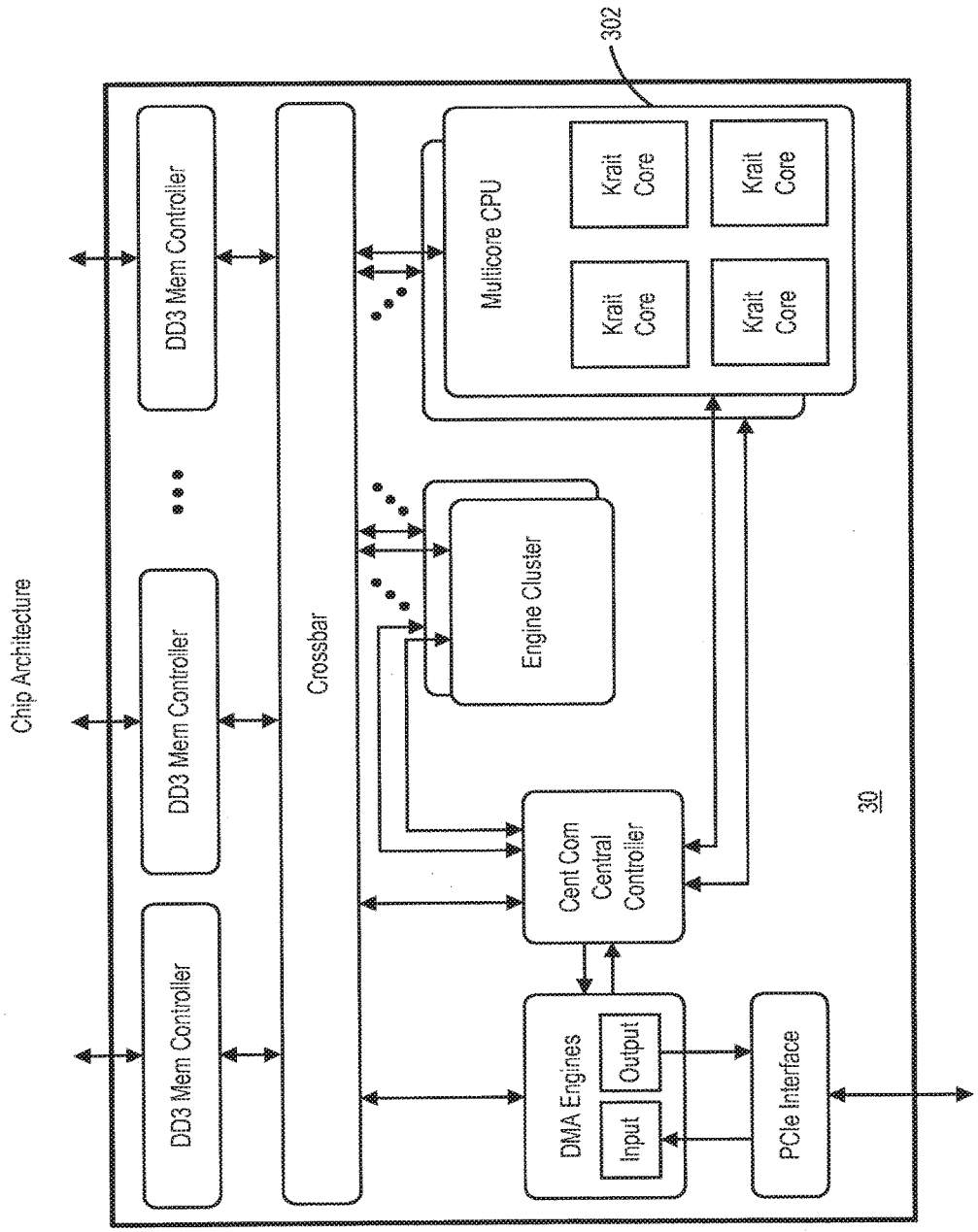
FIG. 3 is a block diagram of a hardware processor architecture in accordance with yet another implementation.

FIG. 3 illustrates a genomics pipeline processor system 30, showing, in addition to the engine clusters described above, one or more embedded central processing units (CPUs) 302. Examples of such embedded CPUs include SNAPDRAGON or standard ARM cores. These CPUs execute fully programmable bio-IT algorithms, such as advanced variant calling. Such processing is accelerated by computing functions in the engine clusters, which can be called by the CPU cores 302 as needed. Furthermore, even engine-centric processing, such as mapping and alignment, can be managed by the CPU cores 302, giving them heightened programmability.

Figure 4:
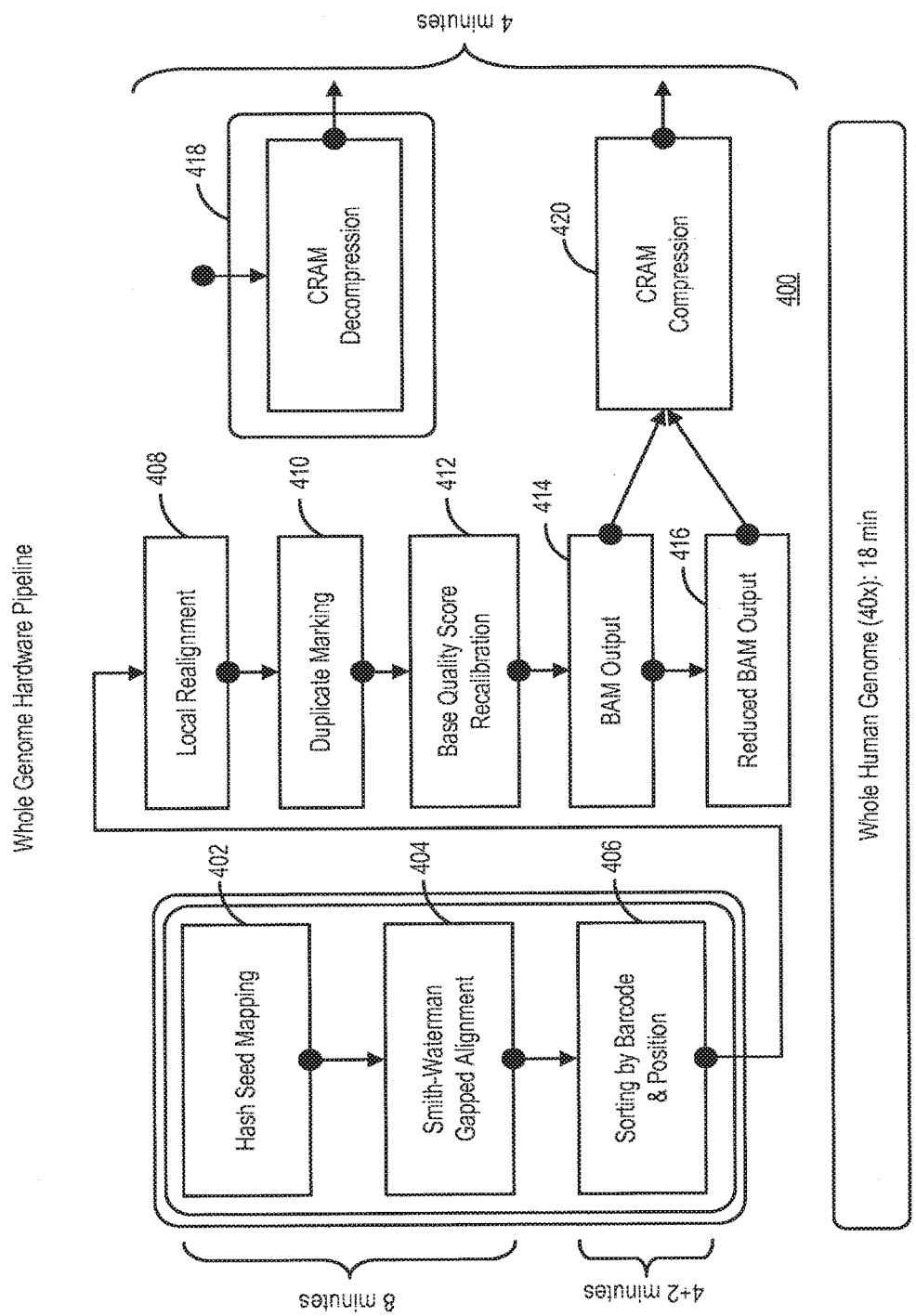
FIG. 4 illustrates a genetic sequence analysis pipeline.

FIG. 4 illustrates a processing flow for a genomics pipeline processor system and method. In some preferred implementations, there are three passes over the data. The first pass includes mapping 402 and alignment 404, with the full set of reads streamed through the engines. The second pass includes sorting 406, where one large block to be sorted (e.g., a substantial portion or all reads previously mapped to a single chromosome) is loaded into memory, sorted by the processing engines, and returned to the host. The third pass includes downstream stages (local realignment 408, duplicate marking 410, base quality score recalibration (BQSR) 412, BAM output 414, reduced BAM output 416, and/or CRAM compression 418). The steps and functions of the third pass may be done in any combination or subcombination, and in any order, in a single pass. A virtual pipeline architecture, such as described above, is used to stream reads from the host into circular buffers in memory, through one processing engine after another in sequence, and back out to the host. In some implementations, CRAM decompression can be a separate streaming function. In some implementations, the BAM output 414, reduced BAM output 416, and/or CRAM compression 418 can be replaced with variant calling, compression and decompression.

Figure 5A:
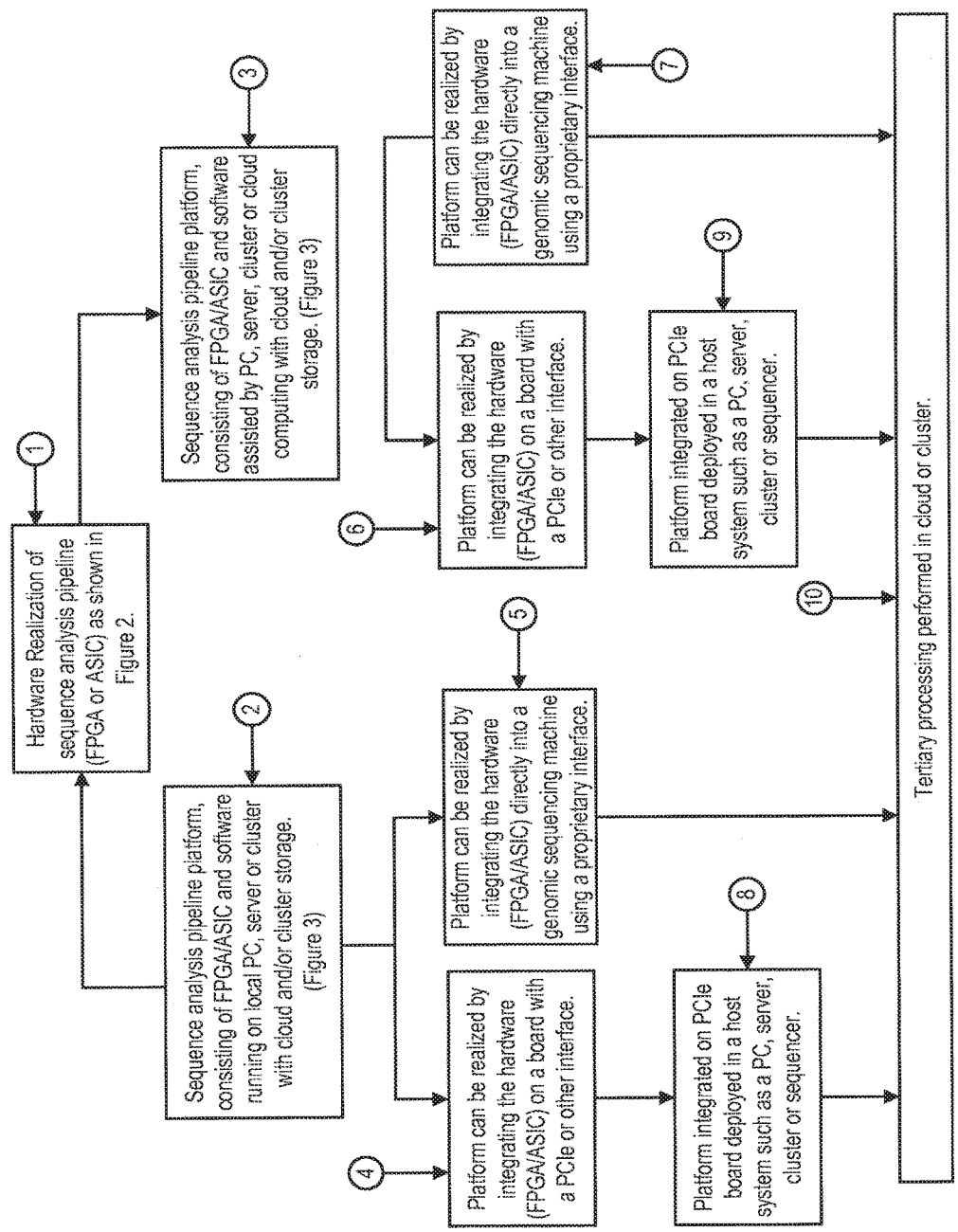
FIG. 5A illustrates processing steps using a genetic sequence analysis hardware platform.
Figure 5B:
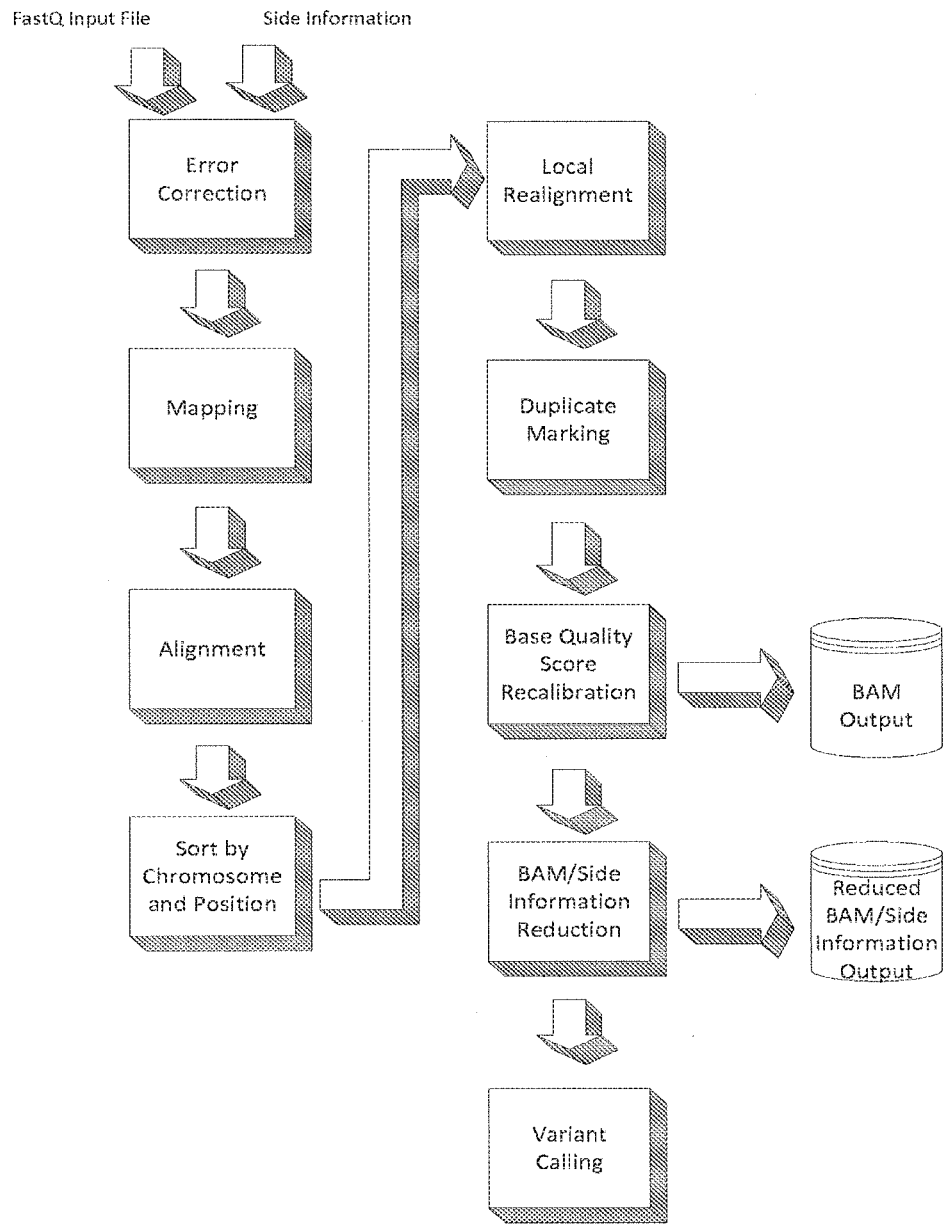
FIGS. 5B and 5C illustrate a number of blocks and/or modules to do sequence analysis.

FIG. 5A shows a general block diagram of the current invention. In Block 1, a hardware implementation of a sequence analysis pipeline is described. This can be done in a number of different ways such as an FPGA or ASIC or structured ASIC implementation. The functional blocks that are implemented by the FPGA or ASIC or structured ASIC are shown in FIGS. 5A and 5B. FIGS. 5A and 5B include a number of blocks and/or modules to do sequence analysis. The input to the hardware realization can be a FASTQ file, but is not limited to this format. In addition to the FASTQ file, the input to the FPGA or ASIC or structured ASIC consists of side information, such as Flow Space Information from technology such as the Ion Torrent. The modules in FIG. 5B illustrate the following elements: Error Correction, Mapping, Alignment, Sorting, e.g., by chromosome and/or position, Local Realignment, Duplicate Marking, Base Quality Recalibration, BAM and Side Information reduction (which may lead to BAM Output and/or Reduced BAM/Side Information Output), and variant calling.

As described herein one or more of the aforementioned modules may be configurable so as to perform a secondary processing protocol, such as to perform one or more of the following functions in accordance with one or more of the following parameters: mapping, which mapping may be configurable in accordance with the following seed parameters: primary seed length, maximum extended seed length, density, and pattern of seeds to extract from each read. Performing a hash function, which hash function may be configurable in accordance with the following hash table parameters: primary/secondary hash table base addresses, primary/secondary hash table sizes, and primary/secondary hash function (from chosen CRC polynomial). Seed chaining, which seed chaining may be configurable in accordance with the following seed chaining parameters: old' age threshold, 'ancient' (maximum) age threshold, diameter limit, and radius limit. Seed chain filtering, which seed chain filtering may be tuned more or less aggressively.

Additionally, "perfect alignment" optimization parameters may be employed, enabling this feature, such as allowing 1-base gaps within a read and allowing 1-base gaps at beginning and/or end of a read. Reference genome parameters may also be configured in accordance with reference genome base address, reference genome length, number of sequences in reference genome, and start offset of each reference sequence. Additionally, Smith-Waterman (or Needleman-Wunsch) scoring parameters can be configured in accordance with score for matching reference 'N,' gap extension penalty, unclipped alignment score bonus, global alignment mode (e.g., Needleman-Wunsch). A Table of scoring parameters, as a function of read base quality score, may be configured with respect to match score, mismatch penalty, match score vs. 2-base IUB code in reference, mismatch penalty vs. 2-base IUB code in reference, and gap open penalty.

In various instances, the system may be run in map-only mode (intermediate output from mapper, without aligning). It may be run with automatic wavefront steering, such as in accordance with, score delta, for computing threshold below maximum score, used to select scores to try to center. Further, paired end (or mate-pair) parameters may be set to configure the system, such as in accordance with expected orientation (Forward-Reverse=FR, RF, FF), mean insert size, minimum/maximum insert size for properly paired, minimum/maximum insert size to avoid rescue alignment, and rescue alignment modes, e.g., no rescues, rescue from all seed chains if zero pairs found, rescue from each unpaired seed chain, rescue from all seed chains, additionally configurable in accordance with one or more of the number of rescue alignment swaths, position step between rescue alignment swaths, and table of score penalties for observed insert size bins.

Further, mapping quality (MAPQ) estimation may also be configured with respect to the following parameters: coefficient to multiply by (best-suboptimal) score difference, maximum MAPQ to clip, minimum alignment score to allow, also may be used as a floor on suboptimal score for computing MAPQ. Additionally, alignment reporting parameters may be configured in accordance with maximum number of supplementary (chimeric) alignments to report, maximum number of secondary (suboptimal) alignments to report, whether to flag supplementary alignments as secondary, and flags to use hard clipping instead of soft clipping, such as for: primary alignments, supplementary alignments, and/or secondary alignments.

These modules can be present inside, or implemented by, the hardware, or may be implemented in software, but some of these blocks may be omitted or other blocks added to achieve the purpose of realizing a sequence analysis pipeline. Blocks 2 and 3 of FIG. 5A describe two alternatives of a sequence analysis pipeline platform. The sequence analysis pipeline platform comprising an FPGA or ASIC or structured ASIC and software assisted by a host (i.e., PC, server, cluster or cloud computing) with cloud and/or cluster storage. In block 2 of FIG. 5A, the sequence analysis pipeline hardware (and/or software) implements one or more, e.g., all, of the modules of FIG. 5B, while in block 3 of FIG. 5A, the sequence analysis hardware implements only some of the modules of FIG. 5B. For instance, the variant calling module of FIG. 5B can be performed by the host or via a network, e.g., in the cloud.

Figure 5C:
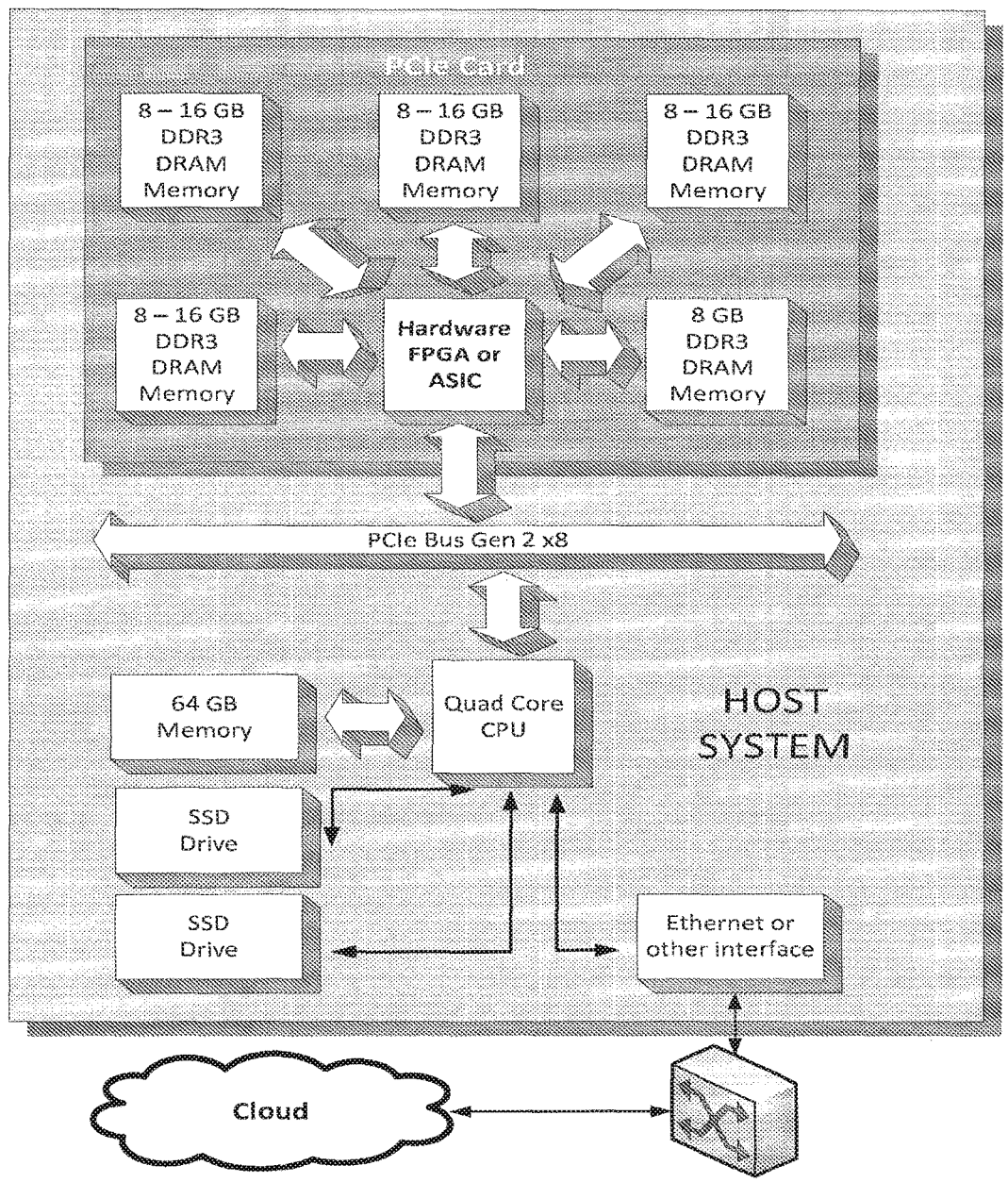

Blocks 4-7 describe different interfaces that the sequence analysis pipeline can have. In Blocks 4 and 6 the interface can be a PCIe interface, but is not limited to a PCIe interface. In Blocks 5 and 7 the hardware (FPGA or ASIC or structured ASIC) can be directly integrated into a sequencing machine. Blocks 8 and 9 describe the integration of the hardware sequence analysis pipeline integrated into a host system such as a PC, server cluster or sequencer. FIG. 5C shows an implementation of these modules. For instance, FIG. 5C illustrates an exemplary sequence analysis pipeline platform that includes a FPGA or ASIC or sASIC and/or software assisted by a host (PC, server, cluster, or cloud computing) with cloud and/or cluster storage. More particularly, FIG. 5C illustrates an implementation of these modules. For example, surrounding the hardware FPGA or ASIC or sASIC are lots of DDR3 memory elements and a PCIe interface. The board with the FPGA/ASIC/sASIC connects to a host computer, comprising a host CPU, that could be either a low power CPU such as an ARM, SNAPDRAGON, INTEL, ATOM, TI OMAP processors, such as the INTEL XEON, or any other processor. Also in the host system could be a GPU processor such as the NVIDIA GPUs. The host may also have hard drives such as SSD and memory.

Accordingly, surrounding the hardware FPGA or ASIC or structured ASIC are lots of DDR3 memory elements and a PCIe interface. The board with the FPGA/ASIC/sASIC connects to a host computer, consisting of a host CPU, that could be either a low power CPU such as an ARM, SNAPDRAGON, or any other processor. Block 10 illustrates a hardware sequence analysis pipeline API that can be accessed by third party applications to perform tertiary analysis.

Figure 6:
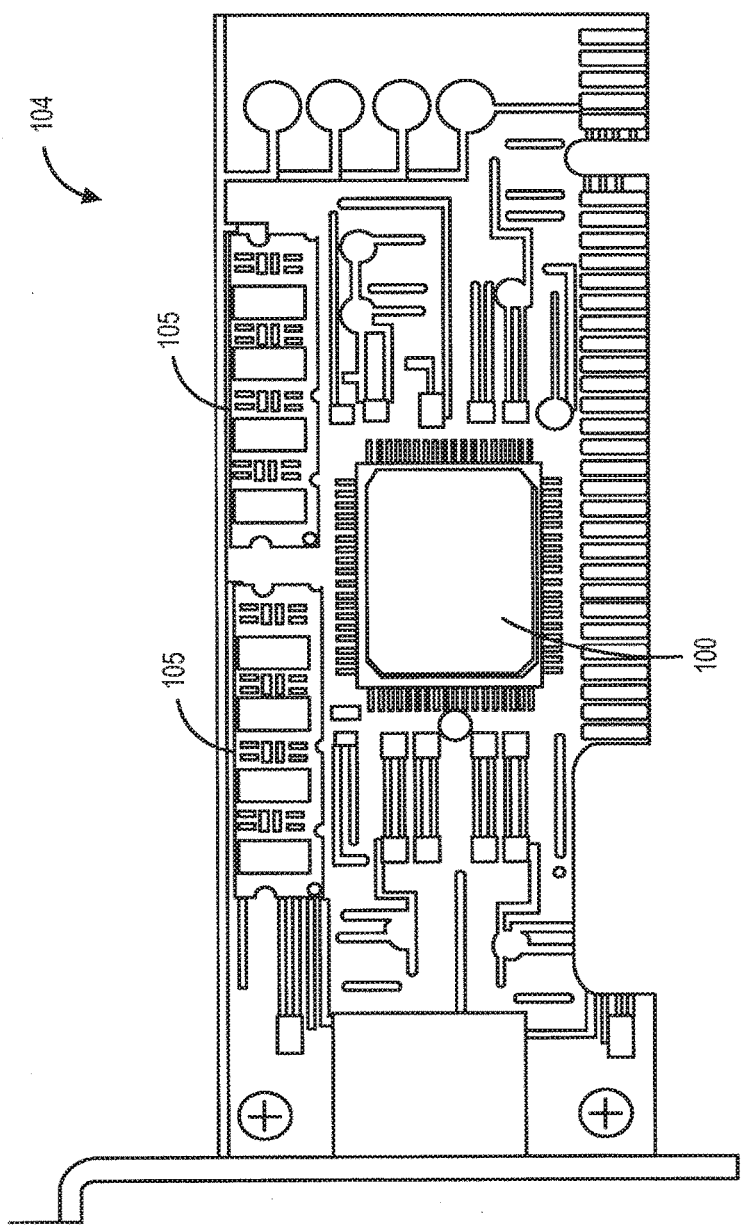
FIG. 6 illustrates an apparatus in accordance with an implementation.
Figure 7:
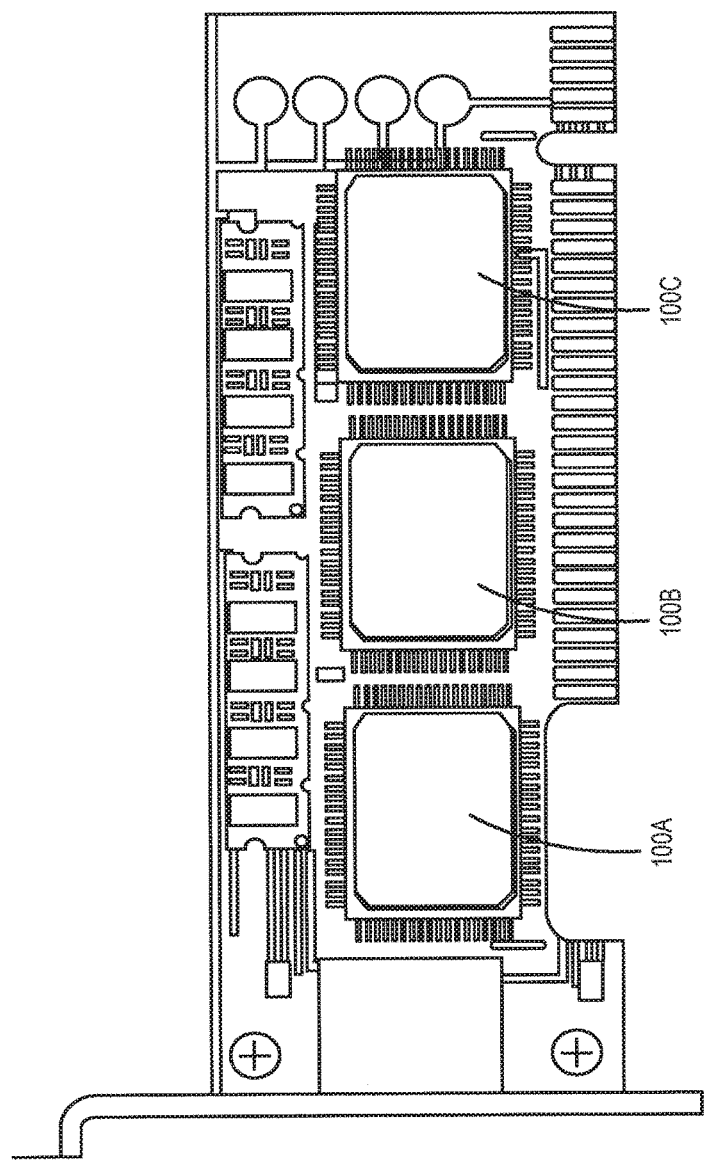
FIG. 7 illustrates an apparatus in accordance with an alternative implementation.

Accordingly, in various embodiments, an apparatus of the disclosure may include a computing architecture, such as embedded in a silicon application specific integrated circuit (ASIC) 100 as seen in FIGS. 6 and 7. The ASIC 100 can be integrated into a printed circuit board (PCB) 104, such as a Peripheral Component Interface—Express (PCIe) card, that can be plugged into a computing platform. In various instances, as shown in FIG. 6, the PCIe card 104 may include a single ASIC 100, which ASIC may be surrounded by local memories 105, however, in various embodiments, the PCIe card 104 may include a plurality of ASICs 100A, 100B and 100C. In various instances, the PCI card may also include a PCIe bus. This PCIe card 104 can be added to a computing platform to execute algorithms on extremely large data sets. Accordingly, in various instances, the overall work flow of genomic sequencing involving the ASIC may include the following: Sample preparation, Alignment (including mapping and alignment), Variant analysis, Biological Interpretation, and/or Specific Applications.

Hence, in various embodiments, an apparatus of the disclosure may include a computing architecture that achieves the high performance execution of algorithms, such as mapping and alignment algorithms, that operate on extremely large data sets, such as where the data sets exhibit poor locality of reference (LOR). These algorithms are designed to reconstruct a whole genome from millions of short read sequences, from modern so-called next generation sequencers, require multi-gigabyte data structures that are randomly accessed. Once reconstruction is achieved, as described herein above, further algorithms with similar characteristics are used to compare one genome to libraries of others, do gene function analysis, etc.

There are typically two major approaches in use, general purpose multicore CPUs and general purpose Graphic Processing Units (GPGPUs). In such an instance each CPU in a multicore system may have a classical cache based architecture, wherein instructions and data are fetched from a level 1 cache (L1 cache) that is small but has extremely fast access. Multiple L1 caches may be connected to a larger but slower shared L2 cache. The L2 cache may be connected to a large but slower DRAM (Dynamic Random Access Memory) system memory, or may be connected to an even larger but slower L3 cache which may then connected to DRAM. An advantage of this arrangement may be that applications in which programs and data exhibit locality of reference behave nearly as if they are executing on a computer with a single memory as large as the DRAM but as fast as the L1 cache. Because full custom, highly optimized CPUs operate at very high clock rates, e.g., 2 to 4 GHz, this architecture may be essential to achieving good performance.

Further, GPGPUs may be employed to extend this architecture, such as by implementing very large numbers of small CPUs, each with their own small L1 cache, wherein each CPU executes the same instructions on different subsets of the data. This is a so called SIMD (Single Instruction stream, Multiple Data stream) architecture. Economy is gained by sharing the instruction fetch and decode logic across a large number of CPUs. Each cache has access to multiple large external DRAMs via an interconnection network. Assuming the computation to be performed is highly parallelizable, GPGPUs have a significant advantage over general purpose CPUs due to having large numbers of computing resources. Nevertheless, they still have a caching architecture and their performance is hurt by applications that do not have a high enough degree of locality of reference. That leads to a high cache miss rate and processors that are idle while waiting for data to arrive from the external DRAM.

For instance, in various instances, Dynamic RAMs may be used for system memory because they are more economical than Static RAMs (SRAM). The rule of thumb used to be that DRAMs had 4× the capacity for the same cost as SRAMs. However, due to declining demand for SRAMs in favor of DRAMs, that difference has increased considerably due to the economies of scale that favor DRAMs which are in high demand. Independent of cost, DRAMs are 4× as dense as SRAMs laid out in the same silicon area because they only require one transistor and capacitor per bit compared to 4 transistors per bit to implement the SRAM's flip-flop. The DRAM represents a single bit of information as the presence or absence of charge on a capacitor. A problem with this arrangement is that the charge decays over time, so it has to be refreshed periodically. The need to do this has led to architectures that organize the memory into independent blocks and access mechanisms that deliver multiple words of memory per request. This compensates for times when a given block is unavailable while being refreshed. The idea is to move a lot of data while a given block is available. This is in contrast to SRAMs in which any location in memory is available in a single access in a constant amount of time. This characteristic allows memory accesses to be single word oriented rather than block oriented. DRAMs work well in a caching architecture because each cache miss leads to a block of memory being read in from the DRAM. The theory of locality of reference is that if just accessed word N, then probably going to access words N+1, N+2, N+3 and so on, soon.

Figure 8:
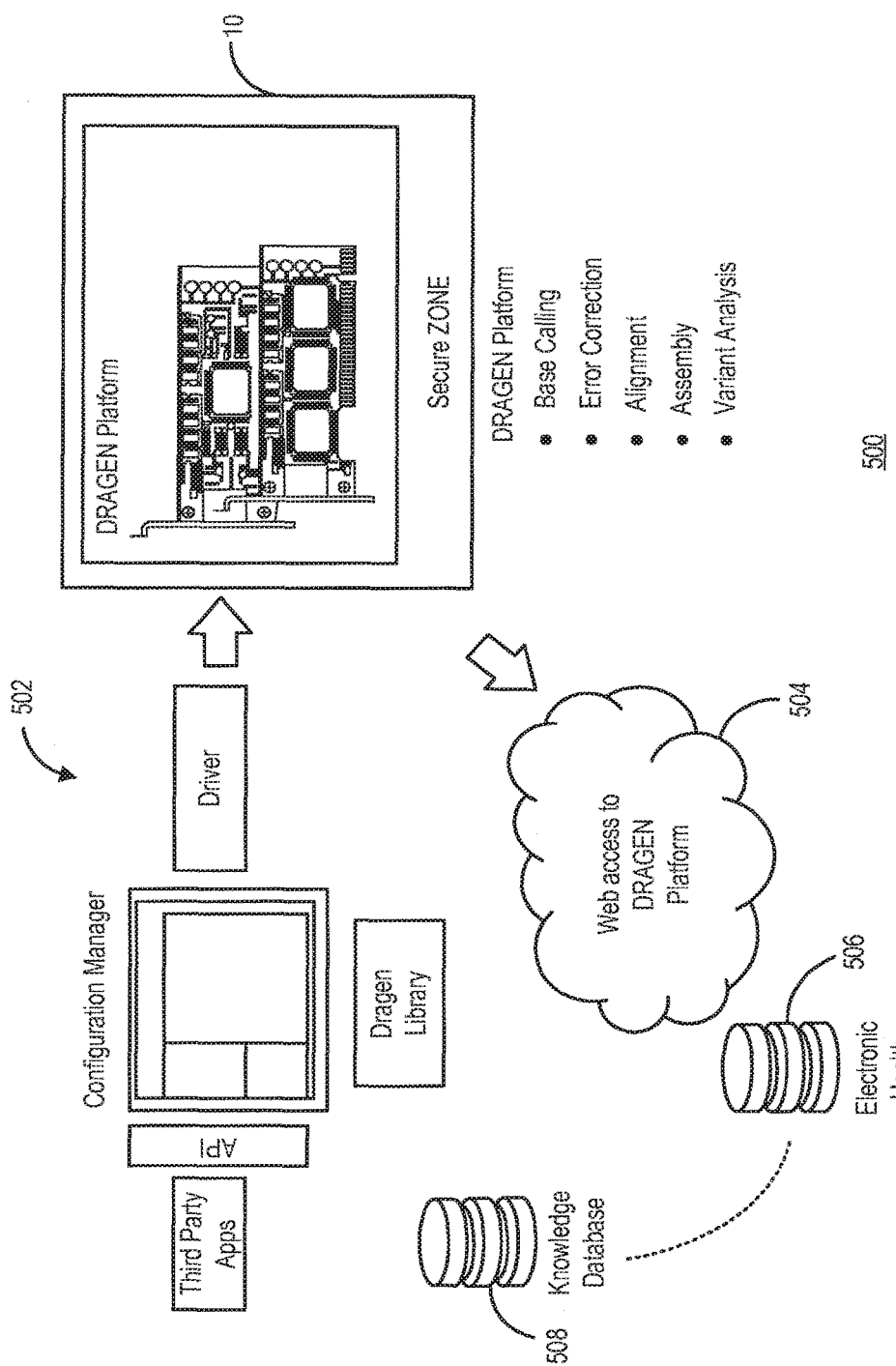
FIG. 8 illustrates a genomics processing system in accordance with an implementation.

FIG. 8 illustrates a system 500 for executing a sequence analysis pipeline on genetic sequence data. The system 500 includes a configuration manager 502 that includes a computing system. The computing system of the configuration manager 502 can include a personal computer or other computer workstation, or can be implemented by a suite of networked computers. The configuration manager 502 can further include one or more third party applications connected with the computing system by one or more APIs, which, with one or more proprietary applications, generate a configuration for processing genomics data from a sequencer or other genomics data source. The configuration manager 502 further includes drivers that load the configuration to the genomics pipeline processor system 10. The genomics pipeline processor system 10 can output result data to, or be accessed via, the Web 504 or other network, for storage of the result data in an electronic health record 506 or other knowledge database 508.

As discussed in several paces herein above, the chip implementing the genomics pipeline processor can be connected or integrated in a sequencer. The chip can also be connected or integrated on an expansion card, e.g. PCIe, and the expansion card can by connected or integrated in a sequencer. In other implementations, the chip can be connected or integrated in a server computer that is connected to a sequencer, to transfer genomic reads from the sequencer to the server. In yet other implementations, the chip can be connected or integrated in a server in a cloud computing cluster of computers and servers. A system can include one or more sequencers connected (e.g. via Ethernet) to a server containing the chip, where genomic reads are generated by the multiple sequencers, transmitted to the server, and then mapped and aligned in the chip.

For instance, in general next generation DNA sequencer (NGS) data pipelines, the primary analysis stage processing is generally specific to a given sequencing technology. This primary analysis stage functions to translate physical signals detected inside the sequencer into "reads" of nucleotide sequences with associated quality (confidence) scores, e.g. FASTQ format files, or other formats containing sequence and usually quality information. After such a format is achieved, secondary analysis proceeds, as described herein, to determine the content of the sequenced sample DNA (or RNA etc.), such as by mapping and aligning reads to a reference genome, sorting, duplicate marking, base quality score recalibration, local re-alignment, and variant calling. Tertiary analysis may then follow, to extract medical or research implications from the determined DNA content.

However, primary analysis, as mentioned above, is often quite specific in nature to the sequencing technology employed. In various sequencers, nucleotides are detected by sensing electrical charges, electrical currents, or radiated light. Some primary analysis pipelines often include: Signal processing to amplify, filter, separate, and measure sensor output; Data reduction, such as by quantization, decimation, averaging, transformation, etc.; Image processing or numerical processing to identify and enhance meaningful signals, and associate them with specific reads and nucleotides (e.g. image offset calculation, cluster identification); Algorithmic processing and heuristics to compensate for sequencing technology artifacts (e.g. phasing estimates, cross-talk matrices); Bayesian probability calculations; Hidden Markov models; Base calling (selecting the most likely nucleotide at each position in the sequence); Base call quality (confidence) estimation, and the like.

Primary analysis can be extremely computationally intensive, sometimes as intensive as secondary analysis. For instance, in existing sequencing technologies, primary analysis often utilizes FPGAs and/or GPUs to accelerate processing beyond CPU capabilities. But these accelerated functions can be performed much more efficiently in custom integrated circuitry, such as that described herein. For example, they can be implemented in a structured ASIC using the configurable metal layers, as they do not require as much physical layout precision as embedded processor cores; however, the massively parallel computation implemented in large FPGAs and GPUs may be difficult to fit in the configurable structured ASIC resources. An alternative is to implement primary processing acceleration logic in the master slice of a structured ASIC, taking advantage of the standard cell space efficiency in the master slice.

A reason that secondary processing functions may be implemented in a structured ASIC configurable metal layers is that secondary genomic data processing algorithms are still evolving via active research. It may be therefore beneficial to be able to inexpensively produce a freshly updated structured ASIC design periodically, such as every year or every two years, to utilize the latest algorithms. By contrast, primary analysis algorithms currently employed are more mature, the necessary processing having been researched and defined by the respective sequencer manufacturers. Even to the extent it is still subject to change, the algorithms are more generic signal and numerical processing than is the case in secondary analysis, so that appropriate configurability and micro-coding of primary processing acceleration modules can make them flexible enough to accommodate significant changes. If present, embedded processor cores increase this flexibility even further. For these reasons, it is reasonable to design primary processing acceleration modalities into a structured ASIC master slice, as herein described.

It is also advantageous to integrate primary processing acceleration and secondary processing acceleration in a single integrated circuit (standard cell or structured ASIC), with or without embedded processors. This may be beneficial because sequencers produce data requiring both primary and secondary analysis, and integrating them in a single device is most efficient in terms of cost, space, power, and resource sharing. If embedded processors are also present, they can be leveraged to increase the speed and flexibility of both primary and secondary processing.

These three components—primary accelerators, secondary accelerators, and embedded processors—can be implemented in a structured ASIC master slice, and/or using configurable metal layers, in any combination. All three could be in the master slice, or all three could use configurable metal layers, or any one or two of them could be in the master slice, and the others use configurable metal layers. In any of these configurations, all three can communicate with each other, in any combination, directly and/or via memory, and cooperate in common tasks. One advantageous configuration is to implement primary acceleration and embedded processors in the master slice, and implement secondary acceleration using configurable metal layers.

For instance, in accordance with the above, a system for executing a sequence analysis pipeline on genetic sequence data may be provided, such as where the system includes an electronic data source, such as that which provides digital signals representing a plurality of reads of genomic data, each of the plurality of reads of genomic data including a sequence of nucleotides; a memory, e.g., for storing one or more genetic reference sequences and/or an index of the one or more genetic reference sequences; and an integrated circuit, such as an FPGA or a structured application specific integrated circuit (ASIC), that may be formed of a set of mask-programmable, hardwired digital logic circuits that are interconnected, such as by a plurality of physical electrical interconnects. In such an instance, the one or more of the plurality of physical electrical interconnects may include an input to the integrated circuit, e.g., FPGA or structured ASIC, that may be connected with the electronic data source for receiving the plurality of reads of genomic data. The one or more of the plurality of physical electrical interconnects may further include a memory interface, e.g., for the FPGA or structured ASIC, to access the memory. Further, the hardwired digital logic circuits may be arranged as a set of processing engines, such as where each processing engine may be formed of a subset of the hardwired digital logic circuits so as to perform one or more steps, such as one or more steps in a sequence analysis pipeline on the plurality of reads of genomic data, for instance, where each subset of the hardwired digital logic circuits may be in a wired configuration to perform the one or more steps in the sequence analysis pipeline, such as where the wired configuration is non-volatile and/or established upon manufacture of the FPGA or structured ASIC.

In various of such instances, the set of processing engines may include one or more of a mapping module, such as in the wired configuration, such as to access, according to at least some of the sequence of nucleotides in a read of the plurality of reads, the index of the one or more genetic reference sequences, e.g., from the memory, via the memory interface so as to map the read to one or more segments of the one or more genetic reference sequences based on the index; an alignment module, which also may be in the wired configuration to access the one or more genetic reference sequences from the memory via the memory interface so as to align the read to one or more positions in the one or more segments of the one or more genetic reference sequences from the mapping module; and may include a sorting module, which also may be in the wired configuration, so as to sort each aligned read according to the one or more positions in the one or more genetic reference sequences. It is to be noted that one or more of these modules, e.g., mapping, aligning, and/or sorting may be included or omitted, or substituted for, or added along with any other module in the sequence analysis pipeline, as described herein above, any module of which may be in the wired configuration or implemented in software either on the chip or in the host. Further, where the system includes an index, such as an index of the one or more genetic reference sequences, the index may further include a hash table, and the mapping module may apply a hash function to the at least some of the sequence of nucleotides so as to access the hash table of the index. Additionally, one or more of the plurality of physical electrical interconnects may include an output from the FPGA or structured ASIC for communicating result data from the mapping module and/or the alignment module and/or sorting.

In certain embodiments, the FPGA or structured ASIC and the memory may housed on an expansion card, such as a peripheral component interconnect (PCI) card, which PCI card may be part of a sequencer, e.g., a "next-gen" sequencer, as described herein and below. Hence, in various embodiments, the system may include a sequencer, such as where the sequencer includes the electronic data source that provides the digital signals representing the plurality of reads of genomic data. Further, in various instances, the set of processing engines may include a base-calling engine so as to analyze digital measurements from the sequencer to determine a most likely nucleotide at each position sequenced by the sequencer, and to estimate a confidence of the most likely nucleotide. Hence, in such an instance, the system may include one or more of signal processing and/or image processing functionality, which may be in the wired configuration upon the FPGA, ASIC, or structured ASIC, or may be performed by software associated therewith.

Accordingly, in view of the above, in various embodiments, the FPGA or structured ASIC may include a master slice that may include at least some of the hardwired digital logic circuits and may further include one or more configurable metal layers formed on the master slice, such as where each of the one or more configurable metal layers may have at least some of the plurality of physical electrical interconnects that interconnect the at least some of the hardwired digital logic circuits to form at least one of the set of processing engines. For instance, in some embodiments, a portion of the set of digital logic circuits may be hardwired in the master slice, such as one or more embedded processor cores. Hence, one or more of the processing engines of the set of processing engines may be connected to the one or more embedded processor cores such as via the one or more configurable metal layers that may be formed on the master slice.

Accordingly, in various embodiments, a structured application-specific integrated circuit (ASIC) for analyzing genetic sequence data from an electronic data source that provides digital signals representing a plurality of reads of genomic data, such as where each of the plurality of reads of genomic data may include a sequence of nucleotides, and using a memory, e.g., a memory storing one or more genetic reference sequences associated with genomic data and/or an index of the one or more genetic reference sequences, may be provided. In various instances, the structured ASIC may include a master slice that includes a set of digital logic circuits; and the sASIC may include one or more configurable metal layers that may be formed on the master slice, such as where each of the one or more configurable metal layers may have a set of wired connections, such as where the wired connections of the one or more configurable metal layers may be arranged to interconnect a subset of the digital logic circuits so as to form a set of processing engines. In such instances, the set of processing engines may include one or more of a mapping engine, such as to access the index of the one or more genetic reference sequences from the memory so as to map the read to one or more segments of the one or more genetic reference sequences based on the index; and may include an alignment engine, such as to access the one or more genetic reference sequences from the memory to align the read to one or more positions in the one or more segments of the one or more genetic reference sequences from the mapping engine; and may further include a sorting engine, such as to access the one or more aligned reads from the memory so as to sort each aligned read according to the one or more positions in the one or more genetic reference sequences.

In certain embodiments, a portion of the set of digital logic circuits may be hardwired in the master slice, such as to form a base calling engine, so as to analyze the genetic sequence data from the electronic data source to determine a most likely nucleotide at each position sequenced by the sequencer, and to estimate a confidence of the most likely nucleotide. In additional embodiments, a portion of the set of digital logic circuits may be hardwired in the master slice such as one or more embedded processor cores. Additionally, one or more of the processing engines of the set of processing engines may be connected to the one or more embedded processor cores via the one or more configurable metal layers formed on the master slice. In certain embodiments, the set of processing engines may include a primary analysis pipeline engine, such as where the primary analysis pipeline engine executes on the genomic data one or more of: signal processing, image processing, base calling, and base call quality estimation.

In various embodiments, a portion of the set of digital logic circuits in the master slice may be hardwired as a primary analysis pipeline engine accelerator to accelerate processing by the primary analysis pipeline engine. For instance, a first portion of the set of digital logic circuits in the master slice may be hardwired as a base calling engine, and a second portion of the set of digital logic circuits in the master slice may be hardwired as one or more embedded processor cores. In such an instance, the base calling engine may be configured to analyze the genetic sequence data from the electronic data source so as to determine a most likely nucleotide at each position sequenced by the sequencer, and/or to estimate a confidence of the most likely nucleotide. In such an instance, one or more of the processing engines of the set of processing engines may be connected to the one or more embedded processor cores via the one or more configurable metal layers formed on the master slice. Additionally, in such an instance, the set of processing engines may further include a base calling engine to analyze the genetic sequence data from the electronic data source to determine a most likely nucleotide at each position sequenced, and to estimate a confidence of the most likely nucleotide; and the set of processing engines may include one or more embedded processor cores.

Additionally, as presented herein a method of making an FPGA or structured application-specific integrated circuit (ASIC) for analyzing genetic sequence data is provided. The method may include one or more of the following: providing a plurality of photolithographic masks that define a set of digital logic circuits of the FPGA or structured ASIC; forming the set of digital logic circuits using the plurality of photolithographic masks to form a first master slice and/or a second master slice that is equivalent to the first master slice; providing a first set of configurable metal layer masks that define at least a first digital logic configuration; and forming a first set of configurable metal layers onto the first master slice using the first set of configurable metal layer masks, such as where the first set of configurable metal layers may have a set of wired connections, e.g., arranged according to the first set of configurable metal layer masks, so as to interconnect a subset of the digital logic circuits of the first master slice according to the first digital logic configuration. The method may further include one or more of providing a second set of configurable metal layer masks such that define a second digital logic configuration; and forming a second set of configurable metal layers onto a second master slice using the second set of configurable metal layer masks, such as where the second set of configurable metal layers may have a set of wired connections arranged according to the second set of configurable metal layer masks so as to interconnect a subset of the digital logic circuits of the second master slice according to the second digital logic configuration.

In various embodiments, the first digital logic configuration may include an input for connecting to an electronic data source such as provides digital signals representing a plurality of reads of genomic data, each of the plurality of reads of genomic data comprising a sequence of nucleotides. In certain instances, the first digital logic configuration may include a memory interface to a memory storing one or more genetic reference sequences associated with genomic data and an index of the one or more genetic reference sequences.

Further, in various embodiments, the first digital logic configuration may include a set of processing engines, the set of processing engines comprising a mapping engine to access the index of the one or more genetic reference sequences from the memory to map the read to one or more segments of the one or more genetic reference sequences based on the index. In certain embodiments, the set of processing engines may include an alignment engine to access the one or more genetic reference sequences from the memory via the memory interface to align the read to one or more positions in the one or more segments of the one or more genetic reference sequences from the mapping engine. And in various embodiments, the set of processing engines may include a sorting engine to sort each aligned read according to the one or more positions in the one or more genetic reference sequences. Additionally, in certain embodiments, the set of processing engines may include any of the modules of the sequencing analysis pipeline as herein detailed. For instance, in some embodiments, the set of processing engines may include a base calling engine to analyze digital measurements of the genetic sequence data to determine the most likely nucleotide at each position sequenced, and/or to estimate a confidence of the most likely nucleotide, such as where the set of processing engines further comprises one or more embedded processor cores.

As can be seen with respect to the above, in various instances, an integrated circuit, e.g., a FPGA, structured ASIC, or even an ASIC, may be provided, wherein the integrated circuit may include a base calling function. For instance, the integrated circuit may include a base calling engine. More particularly, the integrated circuit may have one or more, e.g., a set, of processing engines that include a base calling engine so as to analyze digital measurements, e.g., perform signal processing and/or image processing functionalities, from a sequencer to determine the most likely nucleotide at each position sequenced, and estimate confidence the most likely nucleotide is the correct call.

As described above, in certain instances, the base calling engine may be configured as a set of processing engines that may be formed in and/or by the configurable metal layers, or may be part of or in the master slice. For example, the integrated circuit may include one or more processor cores that may be hardwired in the master slice. Hence, the master slice may include a set of digital logic circuits, which digital logic circuits may form a portion of a set of processing engines, which may be hardwired in the master slice, such as to form a primary analysis pipeline engine accelerator to accelerate processing by the primary analysis pipeline engine. Further, in various instances, the master slice may include two or more sets of metal layers that may be built using two corresponding sets of masks onto two copies of the master slice. However, in such an instance, only one of the two structured ASICs may have the Bio-IT processing engines—the other may be for additional, e.g., different, applications, and the customization of one master slice into two designs allows this to be a structured ASIC process.

As indicated above, the chip, whether implemented as an ASIC, FPGA, or a structured ASIC, may include or otherwise be associated with one or more memory architectures. For instance, a memory architecture can include M memory modules that interface with the chip, such as with an ASIC. The ASIC may be implemented using many different technologies, including FPGAs (Field Programmable Gate Arrays) or structured ASIC, standard cells, or full custom logic. Within the ASIC are a Memory Subsystem (MSS) and Functional Processing Units (FPUs). The MSS contains M memory controllers (MCs) for the memory modules, N system memory interfaces (SMIs) for the FPUs, and an NxM crossbar that allows any SMI to access any MC. Arbitration is provided in the case of contention.

Each memory module is constructed from DRAM chips that are addressed by an $A_{MM}$ bit word and support data transfers $D_{MM}$ bits wide. The memory has $2^{A}{}_{MM}$ address locations. A key characteristic of DRAM is that it performs reads/writes in W word bursts using the supplied address as the base address, B, and fetching or storing locations B+1, B+2, . . . B+W−1 as well. A typical value for W is 8.

In the MSS of the ASIC, each memory controller supplies the required control signals and performs any necessary multiplexing/demultiplexing between the system word width, $D_{SYS}$, and the memory word width, $D_{MM}$, as well as handling the requirements for read/write bursts. It can contain extra buffering so that multiple memory requests can be queued up and processed in a pipelined fashion to maximize throughput. This compensates for multiple clock cycles of latency between presentation of an address and completion of a memory operation (read or write).

The MC may operate at the speed of the attached DRAM in a memory module. Assume its clock rate is $C_{MM}$. This is often several times faster than the core speed at which the majority of the logic in the ASIC operates which is $C_{SYS}$. Hence the multiplexing/demultiplexing logic is placed close to its associated interface pins to minimize signal distances. Demultiplexing is the first operation performed on incoming data and multiplexing is the last operation performed on outgoing data. The remainder of the MSS operates on $D_{SYS}$ width data which is wider than $D_{MM}$, enabling use of the slower $C_{SYS}$ clock speed.

Each system memory interface in the MSS presents an $A_{SYS}$ bit address bus and a $D_{SYS}$ bit data bus to any attached FPU. The SMI is designed to make it appear to an attached FPU that it has random access to a single large fast memory. The FPU has no awareness of the existence of separate memory modules. $A_{SYS}$ is large enough to allow access to any memory location in any attached memory module. The mapping from system address space to memory module address space is explained below.

The N system memory interfaces are cross connected to the M memory modules via an N×M crossbar. The crossbar provides min(M,N) simultaneous connections among the SMIs and MCs, provides arbitration for conflicts, and facilitates translation of system address space into memory module address space.

The organization of FPUs is highly flexible. One or more FPUs can share the same system memory interface. To maximize performance, FPUs that do not operate at the same time should share an SMI. Those that operate concurrently, should be attached to different SMIs. An FPU that operates on a data structure larger than $D_{SYS}$ can use multiple SMIs to access the whole data structure in a single memory operation. Hence this memory architecture supports a wide range of computation architectures. Each FPU may be identical and thus an array of them may be implemented in a two dimensional structure. This is illustrated where FPU (i,j) is the $j^{th}$ unit attached to SMI i, 0≤i<N, 0≤j<$k_i$. In this case, all the $k_i$ are the same size and $k_i$ may be as small as 1. This supports SIMD (single instruction stream, multiple data stream) and MIMD architectures (multiple instruction stream, multiple data stream) depending on whether the FPUs fetch instructions from the same or individual instruction memories.

Where one or more FPUs are provided, each FPU may perform a specific, highly customized function. There may be different numbers of FPUs attached to each SMI, so the $k_i$'s may have different values. For instance, there may be an FPU that operates on data that is $2D_{SYS}$ in size. In that case it would interface to SMI 0 and 1 and could calculate an appropriate offset between each of the addresses presented to the two interfaces, e.g., simultaneously. The system can be structured such that any given FPU can interface with as many SMIs as desired up to N. An FPU can operate on data of size $ND_{SYS}$ in a single memory operation. If a data size required is less than a multiple of $D_{SYS}$, then it may be padded out to the nearest multiple of $D_{SYS}$ when placed in memory. If N is a power of two, it can be represented as $2^n$, where n is an integer and $n=\log_2 N$. In general, $N/2^i=2^{n-i}$ FPUs may operate in parallel if they operate on data of size $kD_{SYS}$, $2^{i-1}+1 \leq k \leq 2^i$, and $0 \leq i \leq N$. For example, if N=8, then n=3. If i=2, then the system would support $2.\text{sup}.3-2=2$ FPUs that operate on data that is between $2^{2-1}+1=3$ and $2^2=4$ times $D_{SYS}$ in size. If N is not a power of two, then [N/k] FPUs can operate in parallel if they operate on data of size $kD_{SYS}$, where [i] is the floor function that returns the largest integer not greater than i. For example, if N=7 and k=3, then [7/3]=2 such FPUs could operate in parallel.

Table 3 summarizes the parameters that may be defined to characterize an exemplary architecture of the present disclosure.

TABLE 3

| Parameter | Description |
|---|---|
| $A_{MM}$ | Memory Module Address size (bits) |
| $D_{MM}$ | Memory Module Data size (bytes) |
| W | Memory Module Words processed per burst |
| $C_{MM}$ | Memory Module Clock speed (Hz) |
| $A_{SYS}$ | System Address size (bits) |
| $A_{SYS'}$ | Portion of System Address presented to a Memory Controller (bits) |
| $D_{SYS}$ | System Data size (bytes) |
| $C_{SYS}$ | System Clock speed (Hz) |

To optimize a given implementation, the rate at which a SMI can process data should be balanced with the rate at which any memory module can process the data; and/or the total amount of data processed per operation should also balance. Double Data Rate (DDR) DRAMs have the characteristic that they can transfer a data word on both edges (rising and falling) of the clock. Thus, a single memory operation may process $WD_{MM}$ Bytes at the rate of $2C_{MM}/W$ Bytes/Sec (BPS) which is $2D_{MM}C_{MM}$. The system memory interface may processes bytes at the rate of $D_{SYS}C_{SYS}$ BPS. The two constraints to be met for a balanced system operation can be expressed as follows:

$$D_{SYS}C_{SYS}=2D_{MM}C_{MM} \quad\quad 1)$$

$$D_{SYS}=D_{MM} \quad\quad 2)$$

In equation 2), p represents the fraction of data delivered by a memory module that the system could use in a single memory operation. Solving for p by using equations 1) and 2) to obtain:

$$p=2C_{MM}/WCC_{SYS} \quad\quad 3)$$

With these equations, all but one of the parameters can be chosen and then the remaining parameter can be calculated and evaluated to determine if it is satisfactory. For example, DRAM components come in families of parts with different speeds. So the system data size and clock speed and the memory module data size may be chosen and what the memory module speed should be can be determined:

$$C_{MM}=D_{SYS}C_{SYS}/2D_{MM} \quad\quad 4)$$

For example, if $D_{SYS}=8$ Bytes, $C_{SYS}=600$ MHz, and $D_{MM}=2$ Bytes, then $C_{MM}=1.2$ GHz. That calculated speed then can be reconciled with available speeds for the nearest match. On the other hand, it may be known that the fastest available DRAMs are to be used, so the appropriate memory module data width given the same system data size and speed should be calculated, e.g., according to the following equations:

$$D_{MM}=D_{SYS}C_{SYS}/2C_{MM} \quad\quad 5)$$

$$D'_{MM}=\lceil D_{SYS}C_{SYS}/2C_{MM}\rceil \quad\quad 6)$$

In many cases, equation 5) may produce a result that is not an integer, so the ceiling function in equation 6) may be used to round up to the nearest integer. For example, if $D_{SYS}=8$ Bytes, $C_{SYS}=600$ MHz, and $C_{MM}=2.5$ GHz then $D_{MM}=0.96$ Bytes so $D'_{MM}=1$ Byte. We can plug $D'_{MM}$ into the following formula for $C_{SYS}$ to see how much faster we could run the system clock for an exact balance:

$$C_{SYS}=2D'_{MM}C_{MM}/D_{SYS} \quad\quad 7)$$

In various instances, $C_{SYS}=625$ MHz is the results.

The following notation for addresses: $[A_{SYS}]=[a_{n-1} \ldots a_1 a_0]$ is the bit representation of an arbitrary system address, so $A_{SYS}=n$ and the total size of the address space (number of addressable words) is denoted $|A_{SYS}|=2^n$. Each crossbar interface on the SMI side has a destination port address that specifies which MC to access. That address maybe designated $[D]=d_{m-1} \ldots d_1 d_0$ where there are $M=2^m$ MCs. Assume the size of a DRAM word burst is a power of two so $W=2^w$. $[A'_{SYS}]$ and $[A_{MM}]$ may be specified in terms of bits in $[A_{SYS}]$ as follows. For instance, to fully interleave the memory modules assign the m least significant bits of $[A_{SYS}]$ to $[D]=[d_{m-1} \ldots d_1 d_0]=[a_{n-1} \ldots a_1 a_0]$. The remaining high order bits may be assigned to $[A'_{SYS}]=[a'_{n-1} \ldots a'_1 a'_0]=[a_{n-1} \ldots a_{m-1}a_m]$. Thus $|A'_{SYS}|=2^{n-m}$. Finally, $[A_{MM}]=[b_{n-m+w-1} \ldots b_w b_{w-1} \ldots b_1 b_0]=[a_{n-1} \ldots a_{m+1}a_m b_{w-1} \ldots b_1 b_0]$ and $|A_{MM}|=2^{n-m+w}$. The low order w bits of $[A_{MM}]$ access a burst of W words and the high order bits are supplied by $[A'_{SYS}]$.

As an example, suppose it is desired to deploy a system with 256 GB of memory and that $D_{MM}$ is one byte wide and $D_{SYS}=8$ bytes. Also, there are M=4 Memory Modules so m=2. The word burst is W=8 so w=3. The system address requires 256 GB/8 Bytes which is 32 Gwords. Thus $n=\log_2 N=\log_2 32G=35$. The size of each Memory Module, $|A_{MM}|=2^{n-m+w}=2^{35-2+3}=2^{36}=64$ GB.

Where the goal is providing very high random TOPS, another variant of the memory system may be useful. Attaching 16 independent 800 MHz DDR3 DIMMs to the ASIC would provide 3.2 billion random reads or writes per second, but in such instances too many pins may be required for this to be practical. A key difficulty is a low ratio of random accesses to wires interfacing to DRAM due to minimum burst lengths, e.g. 200 million accesses/sec over 148 wires. If DDR3 DRAM interfaced like SRAM at its 1600 million transfers per second rate, each transfer representing a random access, then the accesses/wires ratio would be 8 times higher, with the acceptable tradeoff that bursts are 8 times shorter, e.g. 8 bytes per access instead of 64 bytes per access. But DRAM does not typically function this way, because internal DRAM memory clocks are typically limited to 200-266 MHz.

It is possible to attain such a high accesses/wire ratio with short data bursts by introducing intermediate "expansion chips", to which the high DDR3 pin counts can be exported. An expansion chip may be a small FPGA or ASIC or structured ASIC, and serves as a bridge from a low-wire-count word-access interface to the traditional high-wire-count burst-access interface. Whereas the DDR3 interface requires e.g. 148 wires for DIMMs, the word-access interface can use as few as 20 wires. Both interfaces may have the same random access rate, e.g. 200 million accesses per second using 800 MHz DDR3, but the 148-wire interface transfers 64 bytes per access, whereas the 20-wire interface transfers 8 bytes per access.

Each expansion chip may bridge 1 or more such interface pairs; for example one expansion chip may bridge 4 word-access interfaces to 4 DDR3 DRAM interfaces, and 4 expansion chips may then be used to bridge 16 interface pairs. Using multiple expansion chips is useful to accommodate high pin counts for the DDR3 DRAM interfaces, and to limit routing lengths to each DIMM. But all 16 word-access interfaces can connect to a single processing ASIC, because e.g. 16 time 20 pins is only 320 pins. This is a factor of 7.4 times fewer pins than the 2368 pins required for 16 DDR3 DIMM interfaces, as shown in the figure below.

It is understood that the quantity 16 of DIMMs and interface pairs is an arbitrary choice, and this system scales to any quantity of interfaces, such as 1, 2, 8, 24, or 32, up to the pin capacity of an ASIC package. Although it is an advantage of this system that standard DIMMs may be used, it is also understood that SODIMMs or any other DRAM module or configuration of one or more SDRAM chips may be used per interface. It is also understood that other DRAM technologies than DDR3 are equally applicable, such as DDR2 or DDR4. The interface and memory frequencies quoted herein are also merely examples; 800 MHz is an advantageous speed for FPGA expansion chips, but 1066 MHz or other frequencies may be used. Finally, it is also understood that when multiple word-access interfaces connect to one expansion chip, they can equally well be implemented as a smaller number of wider shared interfaces, which indeed can have the strong advantage of higher throughput for unbalanced access patterns. Or, separate interfaces can be used, but nevertheless shared to bridge to multiple DRAM interfaces. Only for clarity of description, they are presented as separate and strictly paired interfaces here.

A 20-wire word-access interface may be configured as two 10-wire 800 MHz DDR busses, one 10-wire bus from the integrated circuit to the expansion chip, ASIC, etc., and one 10-wire bus from the expansion chip to the integrated circuit, ASIC, etc. Similar to a DDR3 interface, 8 transfers are used for one command or data word, yielding an 80-bit word every 8 transfers/4 clock cycles. Thus, the 20-wire word-access interface provides 200 million 80-bit words per second communicated in each direction. 80 bits is easily enough bits to support a read or write request with address, length, and identifying tag; or a 64-bit data word with tag. Other bits can encode command opcodes, back-pressure signals, configuration parameters, or other hand-shaking as required by the application. Each interface may then support 200 million 8-byte random memory reads per second, with each read request sent as one word on the IC to expansion chip bus, and each data return sent as one word on the expansion chip to IC bus. Each interface also supports 100 million 8-byte random memory writes per second, using two 80-bit words on the IC to expansion chip bus for command and data phases of each write.

As a second option, 36-wire word-access interfaces may be used, with an 18-wire bus in each direction. This is feasible in part because 16 times 36 pins is only 576 pins on the IC, e.g., ASIC. Each 8-transfer word is then 144 bits. For reads, this option can increase the return data length to 128 bits, yielding 200 million 16-byte random reads per second. For writes, this option can send address and 64 bits of data in the same word, yielding 200 million 8-byte random writes per second. Many other options are likewise feasible, such as a 28-wire interface comprising a 10-wire IC to expansion chip bus and an 18-wire expansion chip to IC bus, supporting 200 million 16-byte reads per second or 100 million 8-byte writes per second. Such a configuration may be appropriate because many genetic processing algorithms have much greater reading requirements than writing requirements. Even a 34-wire IC to expansion chip bus may be useful to return 32-byte read data; 34+10=44 wires times 16 interfaces is 704 pins, still practical in appropriate IC, e.g., ASIC, packages. It is also straightforward to implement the word-access interfaces as lower frequency or non-DDR busses, with more wires to construct the required word size at the reduced transfer rate. At the other extreme, SERDES word-access interfaces may be used to reduce the IC pin count further or increase the data word sizes.

The task of each expansion chip may be to perform the memory accesses commanded on the IC, e.g., ASIC, to expansion chip bus using the corresponding DDR3 DRAM interface. Write bursts can be aggregated into 64-byte bursts before writing to DRAM, or committed in smaller segments using byte masks. Read bursts may be serialized into multiple return words, with any excess DDR3 burst data dropped. In the case of a read request for a single data word (e.g. 8 bytes or 16 bytes), most of the 64-byte DDR3 burst will be discarded. When the IC is continuously making short or single-word reads and/or writes, the DDR3 interface may be completely busy, but many write bytes may be masked and many read bytes may be dropped. When the IC is continuously making long burst reads and/or writes in aligned multiples of 64 bytes, no bytes may be masked or dropped, but the DDR3 interface may be only fractionally utilized. These apparent "inefficiencies" on the DDR3 interface may be the natural result of bridging a narrow word-access interface to a wide DDR3 interface, and may be the result of a deliberate trade-off to obtain high random access rates with low IC pin counts.

To further optimize achievable random access rates, the expansion chip can buffer and re-order read and write requests to optimize DRAM access efficiency by avoiding row conflicts within a bank, by holding back conflicting accesses until their rows are open, and committing other accesses in the interim. To support out-of-order DRAM operations, command and data words can carry identification tags, e.g. 8-10 bit values selected by the ASIC, which can be used to determine the origin of each return data word. Words within a single burst can be kept ordered, so that no word index is required. Tags for completed writes may be returned to the IC using a "write complete" opcode, or several tags may be batched into one return word.

An expansion chip may also provide a feature of byte-addressability, or even bit-addressability. For instance, although return data for each read may be in 8-byte (64 bit) words, the IC may not need to read on an 8-byte boundary, but rather may supply an extra 3 address bits to read starting from any byte position, or an extra 6 address bits to read starting from any bit position. This capability can be valuable for genetic algorithms, by allowing odd-sized data structures to be packed into the smallest possible space. On the occasions that a byte-or-bit addressed word access crosses a 64-byte boundary, the expansion chip may read or write to two words. Bit addressability may be difficult for writes, because DRAM chips typically have byte masks, not bit masks, so read-modify-write operations may be required. But if a particular genetic algorithm's writing requirements are much lower than its reading requirements, this loss of write performance may be worth the extra data compaction from bit addressability.

While various techniques achieve high random access rates of up to 3.2 billion per second or somewhat higher, genetic algorithms, such as various of those disclosed herein, can benefit from much higher random access rates. To achieve higher access rates, while avoiding practical limitations on the number of memory interfaces utilizing IC pins and the number DRAM chips or modules connected, a solution is to bring a large quantity of memory inside the genetic processing IC.

Inside the IC, there is almost no bandwidth or access rate limitation. A given quantity of memory can be constructed as many distinct memory blocks, whose ports (single, dual, or other) can be accessed in parallel. For example, 256 MB of on-chip memory may be instantiated as 256 single-port blocks of 1 MB each, permitting up to 256 random accesses per clock cycle. At 500 MHz, the aggregate access rate is then up to 128 billion accesses per second. Or 1024 blocks of 256 KB may be used, supporting 512 billion accesses per second.

Specific uses of high-access rate on-chip memory for genetic algorithms include storing and accessing:

1. One or more reference genomes or portions thereof, to be read for comparison and alignment with read sequences, for example 2. One or more Burrows-Wheeler indexes, of full or partial reference genome(s), possibly reversed and/or complemented, to be read iteratively to search for target sequences, which may be read sequences or portions thereof, possibly modified by substitutions, insertions, and/or deletions, according to methods similar to BWA, Bowtie, or other Burrows-Wheeler Transform based genetic algorithms 3. One or more hash tables, accessed with hash keys derived from target genetic sub-sequences (K-mers), from reference genomes and/or read sequences, and storing information not limited to: position in a reference genome, coverage frequency, and adjacent sequence bases; to be read to search for target sequences, which may be read sequences or portions thereof, possibly modified by substitutions, insertions, and/or deletions, according to methods similar to Qamar or other hash-based alignment, error correction, or other genetic algorithms.

One chief difficulty is density. Genetic processing algorithms often need to access data structures which are multiples of the size of a full genome, e.g. 3.1 billion base pairs for human. For example, a whole reference genome may be referenced or searched for read alignment; a compactly encoded human reference genome occupies over 738 MB of memory. Similarly, a Burrows-Wheeler transform index of a genome, which is somewhat larger, is commonly searched. Sometimes hash tables are constructed of K-mers, which can occupy multiple bytes per genome base pair, e.g. 8 GB.

By creative algorithms, it may be possible to swap smaller portions of such a large table into the ASIC, and operate only within the current table portion for some time, before swapping in a different portion. But such approaches may have performance penalties, which can be quite severe especially if the portion loaded on chip is too small a fraction of the whole. Therefore, it may be desired to fit as much memory as possible in the IC, such as 128 MB or 256 MB, or even 768 MB or 1 GB to accommodate a full genome or index. At standard SRAM densities, e.g. about 4 million bits per square centimeter using 28 nm silicon processes, such sizes are difficult and costly, e.g. 256 MB requiring a 23 mm×23 mm die, and 1 GB requiring a 45 mm×45 mm die. In practice, the die must be even larger to accommodate other logic and routing and such.

A useful solution may be the use of ultra-high density memory technologies, such as embedded DRAM (eDRAM) or single-transistor SRAM (1T-SRAM). Each of these can be approximately 3 times denser than SRAM, so that 256 MB requires only 13 mm×13 mm of silicon, and 1 GB requires 26 mm×26 mm. These may be much more practical and economical die sizes. Depending on the ultra-high density memory technology and silicon process, these memories may operate at restricted frequencies, such as 250 MHz rather than the possible 500 MHz of other logic. This issue can be overcome without loss of aggregate access rate by dividing the memory into more and smaller blocks, thus obtaining more ports to access in parallel.

Another difficulty is how to use such high access rates, e.g. 256 per (logic) clock cycle. An advantageous architecture is to have a similar (or somewhat larger or smaller) number of parallel processing cores, which conveniently may be identical. Each processing core may be enabled to make one memory access per clock cycle. Each processing core may have a many-threaded architecture, such as 128 threads, where each thread may be working on a different piece of the problem, e.g. aligning a different read to a reference genome with a full or partial index in on-chip memory.

By use of an execution pipeline that threads arbitrate into, each thread can enter the pipeline, execute algorithm computations, make a memory access from a memory access pipeline stage, and then return to thread storage to wait for return data if applicable. When return data arrives, the thread can again arbitrate into the processing pipeline. If each thread pipeline pass makes a memory access, and the number of threads is substantially larger than the average read latency to target memory blocks, then such a processing core can make a new access almost every cycle. Then if the number of processing cores is at least equal to the number of memory accesses available per cycle, the target high access rate can be achieved. If a processing core's thread pipeline often fails to access memory, then a processing core may have multiple pipelines to increase the access rate, or more processing cores may be used.

It is to be noted that memory block access patterns for threads can be balanced on average to approach the maximum access rate. If disproportionate numbers of accesses target a particular memory block, then access to that block may throttle overall algorithm progress. This is mainly an issue for algorithm design. Each genetic algorithm should be implemented to distribute stored data in such a manner that access patterns are nearly balanced. For example, consecutive entries in a large randomly table may be interleaved or otherwise divided evenly among all memory blocks. Or, if some or all of a thread's accesses will be to an associated memory segment, the segment may be stored in a single nearby memory block, but such segments for all threads should be evenly distributed among all memory blocks.

Another difficulty is topology: how to allow many processing cores to access many memory blocks in random fashion. A crossbar switch may be used, as described in this disclosure, but that may be impractical because crossbar size grows with the square of the number of ports. Alternatively, a multi-stage pipelined switch may be used, with smaller crossbars instantiated in each stage, such that a request or response is routed to one of several nodes in each stage. For example, a 256×256 switch may be implemented in 3 stages, using 32 8×8 crossbars in the first stage, 32 8×8 crossbars in the second stage, and 64 4×4 crossbars in the third stage. The target block index may be an 8-bit value, with 3 bits used to select the first crossbar path, 3 bits for the second crossbar, and 2 bits for the third. Because these crossbars are much smaller than 256×256, the N-squared crossbar growth implies that their aggregate size is also much less. This approach has greatly improved logic area, but can still have routing delay issues when connecting to memory blocks all across a large silicon die.

One advantageous solution is a geometric array of cells, where each cell comprises at least one memory block, at least one processing core, and at least one switch node. The array can be a square or rectangular grid of cells, for example. Each cell's switch node can connect to a limited number of "neighbor" cells, which may or may not be physically adjacent, but should be nearby to limit routing delays. A memory request from a processing core in one cell can route to a memory block in another cell by one or multiple steps through intervening switch nodes, and a memory response can route back to the processing core by the same or different path.

For example, in an IC, e.g., an ASIC, with 256 processing cores and 256 memory blocks of 1 MB size each, 256 cells may be constructed, each cell comprising one 1 MB memory block, one processing core, and/or one switch node. These cells may be arranged in a 16×16 square grid, with switch connections between horizontally adjacent cells and vertically adjacent cells. Each cell, memory block, processing element, and switch node can be indexed with an ordered pair (x,y) where x and y are integers between 0 and 15; and switch node (a,b) connects to switch nodes (a−1,b), (a+1,b), (a,b−1), and (a,b+1), except at edges of the grid. Then, for example, if processing core (3,5) needs to read from memory block (14,2), its request can route by 11 horizontal steps from switch node (3,5) through (4,5), (5,5), . . . , (14,5), then 3 vertical steps through (14,4), (14,3), and (14,2). Other paths are possible, for example vertical steps taken before horizontal steps, and paths may be chosen dynamically to avoid congested switch nodes, for example selecting between a vertical or horizontal step based on lower congestion. Such a construction has the advantage of limited switching logic, since each switch node only makes 4 connections in this example, and the advantage of short routing delays between switch nodes because connected cells are physically near each other in the array.

Another advantageous array may have a torus configuration. In a torus topology, the array does not have edges from a networking standpoint, because switch nodes at an edge connect to switch nodes at the opposite edge. A 16×16 torus comprises a 16×16 square array as described above, but with additional connections between the left and right edge, and between the top and bottom edge. Node (0,5) additionally connects to node (15,5), for example. Considering the same example, if processing core (3,5) needs to read from memory block (14,2), its request can route by 5 horizontal steps from switch node (3,5) through (2,5), (1,5), (0,5), (15,5), and (14,5), then 3 vertical steps through (14,4), (14,3), and (14,2). This is a shorter path, by taking the "short cut" from the left edge to the right edge. A torus configuration can improve congestion substantially compared to a rectangular array, firstly because average communication paths are shorter, and secondly because a perfect symmetry is achieved, and under circumstances of random memory accesses, no switch node will be more heavily utilized than any other switch node.

To avoid physically long routing between left and right edges, and between top and bottom edges, the logical (topological) connections among cells (x,y) may be retained as described, but cells may be positioned differently in the physical grid, in a "folded" layout. In a folded layout, adjacent cells are usually 2 physical grid positions apart instead of 1, and the progression from one logical "edge" to the other is arranged, for example, as a progression from one physical edge to the other in even cells, followed by a progression back to the first physical edge in odd cells. Logical torus columns {0, 1, 2, 3, 4, 5, 6, 7, 8, 9, 10, 11, 12, 13, 14, 15} can therefore be placed in physical grid columns {0, 2, 4, 6, 8, 10, 12, 14, 15, 13, 11, 9, 7, 5, 3, 1}. In such a layout, there is no longer long physical routing between logical columns 0 and 15, because they are in physical grid columns 0 and 1. Likewise, logical torus rows can place in physical grid rows by the same mapping. In this folded configuration, any two connected cells are either 1 or 2 physical grid steps apart, so maximum routing delays are limited.

It is understood that various array dimensions may be selected, such as 16×16, or 8×8, or 12×12, or 8×16, or 12×16. Larger array dimensions may be used without altering the total amount of on-chip memory, by dividing the memory into smaller memory blocks. Larger arrays of smaller cells may be advantageous to reduce the routing delays between neighbor cells. Smaller arrays of larger cells may be advantageous to reduce the average or maximum number of steps to route from one cell to another, and to reduce congestion at switch nodes.

In an N×M torus array, if communications (such as requests from processing cores to memory blocks, or responses from memory blocks to processing cores) are evenly or randomly distributed among possible source/destination coordinates, the average number of horizontal steps per communication is N/4 for even N. (For odd N, the average horizontal steps is $(N^{2-1})/4N$, which is also close to N/4 when N isn't small.) Due to the topological symmetry, if communications from each cell occur at a uniform or average rate of R per clock cycle, then each horizontal link may be utilized an average of RN/16 times per cycle in each direction. Likewise, each vertical link may be utilized an average of RM/16 times per cycle. Links between switch nodes should be implemented with bandwidth meeting or exceeding these values.

For example with a 16×16 torus, with each processing core making one memory request per cycle to a random memory block, and each memory block responding once per cycle to such requests, we have N=16, M=16, and R=2 (for one request and one response from each cell per cycle). Therefore the expected utilization of each link is 2*16/16=2 transactions per cycle, in each direction. Accordingly, each horizontal link may be constructed to accommodate 2 left-to-right transactions and 2 right-to-left transactions per cycle, and vertical links constructed with the same bandwidth. An 8×8 torus with identical behavior would expect 1 transaction per cycle per link per direction, and a 32×32 torus would expect 4 transactions per cycle per link per direction, for example. To accommodate momentary deviations from average utilization, each switch node may be able to buffer a few excess transactions, and to back-pressure neighboring nodes if its buffer fills up. Implementing higher than the expected link utilization can relieve congestion, at the cost of additional logic area.

Since the average total horizontal and vertical steps for each communication in an N.times.M torus array is (N+M)/4 (again this is inexact for odd N and/or M), the expected latency of each communication is (N+M)/4 times the average latency of each step. For example, in a 16.times.16 array, if the average latency of each step is 2 clock cycles, the average communication latency is 2*(16+16)/4=16 cycles. The average round-trip latency of a memory request and response may be twice this time, plus the delay to access a memory block within a cell. For example if a memory block takes 4 cycles to access, the average round trip latency may be 16+4+16=36 cycles, in this example. Processing nodes may be constructed to accommodate this expected latency, but still maintain the target memory access rate, through the use of sufficient threads and/or execution pipelines.

System resources such as off-chip memory interfaces, configuration and control logic, could be connected to the cell array globally, with each cell having system resource connections. Advantageously, system resources may also be accessed through the switch node network fabric. This could be done by connecting a system resource to one cell or a subset of cells, such as cells at an adjacent edge of the die, for example. It can also be done by providing one or more special cells, or an extra row or column of cells, which participate in the network topology (e.g. torus) with comprised switch nodes, but comprise system resources or interfaces thereto rather than processing cores and memory blocks. For example, a $17^{th}$ column of 16 cells could participate in a 16×17 torus, providing access to memory interfaces, configuration and control logic, and processing cores could communicate with the system resource cells in their own rows.

As can be seen with respect to FIG. 9, in one particular aspect, the disclosure is directed to a system, such as to a system for executing a sequence analysis pipeline on genetic sequence data. In various instances, the system may include an electronic data source, such as a data source that provides digital signals, for instance, digital signals representing a plurality of reads of genomic data, where each of the plurality of reads of genomic data include a sequence of nucleotides. The system may include one or more of a memory, such as a memory storing one or more genetic reference sequences and/or an index of the one or more genetic reference sequences; and/or the system may include a chip, such as an ASIC, FPGA, or sASIC.

More particularly, in various particular embodiments, the system may include a structured application specific integrated circuit (ASIC), such as where the chip is formed of a set of mask-programmable, hardwired digital logic circuits that may be interconnected by a plurality of physical electrical interconnects. In various instances, one or more of the plurality of physical electrical interconnects include an input to the structured ASIC that is connected with the electronic data source, such as for receiving the plurality of reads of genomic data. In such an instance, one or more of the plurality of physical electrical interconnects may include a memory interface for the structured ASIC to access the memory. Accordingly, the hardwired digital logic circuits may be arranged as a set of processing engines, such as where each processing engine may be formed of a subset of the hardwired digital logic circuits so as to perform one or more steps in the sequence analysis pipeline on the plurality of reads of genomic data. In various embodiments, one or more, e.g., each, subset of the hardwired digital logic circuits may be in a wired configuration such as to perform the one or more steps in the sequence analysis pipeline. For instance, the set of processing engines may be configured to include one or more of a mapping module, an alignment module, and/or a sorting module.

For example, the set of processing engines may include a mapping module that is in the wired configuration, and is configured to access, according to at least some of the sequence of nucleotides in a read of the plurality of reads, the index of the one or more genetic reference sequences from the memory via the memory interface so as to map the read to one or more segments of the one or more genetic reference sequences based on the index. For instance, in certain embodiments, the index of the one or more genetic reference sequences may include a hash table, and/or the mapping module may apply a hash function to the at least some of the sequence of nucleotides to access the hash table of the index.

The processing engines may also or alternatively include an alignment module that is in the wired configuration, and is configured to access the one or more genetic reference sequences from the memory, e.g., via the memory interface, so as to align the read to one or more positions in the one or more segments of the one or more genetic reference sequences, such as obtained from the mapping module. The processing engines may also or alternatively include a sorting module that is in the wired configuration, and is configured to access the one or more aligned reads from the memory, e.g., via the memory interface, so as to sort the read to one or more positions, e.g., chromosomal positions, in the genetic reference sequences, such as obtained from the alignment module.

In various instances, the structured ASIC may include a master slice that incorporates at least some of the hardwired digital logic circuits, and in some instances, may include one or more configurable metal layers that are formed on the master slice, such as where each of the one or more configurable metal layers may have at least some of the plurality of physical electrical interconnects that interconnect the at least some of the hardwired digital logic circuits to form the set of processing engines. In certain embodiments, one or more of the plurality of physical electrical interconnects may include an output from the structured ASIC, such as for communicating result data from the mapping module and/or the alignment module and/or sorting module.

In various instances, the structured ASIC may include a master controller to establish the wired configuration for each subset of the hardwired digital logic circuits so as to perform the one or more steps in the sequence analysis pipeline. In various embodiments, the wired configuration is established upon manufacture of the integrated circuit and is non-volatile. In some embodiments, the structured ASIC and/or the memory are housed on an expansion card, such as a peripheral component interconnect (PCI) card. As indicated above, in various embodiments, the system may include a sequencer, such as where the sequencer includes the electronic data source that provides the digital signals representing the plurality of reads of genomic data. And in such an instance, the expansion card may be physically integrated with the sequencer.

Additionally, in various embodiments, a structured application-specific integrated circuit (ASIC) may be provided, such as for analyzing genetic sequence data, such as where the genetic sequence data is stored in a memory, such as a memory storing one or more genetic reference sequences associated with genomic data, and/or an index of the one or more genetic reference sequences. In such an instance, the structured ASIC may include a master slice that further includes a set of digital logic circuits, and may additionally include one or more configurable metal layers that are formed on the master slice, such as where each of the one or more configurable metal layers may have a set of wired connections arranged to interconnect a subset of the digital logic circuits to form a set of processing engines. In such an instance, the set of processing engines may include a mapping engine, an alignment engine, and/or a sorting engine.

In various instances, a portion of the set of digital logic circuits in the master slice is hardwired as a base calling engine. Further, it is to be noted that one or more of the processing engines described herein may be configured for performing any and/or all of the modules of the BioIT pipeline disclosed herein, and/or may be configured so as to perform other additional, e.g., complementary functions, such as performing one or more of the functions of the various algorithms described herein. For instance, the processing engines may be configured for performing de novo assembly; contig formation (e.g., merging read sequences into long contiguous haploid or diploid sequences, such as with error tolerance); scaffolding (e.g., using paired-end, mate-pair, and/or other information to arrange contigs into longer partial sequences); de Bruijn graph processing (which may be employed as a fundamental technique in many assembly algorithms, e.g., a generic de Bruijn graph or other algorithm function processing engine could be an accelerator for assembly software run in embedded or external processors); local assembly, such as part of variant calling (e.g., when reads in a pileup overlapping a reference position seem inconsistent with each other, local assembly [and/or de novo, or reference guided, possibly using de Bruijn graphs] of these reads can reveal likely true sequences; and/or Smith-Waterman functions can be configured as a processing engine, as herein described, or other dynamic programming engines to accelerate gapped and/or gapless comparison of reads with candidate haplotypes during variant calling, such as part of calculating probabilities of candidate haplotypes and diploid genotypes.

For instance, the set of processing engines may include a mapping engine to access, e.g., according to at least some of the sequence of nucleotides in a read of the plurality of reads, the index of the one or more genetic reference sequences stored in the memory, so as to map the read to one or more segments of the one or more genetic reference sequences, e.g., based on the index. Additionally or alternatively, the set of processing engines may include an alignment engine such as to access the one or more genetic reference sequences from the memory, e.g., via the memory interface, so as to align the read to one or more positions in the one or more segments of the one or more genetic reference sequences from the mapping module. Additionally, or alternatively the set of processing engines may include a sorting engine to sort each aligned read according to the one or more positions in the one or more genetic reference sequences.

In one embodiment, a system for executing a sequence analysis pipeline on genetic sequence data is provided where the system includes an electronic data source that provides digital signals representing a plurality of reads of genomic data, such as where each of the plurality of reads of genomic data include a sequence of nucleotides. The system may include one or more of a memory, e.g., for storing one or more genetic reference sequences and/or an index of the one or more genetic reference sequences; and/or the system may include an integrated circuit having a master slice, such as a master slice formed by a photolithographic mask that defines a set of digital logic circuits. In such an instance, the master slice may be configured for having one or more functions, as those described herein above, integrated therein. For instance, the master slice may have one or more configurable metal layers, such as where each of the one or more configurable metal layers has one or more conductive interconnects that connect a subset of the set of digital logic circuits in a wired configuration to perform the aforesaid functions.

Figure 10:
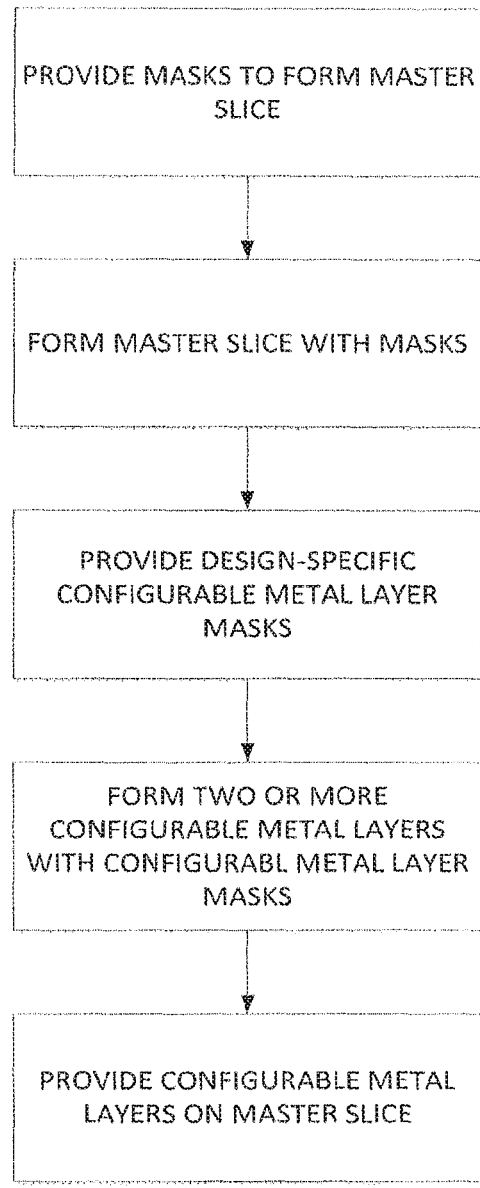
FIG. 10 illustrates a method of making a structured application-specific integrated circuit (ASIC) for analyzing genetic sequence data.

In various aspects, and as shown in FIG. 10, a method of making a structured application-specific integrated circuit (ASIC) for analyzing genetic sequence data is provided. In certain embodiments, the method includes one or more of providing a plurality of photolithographic masks, such as masks that define a set of digital logic circuits of a master slice; forming the set of digital logic, such as by using the plurality of photolithographic masks to form the master slice; providing two or more different sets of design-specific configurable metal layer masks, such as masks that define corresponding two or more digital logic to implement a set of processing engines; forming two or more configurable metal layers, such as using two or more different sets of design-specific configurable metal layer masks, for instance, where each of the two more configurable metal layers have a set of wired connections that may be arranged according to a design of the configurable metal layer masks, for example, to interconnect a subset of the digital logic circuits to form a set of processing engines; and/or providing the two or more configurable metal layers onto the master slice to form the set of processing engines.

One or more aspects or features of the subject matter described herein can be realized in digital electronic circuitry, integrated circuitry, specially designed application specific integrated circuits (ASICs), field programmable gate arrays (FPGAs), or structured ASIC computer hardware, firmware, software, and/or combinations thereof.

These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Accordingly, as set forth above, a goal for health care researchers and practitioners is to improve the safety, quality, and effectiveness of health care for every patient. Personalized health care is directed to achieving these goals on an individual level. By employing the genomics and/or bioinformatics techniques, described herein and above, the identity of an individual's genetic makeup, e.g., his or hers genes, may be determined and that knowledge may be used in the development of therapeutic and/or prophylactic regimens, including drug treatments, that are personalized to the individual, thus, enabling medicine to be tailored to meet each person's individual needs.

Hence, knowledge of a particular individual's DNA sequence is becoming indispensable for basic biological research as well as for personalized health and caretaking. In a particular aspect the need for ever increasing degrees of this knowledge has spurned the introduction and growth of "next-generation" sequencing technologies, such as those described above. For instance, a new generation of sequencing instruments ("next-gen" sequencers) have enabled a remarkably higher throughput at a much lower cost allowing a more efficient, cheaper accessing of genetic, e.g., DNA, sequence data, such as in a primary processing protocol. Along with this advancement and in response thereto there have been several rapid changes and improvements in the associated research technologies. These developments have been coupled with a continuing expansion of applications for which the generated sequence data can be used. At the forefront of these advancements are the "next-gen" instruments that perform the genetic analysis and generate the genetic sequence results.

Three manufacturers of next-gen sequencers each with one primary platform dominate the market, they are: ILLUMINA (Genome Analyzer II or "GAIIx"), Life Technologies (SOLiD), and Roche Applied Sciences (454/FLX). The platform technologies from each of these companies are differentiated by both how the genetic material is synthesized and sequenced, as well as the results generated, which differ with respect to the read length, number of reads per run, cost per run, and number of runs per year performed. The difference between this performance data can be summarized in Table 4 below, in relation to: read length, quantity, and cost data:

TABLE 4

| Platform | Max Read length (per template) | Max Reads/run | Max Total Output/run | Reagent cost/run (@max read length/run) |
|---|---|---|---|---|
| GAIIx | 2 × 100 bp | ~150e6 | 50 GB | ~$10,000 |
| SOLiD | 2 × 50 bp | ~500e6 | 60 GB | ~$7,000 |
| 454/FLX | ~400 bp | ~1e6 | 400 MB | $6,000 |

Figure 11:
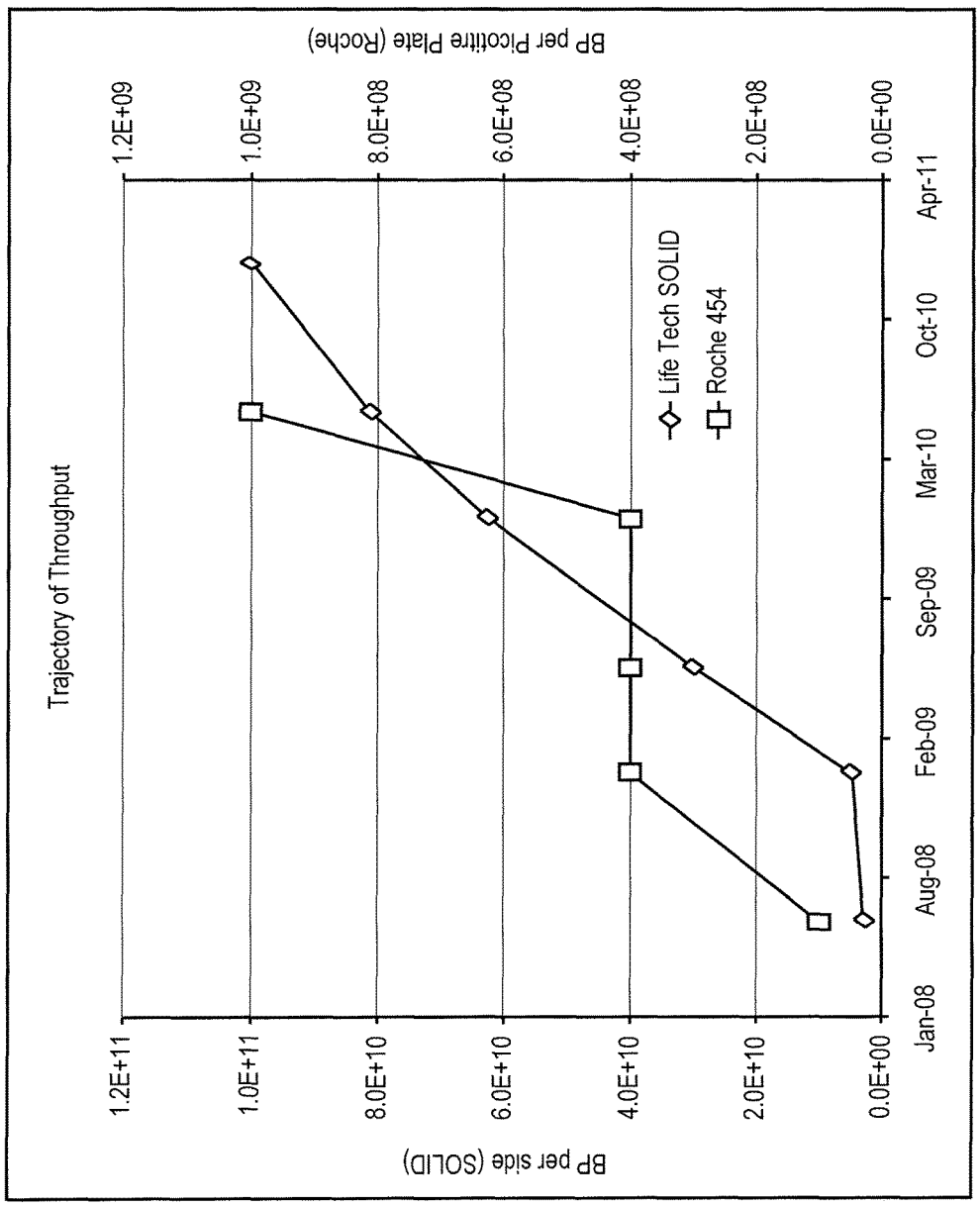
FIG. 11 shows historical and projected output data for implementations of exemplary structured application specific integrated circuits (ASIC).

Historically, throughput, or how many reads can be run at any given time, has been an important measure of performance, where the greater reads run in the shortest amount of time demarcates the performance objectives being sought. Hence, the historical trajectory of increase in throughput over time is a more important consideration than a static view of capacity as it suggests the likely future increases in output. For instance, FIG. 11 shows the historical and vendor-projected output of the Roche/454 (right axis) and Life Technologies/SOLiD (left axis) (where the Illumina/GAIIx trajectory is similar to that of the Life Technologies/SOLiD).

However, it has been suggested that the actual user experience of total output per run varies widely (almost an order of magnitude), nevertheless, because the need for the generated data is so high, in view of its increasing usefulness in biological analysis, it is expected that existing owners of such machines are highly likely to purchase additional instruments simply with funding being a limiting factor. There is, therefore, a need for the development of better instruments and more efficient processes that are capable of generating higher outputs at cheaper costs with enhanced efficiency. Consequently, in view of the above, there is a great need for next-gen sequencers and sequencing protocols deploying the apparatuses, methods, and systems herein described.

In terms of processes, these next-gen sequencing platforms typically rely on "sequencing by synthesis," which requires an ensemble averaging of a reasonably large number of detection molecules per sequencing event. More particularly, all three platforms are enabled by at least three key technologies, which can be employed in accordance with the methods and systems herein described: Clonal amplification, spatial isolation, and synchronized sequencing-by-synthesis. For example, clonal amplification may be performed by PCR, e.g., emulsion PCR, and/or bridge amplification, and can be used to create tens of thousands (or more) copies of each template of genetic material, e.g., DNA. These amplified templates can then be provided in a sequencing library such that upon analysis of the genetic material to be sequenced from a particular individual the detectable signal demarcating that individual's unique genetic sequence can be more easily and clearly detected such as by using this amplified ensemble of copies.

It is to be noted from the outset, for instance, as an orientation to these platforms and their respective applications, it is helpful to differentiate the two fundamentally different types of "libraries" that are commonly used in these platforms. First, a fragment library may be employed wherein each amplified template molecule of the library represents one small (20-500 bp) contiguous sequence derived from the sample. These are usually created by random fragmentation of the genetic material, e.g., DNA or RNA, etc. from the sample, but the fragmentation may occur naturally as with small RNA or ChIP DNA. Such a fragment library can typically be prepared in a few days.

Alternatively, or in addition too a fragment library, a "mate-pair" library may be employed, such as wherein each template molecule of the library has two sequences from the sample that are to be separated by an exogenous sequence, or adaptor. The spatial relationship between the two sequences may generally be defined, e.g., during sample preparation. For example, genetic material, such as genomic DNA, may be sheared to produce a sequence of uniform size, e.g., a sequence of about 2,000 bp. Each sheared molecule may then be circularized with an adaptor that is positioned in such a manner as to join the two ends of the molecule, which new molecule may then be sheared again and purified so as to recover only the sample DNA proximal to the adaptor, e.g., the sequence immediately upstream and downstream of the adaptor, such as the two ends of the original 2,000 bp fragments. Further, it has been determined that long-range DNA/DNA interactions in situ has been facilitated by ligating the adaptor between any two DNA that happen to lie near each other in, for example, a formalin-fixed sample. Mate-pair libraries can typically be prepared in a few days to one to two weeks. In this regard, it is further noted, that the term "paired-end" may be confused with "mate-pair." "Paired-end" sequencing is the reading of sequence from each end of a template molecule. The template may be a fragment library or a mate-pair library, however, bioinformatically, there is no difference in paired-end sequences from a mate-pair or fragment library sequences but for their orientation and distance apart.

Additionally, the other two key technologies that help enable the performance of these three platforms are spatial isolation, such as spatial isolation of each ensemble representing the amplified clones, which may be done concurrently with amplification; and synchronized sequencing-by-synthesis of large numbers ($10^6$ to $10^9$) of these ensembles, such as in a highly parallel fashion. In this case "synchronized" includes the synthesis of the complimentary strand of all the ensembles, such as where that synthesis may be controlled so as to proceed only one "step" per application of the sequencing chemistry, which may then be concurrent with or followed closely by detection of the synthesis event. In some instances, however, sequence quality may be compromised, e.g., significantly, in all platforms relative to conventional Sanger-style sequencing, which may also be used herein. For instance, in some instances, the particular chemistries and detection modalities used in the platforms may lead to platform-specific error types and frequencies. Accordingly, there remains a need for better sequencing chemistries and detection modalities so as to overcome these deficiencies and obtain read outs of better sequence quality, which in turn leads to better secondary and tertiary processing. The apparatuses, methods, and systems disclosed herein meet these and other such needs.

Nevertheless, as noted above, although these three sequencer platforms differ in many details, their objective of sequencing an entire genome, e.g., of one or many individuals, is the same, and to do so they all typically require that the molecules to be analyzed, e.g., sequenced, be provided to the sequencer with specified sequences on each end of the "template", e.g., DNA to be sequenced. The process to generate this population of template molecules from a starting sample (such as genomic DNA, sDNA, mRNA, rRNA, tRNA or small RNA, and the like) is referred to as "library construction," as referenced above. Although the individual sequencing preparation steps are routine molecular biology procedures (e.g., reverse-transcription, shearing, ligation, gel sizing, etc.), this process remains a key bottleneck in next-generation sequencing.

Further complicating matters, such as in terms of secondary processing, is the fact that genomes vary widely in size. The smallest known genome, e.g., for a free-living organism (a bacterium), contains about 600,000 DNA base pairs. In such an instance, the sequencing of such a genome is complicated, but not too unwieldy. But, for such genomes as the human and mouse genomes, which have some 3 billion base pairs, this extreme number of base pairs makes the sequencing and further processing of such genomes magnitudes more difficult than sequencing the genome of a bacterium. So compounding the bottleneck is the fact that these next generation sequencing technologies do not typically read whole genomes in one go, but rather generate small pieces of genetic fragments, such as between about 20 and about 1000 bases long (dependent on the technology used), that need to be sequenced.

Nevertheless, though the absolute capacity of a next-gen sequencer is significant, many experiments need only a small fraction of this capacity to provide meaningful data. Further techniques, such as those described herein, have been developed that may be employed, as herein described, for improving the net "efficiency" of such "next-gen" sequencing. Such advancements may be made with respect to the processing procedures performed in accordance with a sequencing protocol, the algorithms for processing the generated sequence data, and/or one or more hardware accelerators that may assist in the performance of the same. For instance, two such techniques for advancing the processing procedures performed in accordance with a sequencing protocol include partitioning and multiplexing.

Partitioning or targeting, for instance, may be employed so as to reduce the complexity of the starting material. For example, in certain instances, it is only a small portion of a sample (genome, transcriptome, etc) that needs to be sequenced. Accordingly, methods are provided herein for selecting and/or enriching for these regions prior to downstream library construction and sequencing. These methods include PCR-based selections, such as in multiplex PCRs, individual PCR reactions targeting different regions that are subsequently pooled together, and/or targeting single regions that are amplified from dozens to hundreds of individual samples that are then subsequently pooled together. In certain instances, long-range PCR may be employed to maximize coverage.

Another method, herein provided, that has been developed to select or enrich for these small regions to be sequenced, prior to downstream processing, is with respect to the production of one or more reduced representation libraries (RRL). Typically methods may be employed to repeatably disperse nucleic acids in such a manner that only a small, determined fraction need be isolated. A common method for doing this involves enzymatic digestion, such as with a relatively rare-cutting restriction endonuclease, which may then be followed by separation by gel electrophoresis. By quantifying the distribution of DNA mass in the gel, a fixed percentage (e.g. about 1% to about 10% or more) of the DNA can be isolated in a defined size region. In some instances, RRL may be employed in any method to reduce complexity in an analyte, but in many cases RRL employs the use of restriction digest.

A further method that may be employed to select or enrich small regions of genetic material, such as DNA, involves hybridization-based capture (e.g., "target capture" or "target enrichment"). Synthetic genetic material, e.g., DNA or RNA, is designed so as to be complimentary to one or more target regions within the genome to be sequenced so as to act as an affinity reagent, e.g., a "capture probe," for the capturing of one or more sequences having the targeted region. For instance, the probes may be any suitable probe, such as a microarray probe on a microarray, or may be converted to a marked, e.g., biotinylated, RNA for capture in solution. The sample is then allowed to hybridize to many capture probes, and sample genetic material, e.g., DNA, that is not specifically bound to a capture probe will be washed away. In this manner the "enriched" sample DNA may be recovered and used for sequencing. Additionally, prior to building a template library, isolation, for instance, of a specific nucleic acid subpopulation—for example, in human, animal, or plant, such as a chloroplast or mitochondrial DNA, poly-A mRNA, or small RNA, etc. may be performed prior to sequencing.

An additional technique that may be employed, as herein described, for improving the net "efficiency" of such "next-gen" sequencing is multiplexing. "Multiplexing" may involve the "barcoding" and/or "indexing" of a plurality of samples, such as many samples that may be run in a single sequencing procedure. For instance, a sequencer, such as those described above, e.g., the Illumina/GAIIx, Life Technologies/SOLiD, and/or Roche/454 platforms, may be employed in a manner so as to load the sequencing substrate with a sample set such as a sample set having samples from more than one subject, which samples may be separated, such as by physical dividers on the sequencing substrate. For example, the Illumina/GAIIx may run in sets of 8 lanes per flow cell. In such an instance, a short barcode or index sequence may be added to each of the library templates demarcating each separate sample therein with a unique code designating the different libraries. In such a manner as this many such tagged libraries may be combined together independently of the number of regions of the sequencing substrate.

Accordingly, in view of the targeting and multiplexing methods described herein, more samples can be analyzed per run than would be the case by simple physical partitioning of the run space would allow, and because the sequencing space is not being consumed with physical dividers to separate samples, sequence space may be used much more efficiently. Hence, such procedures as multiplexing also saves significant labor and reagent costs by spreading these costs over many samples run in parallel. In some instances, the index sequences may be pre-pended to the template in a manner such that it consumes sequence space but allows for efficient sequencing processes. In other instances, the index sequences may be separately sequenced, such as, by placing the index sequence in one of the two library template regions such as is usually used for a mate-pair library. Note about 12 index sequences have been developed for the Illumina/GAIIx platform, and over 120 index sequences have been defined for the Roche/454 platform and 96 for the Life Technologies/SOLiD platform. Further, since the Illumina/GAIIx typically employs 8 lanes per run, the use of 12 indexes will allow for the simultaneous analysis of up to 96 samples.

In view of the above, the various approaches disclosed herein can be employed in such a manner so as to bring the cost of single-sample sequencing way down, such as below about $1,000, or even to below about $500, or in some instances, below about $100. For instance, by using barcoding, a full transcriptome sequencing run can be run in a manner that the cost may be less than $100 per sample in, however library construction costs presently still remain high $200 to more than $2,000 per sample. More specifically, conventional sequencing instrumentations can produce approximately $10^5$ bases of DNA sequence per day per instrument at a cost of about 0.5 per nucleotide, these "next-gen" sequencing instruments on the other hand can produce about $10^{10}$ bases of DNA sequence per day per instrument at a cost of about $2 \times 10^{-5}$ per nucleotide.

These advancements have allowed for an increased throughput of the next-gen sequencers while at the same time as resulting in a decrease in pricing, which in turn admits for the lower-cost sequencing of whole genomes, such as genomes that have previously been un-sequenced. Further, the methods disclosed herein allow for broadening the application of DNA sequencing far beyond traditional uses, such as for the sequencing of even more advanced platforms such as by utilizing fundamentally different chemistries and/or detection methods than is currently employed by the current platforms.

One such method includes nanopore sequencing, such as where miniscule changes in an electric field and/or conductivity in the vicinity of a nanopore can be detected by the induction caused by the genetic material being analyzed, e.g., DNA or RNA, etc., passing through the pore, which can be imputed to the sequence base composition. This method is useful because such sequencing, e.g., by nanopore, theoretically requires little or no sample preparation, such as for either DNA or RNA analysis, and further requires little to no use of reagents, for instance, requiring little to no external enzymes or labeled nucleotides to be used as well as requiring minutely small amounts of nucleic acid for sequencing (e.g., one molecule, in theory). Another such method includes single molecule sequencing platforms. Single molecule sequencing involves individual molecular events that are observable, such as by the incorporation of a labeled nucleotide, or the motion of a polymerase. Using such a method an entire genome, e.g., a human genome, can be sequenced in one run, and further RNA can be sequenced directly without prior conversion to DNA. In such instances, such as herein described, primary and/or secondary processing may be performed sequentially in one or two runs.

Consequently, in view of these advancements, the estimated installed base of thousands of next-gen sequencers world-wide, combined with an annual doubling of capacity at fixed cost, has rapidly driven adoption of technologies such as these, with the goal being providing access to abundant, low-cost sequence information such as for use in diagnostics, therapeutics, and prophylactic intervention. Many of the developments in these fields have been funded by organizations seeking to bring down the cost for the sequencing of human genomes to less than $1,000 or less than $500 or less than $100, etc. Such funding is important in the development of even more advanced platforms, such as those utilizing fundamentally different chemistries or detection methods, than the current platforms.

However, although there have been several advancements in the field, data standards and analysis tools have historically been developed on an ad hoc basis by individuals or small teams that have been focused on a particular platform and for particular applications. Nevertheless, some de facto standards have emerged and developers are being driven to be more inclusive of a wider range of sequencing platforms and with an emphasis on producing more rigorous uniform software development, but both standards and software remain relatively immature. Consequently, the large quantity of data generated by the various sequencing methods herein presented, combined with the development of complex workflows and changing analysis algorithms, suggests that a large regional or national shared computing resource would be an enabling contribution in the field of next-generation sequencing. Accordingly, in one aspect, the present disclosure is directed to providing a standardized and uniform procedure and platforms for sequencing and processing, e.g., performing secondary and/or tertiary processing, that can make use of the aforementioned advantages and be implemented regardless of the sequencing platform and/or the protocols employed therein, and which can reduce the cost per base and/or genome sequenced, while at the same to increasing the output and enhancing the accuracy and/or efficiency of the system as a whole.

As indicated above, bioinformatics, as disclosed herein, is in part concerned with such advancements. More particular, the bioinformatics processes herein described are concerned with the developments and advancements, such as those described above, that can benefit from the application of information technology and computer science to these fields of molecular biology. Accordingly, in certain instances, the bioinformatics techniques described here may be applied to the DNA sequencing protocols described herein and above so as to determine the order of nucleotide bases in the sequenced DNA, which techniques can be employed, in various embodiments, in such a manner so as to enable an unbiased view not only of genomic DNA/RNA/etc. sequencing, but also of transcript populations, and an increasing number of epigenetic features. The techniques herein disclosed may also be used in other research branches that utilize genetic sequencing, such as numerous applied fields including diagnostic, biotechnology, forensic biology, and biological systematics that makes use of such DNA sequencing. The advent of the technologies herein described significantly accelerates biological research and discovery.

For instance, as detailed above, a central challenge in the use of such DNA sequencing is to determine the variants in the sampled sequence, e.g., the sample of sequenced genetic material generated by one or more of the sequencing platforms described herein above. More particularly, it is a goal of bioinformatics to not only determine a genetic sequence of an individual, but to also determine how that genetic sequence differs, such as from a genomic reference sequence. To do this, various software applications have been developed the concurrent or sequential application of which can be used, such as in a bioinformatics pipeline, to determine how any particular genetic material differs from a referent, e.g., a reference genetic sequence. As a number of steps are typically involved in determining variants of the sampled sequence, a number of algorithms may typically be employed in the process, and thus a wide variety of pipelines employing a wide array of algorithms and/or heuristics have been developed and may be employed herein for such purposes.

For example, a commonly used software implementation for a bioinformatic pipeline is a Genome Analysis Toolkit "GATK." Such pipelines employ the fragments of DNA sequences that are generated from the various sequencers described above for the purpose of one or more of mapping, aligning, sorting, and/or merging those read sequences in order to assemble and construct the whole sequential DNA, such as of an individual. For instance, a BioIT pipeline, such as one that employs a GATK algorithm, can receive various FASTQ files, such as pertaining to the genetic sequences derived from the sequencing of an individual's genetic sample, and may employ various algorithms concurrently or sequentially in a pipeline for the purposes of constructing the original genomic sequence in nucleotide order, such as by comparing the generated DNA fragments to a reference sequence and thereby determining the genomic genetic code. This genetic code may then be used, such as in a tertiary analysis protocol for diagnostic, therapeutic, and/or prophylactic purposes, which may be tailored to the individual, e.g., based on his or her personal genetic code. However, a common characteristic of software based bioinformatics pipelines, such as GATK, is that the pipeline takes a long time to execute on general purpose processors.

As such, given the high capacity of current sequencing technologies to produce genomic data, there is a need for enhanced methods and/or apparatuses that can be employed in a secondary analysis protocol, such as in a BioIT platform, for the purposes of mapping, aligning, and/or sorting those read sequences in order to assemble and construct a subject's whole DNA/RNA, etc., which may then be used for analysis, such as in a tertiary analysis protocol. For instance, as described herein, in various processes of high throughput screening, genetic material, e.g., DNA, is fragmented into small strings of sequences of "reads", wherein for a given genome several millions of "reads", each 30 to 500 to 1,000 base pairs ("DNA characters") long, are produced. The subsequent task, for secondary processing purposes, is to map, align, sort, and/or perform on these reads any of the other functions herein described, such as in accordance to a reference genome, e.g., to a known, nearly complete sequence of the organism in question (which may be up to several billion base pairs long), so as to generate an understanding of how the sequenced genome differs from the reference genome, e.g., to produce a variant call file, which may then be used in a tertiary processing analysis protocol, as described herein.

Accordingly, an important step in such a secondary sequence analysis protocol is the performance of a mapping and/or sequence alignment and/or sorting procedure. In this regard, there have been several software applications that have been developed and may be deployed herein for performing various alignment procedures. For instance, the first successful gapped sequence alignment algorithm was developed by Smith and Waterman. They formulated the alignment problem as a finite optimization problem that they solved by dynamic programming. However, database sizes have increased such that the Smith-Waterman (SW) algorithm is no longer typically employed in alignment software implementations. Nevertheless, it may still be helpful as a base line by which to measure both the performance and quality of other heuristic algorithms.

Additionally and/or alternatively, other efficient algorithms that may be employed for the purposes of performing alignments, as disclosed herein, include one or more of a Burrows-Wheeler Transform, BWA-SW, Bowtie, Mosaik, Velvet, SOAP2, and/or MAQ. More particularly, one such algorithm is a Burrows-Wheeler Transform ("BWT"). As described herein in great detail, a BWT is an algorithm that may be employed to reduce the memory requirements for performing sequence alignments. In various iterations, the aforementioned algorithms employ a version of BWT in their alignment protocols. In its simplest form, BWT builds a searchable trie like data structure that focuses on a prefix and/or a suffix trie that may be formed from storing all the prefixes and/or suffixes of a string of data, such as nucleic acid sequence data, whereby a query sequence may be quickly matched against a branch or root of a data tree, such as a data tree built from a reference genome sequence, such as in a forward or reverse direction. In a manner such as this, all the algorithms on a trie can be seamlessly applied to the corresponding prefix or suffix trie.

A BWT-SW algorithm essentially employs sample substrings of the reference by a top-down traversal on the trie and aligns these substrings against the query, such as by dynamic programming. In various instances, a Burrows-Wheeler Aligner's Smith-Waterman Alignment (BWA-SW) may be used to align long sequences, such as up to 1 Mb against a large sequence database (e.g., the human genome), such as with a few gigabytes of memory. In such an instance, a BWA-SW furthers a BWT-SW by representing the query as a directed cyclic word graph (DAWG), which also may be used to enable it to deploy heuristics to accelerate such alignments. In such instances, such algorithms may be configured such that they may be as accurate as a Sequence Search and Alignment by Hashing Algorithm (e.g., SSAHA2), which may be employed herein, and may be more accurate than BLAT, e.g., a pairwise sequence alignment tool, which also may be employed herein, and may be several to tens of times faster than both.

With respect to Bowtie, Bowtie is an ultrafast, memory-efficient alignment program that may be used for aligning reads, such as short DNA sequence reads to reads of large genomes. For instance, for the human genome, Burrows-Wheeler indexing may be employed in such a manner so as to allow the Bowtie algorithm to align more than 25 million reads per CPU hour such as with a memory footprint of approximately 1.3 gigabytes. Therefore, the implementation of a Bowtie algorithm may used to extend previous Burrows-Wheeler techniques with a novel quality-aware backtracking algorithm that permits mismatches. In such a manner as this, multiple processor cores can be used simultaneously to achieve even greater alignment speeds.

With respect to Velvet, Velvet may be used to manipulate a de Bruijn graph, such as for the purpose of producing genomic sequence assemblies. More particularly, a de Bruijn graph is a compact representation based on short words (e.g., k-mers) that may be employed for high coverage, very short read (25-50 bp) data sets. It may use a Burrows Wheeler Transformation (BWT) compression index to substitute the seed strategy for indexing the reference sequence in the main memory. When tested on the whole human genome, it was found that there is reduced memory usage from 14.7 to 5.4 GB and improved alignment speed by 20-30 times. In an exemplary embodiment, applying Velvet to very short reads and paired-ends information only, one can produce contigs of significant length, such as up to 50-kb N50 length in simulations of prokaryotic data and 3-kb N50 on simulated mammalian BACs. Additionally, in another exemplary embodiment, when applied to real Solexa data sets without read pairs, Velvet was able to generate contigs of about 8 kb in a prokaryote and 2 kb in a mammalian BAC, and further results without read-pair significantly improved versions of the short oligonucleotide alignment program that both reduces computer memory usage and increases alignment speed at an unprecedented rate.

With respect to SOAP2, SOAP2 is compatible with both single and paired-end reads. Additionally, this tool supports multiple text and compressed formats. A consensus builder may also be employed for consensus assembly and SNP detection from alignment of short reads on a reference genome.

Accordingly, as indicated above, although there have been several advancements in the bioinformatics field, such as with respect to the sequencers and algorithms described above, there yet remains several bottlenecks in the analysis process, such as with respect to secondary processing. The above described sequencing platforms can generate an enormous amount of data in a relatively short period of time. The various algorithmic based secondary analysis, e.g., alignment, pipelines, described above, can help speed up various secondary analysis protocols. However, to do so still requires an awful lot of computing resources functioning concurrently over prolonged periods of time. What is further needed, therefore, is a solution that can make use of these advances in sequencing and programming in a manner that reduces the need for a multiplicity of computing resources and is further capable of performing one or more, all, of the stages in a BioIT pipeline for purpose of performing one or more of secondary and/or tertiary processing, in a manner that is fast, accurate, and efficient. The apparatuses, methods, and systems described herein meet these and other such needs.

Therefore, as indicated above, the present disclosure, in one aspect is directed to providing a standardized and uniform procedure and platform for sequencing and/or processing, e.g., performing secondary and/or tertiary processing, that can be implemented regardless of the sequencing platform and/or the algorithmic protocols employed therein, and which can reduce the cost per base and/or genome sequenced, while at the same to increasing the output and enhancing the accuracy and/or efficiency of the system as a whole.

Accordingly, in various instances, this disclosure is directed to a self-contained, automated high-throughput genome sequencing and computational genomics pipeline suitable for primary, secondary, and/or tertiary processing, which may include performing a sequencing protocol, such as on one or more genetic sequences of interest, for instance, in a BioIT pipeline. In various instances, the pipeline is capable of enhanced and/or manually assisted reference-based assembly, using in some instances, one or more of the algorithms set forth herein, e.g., GATK, BLAST, Burrows-Wheeler Transform, BWA-SW, Bowtie, Mosaik, Velvet, SOAP2, and/or MAQ, etc., and in other instances, performing one or more of these same functions using hardware acceleration. For instance, in various instances, one or more, e.g., every, component of the pipeline may be executed on a local machine, or automated sequencer, such as with out the need to access other resources, such as over the Internet. In such an instance, the pipeline may be suitable for projects of a sensitive nature.

For example, in various embodiments, hardware accelerators, such as those described herein, may employ the use of hardware which can be coupled with one or more general purpose processors and/or super computers to perform specific task, such as the tasks performed by the various algorithms described above, e.g., GATK, BLAST, Burrows-Wheeler Transform, BWA-SW, Bowtie, Mosaik, Velvet, SOAP2, and/or MAQ, etc., faster than as implemented in their software form. Such hardware accelerators can be used alone or with general purpose processors or super computers to fasten such bio-IT pipelines. Many types of hardware devices are available such as FPGAs, ASICS, structured ASICs, and GPUs for many applications. More particularly, an FPGA, is a class of hardware accelerators that can be programmed after manufacturing. Hence, instead of being restricted to any predetermined hardware function, an FPGA allows product features and functions to be programmed, to adapt to new standards, and thus the hardware can be reconfigured for specific applications even after the product has been installed in the field—hence the name "field-programmable."

Such hardware accelerator technology has not heretofore been employed for wide scale use in the genomic sequencing space. Part of the reason for this is due to the fact that sequencing technology, such as that described above, is changing very fast. However, presented herein are accelerator implementations for mapping, sequence alignment, sorting, and the like, each of which may comprise an individual block, such as of a sequence analysis pipeline, and may employ one or more of the functions of the various algorithms described herein, in the hardwired from. Accordingly, in various embodiments, methods, apparatuses, and systems disclosed herein may be directed to a partial or complete bio-IT pipeline, that may be implemented in hardware which can combine the processing capability of cloud computing to assist in a complete implementation of the bio-IT pipeline. Applications of the technology, such as in a tertiary processing platform, may include gene expression measurement, splice and structural variant analysis, microRNA analysis, mutation screening, methylation pattern analysis, and DNA binding domain analysis.

For instance, the application of next-gen sequencing and/or secondary and/or tertiary processing, as described herein, may be applied to cancer genomics for the purposes of thoroughly characterizing one or more cancer genomes and/or to assess specific variants, for example in known or putative oncogenes. At least four different analyses can be effectively conducted in accordance with the methods described herein such as in conjunction with next-gen sequencing: For example, structural variation analyses may be performed, such as by sequencing a mate-pair library, e.g., at fairly low coverage of the genome, amplifications, deletions, translocations, and inversions can be detected with genome-wide coverage, which may be implemented in software, as herein described or using a hardware accelerator of the disclosure. Additionally, targeted gene sequencing and analysis may be performed, such as by the selection of "targeted" genes across many samples followed by parallel (e.g., barcoded) sequencing and/or secondary and/or tertiary analysis. Further, transcriptome characterization may be performed, such as for assessment of transcript abundance, splice variants, or both (even for fusion proteins). Furthermore, whole genome sequencing may be performed, such as to characterize small- and large-scale variants across the entire genome, the generated data of which may then be employed in a secondary and/or tertiary processing protocol. All of which may be implemented in software, as herein described, or in the hard wired configuration using a hardware accelerator of the disclosure.

For example, the current class of next-gen sequencers typically performs one task: reading genetic, e.g., DNA, sequences. They can do so on large (about $10^6$-$10^9$) populations of molecules, from many different sources, and the sequence information may be interpreted in many different ways. However, as typically employed, if sequencing a species for which a full genome sequence exists, then, strictly speaking, the sequencing is actually "re-sequencing", regardless of what information will be extracted from the new sequence; and typically this term refers to the identification of SNPs, often in targeted regions of interest. If those regions happen to have a known relation to a human trait (e.g., CYP450 alleles) it may be referred to as "medical re-sequencing."

However, there are a wide variety of applications that can be performed in these manners. More particularly, as summarized in Table 5, below, various applications are provided wherein application areas may be defined both in terms of the particular nucleic acid population selected for sequencing, and the analysis strategy chosen to interpret the sequence information, which again may be performed in software, as herein described, or in the hard wired configuration using a hardware accelerator of the disclosure. It is to be noted, however, that multiple analyses may be performed on the same dataset; for example, expressed SNPs may be present in RNA-Seq data, or genomic SNPs may be present in ChIP-Seq data. Indeed, the presence of SNPs in these datasets can negatively impact the analysis itself.

TABLE 5

| Name | Nucleic acid population | Brief analysis strategy |
| --- | --- | --- |
| RNA-Seq | RNA (may be poly-A mRNA or total RNA) | Alignment of reads to "genes"; variations for detecting splice |

TABLE 5-continued

| Name | Nucleic acid population | Brief analysis strategy |
| --- | --- | --- |
| | | junctions and quantifying abundance |
| Small RNA sequencing | Small RNA (often miRNA) | Alignment of reads to small RNA sequencing references (e.g., miRbase), then to the genome; quantify abundance |
| ChIP-Seq DNA | DNA bound to protein, captured via antibody (ChIP = Chromatin ImmunoPrecipitation) | Align reads to reference genome identify peaks & motifs |
| RIP-Seq | RNA bound to protein, captured via antibody (RIP = RNA ImmunoPrecipitation) | Align reads to reference genome and/or "genes", identify peaks and motifs |
| Methylation Analysis | Select methylated genomic DNA regions, or convert methylated nucleotides to alternate forms | Align reads to reference and either peaks or regions of methylation |
| SNP calling/discovery | All or some genomic DNA or RNA | Either align reads to reference and identify discovery statistically significant SNPs, or compare multiple samples to each other to identify SNPs |
| Structural Variation | Genomic DNA, with two reads (mate-pair reads) per DNA template | Align mate-pairs to reference sequence and interpret structural variants |
| Analysis de novo Sequencing | Genomic DNA (possibly with external data e.g. cDNA, genomes of closely related species, etc.) | Piece-together reads to assemble contigs, scaffolds, and (ideally) whole-genome sequence |
| Metagenomics | Entire RNA or DNA from a (usually microbial) community | Phylogenetic analysis of sequences |

Given the application that needs to be performed, the choice of the platform composition, and which algorithms must be performed, can easily be determined. Almost all epigenetic (ChIP-Seq and methylation analysis) experiments, and many RNA-seq experiments, may be conducted by sequencing only short sections of DNA, as described above, often less than 50 bp because the original material being sequenced is approximately that length. Detection of single-nucleotide polymorphisms (SNPs) and structural variants can also be accomplished with short read lengths. Further, de novo sequencing, discrimination of individual species in pools (e.g., metagenomics) and some RNA-Seq applications may use enough contiguous DNA sequence (e.g., read length) to accurately assemble such reads together unambiguously or match each sequence to the correct location in one or more reference genomes. Typically then, the platform may be configured so as to offer the lowest cost per "mappable/alignable/sortable/etc." base pair, where these activities factors out sequences of low quality and/or low complexity.

Accordingly, in various aspects, we present herein, in certain embodiments, a software and/or hardware architecture for a novel short and long read mapper, aligner, and/or sorter that is both more accurate (e.g., maps, aligns, and/or sorts more reads with fewer errors), and may be up to 10×-100×-1,000× faster than tools such as BWA. Unlike recent aligners based solely on the Burrows-Wheeler transform, a simple hash index of short seed sequences from the genome can be employed, such as in a BioIT pipeline of the disclosure. In certain instances, this approach may greatly reduce the number and cost of local alignment checks performed through several measures: it may use shorter or longer seeds to reduce the false positive locations considered, it may leverage larger memory capacities to speed index lookup, and it may exclude candidate locations without fully computing their edit distance to the read. The result is an algorithm that scales well for reads from one hundred to thousands of bases long and provides a rich error model that can match classes of mutations (e.g., longer indels) that today's fast aligners ignore, which algorithm can be implemented in one or both of software or hardware of the system. It is calculates that the algorithms presented herein above may map, align, and/or sort a dataset with 30×-40×-100×-1,000× coverage of a human genome in minutes with higher accuracy than BWA.

Hence, in various embodiments, a new mapper, aligner, and/or sorter approach is provided that may be substantially faster and/or more accurate than the current algorithms employed, e.g., in software form, that can be implemented in either software and/or hardware, with several properties that may make it attractive and/or broadly applicable, such as for high throughput sequence analysis, secondary, and/or tertiary processing. The mapper, aligner, and/or sorter, and/or other pipeline components are both software and/or hardware friendly. They may be configured to run faster than existing tools on reads from current sequencing technologies, while providing higher accuracy (more reads may be mapped, aligned, and/or sorted with fewer errors), they support a rich error model, e.g., the algorithm(s) may determine alignments with an arbitrary number of substitutions, insertions, and/or deletions from the reference genome, e.g., as long as there is one contiguous "seed" of about 20 bases matching exactly. Such algorithms may be used across a wide range of read lengths (from 100 to 10,000 to 100,000 or more base pairs) and error rates, making it applicable to both current and upcoming sequencing technologies as described above. Additionally, in various embodiments, a hardware architecture for doing the same may be provided wherein the architecture may be implemented on an FPGA/ASIC/sASIC so as to perform the computational genomics pipeline. Like the original BLAST algorithm, the mapping/aligning/sorting algorithms herein presented may be based on a hash index of short substrings of the genome (or other reference database) called seeds, of a fixed size.

Accordingly, in various instances, the present disclosure is directed to a computing architecture that achieves high performance executing algorithms that operate on extremely large data sets that exhibit poor locality of reference (LOR). An example of such a class of algorithms can be found in processing genomic data. The whole human genome contains over 3 billion base pairs. The algorithms designed to reconstruct a whole genome from millions of short read sequences, from modern so-called next generation sequencers, require multi-gigabyte data structures that are randomly accessed. Once reconstruction is achieved, further algorithms with similar characteristics are used to compare one genome to libraries of others, do gene function analysis.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

The invention claimed is:

1. A system for analyzing genetic sequence data, the system comprising:
a memory, the memory comprising one or more genetic reference sequences and an index of the one or more genetic reference sequences;
a structured application specific integrated circuit (ASIC) comprising a plurality of mask-programmed, hard-wired digital logic circuits mask-configured as a plurality of processing engines comprising a mapping module and an alignment module, and
a plurality of physical electrical interconnects comprising an input to the structured ASIC, a memory interface for the structured ASIC, and an output from the structured ASIC;
wherein the input to the structured ASIC is connectable to an electronic data source to receive the plurality of reads of genomic data;
wherein the memory interface for the structured ASIC is configured to access the memory;
wherein the mapping module is configured to access the index of the one or more genetic reference sequences from the memory via the memory interface and configured to map a read to one or more segments of the one or more genetic reference sequences based on the index of the one or more genetic reference sequences;
wherein the alignment module is configured to access the one or more genetic reference sequences from the memory via the memory interface to align the read to one or more positions in the one or more segments of the one or more genetic reference sequences from the mapping module; and
wherein the output from the structured ASIC is configured to communicate result data from the mapping module and/or the alignment module.

2. The system according to claim 1, wherein the mapping module is configured to access the index of the one or more genetic reference sequences according to at least some of the sequence of nucleotides in a read of the plurality of reads.

3. The system according to claim 1 wherein the index of the one or more genetic reference sequences further comprises a hash table, and wherein the mapping module is configured to apply a hash function to the at least some of the sequence of nucleotides to access the hash table of the index.

4. The system according to claim 1 wherein the structured ASIC and the memory are housed on an expansion card.

5. The system according to claim 1 further comprising a sequencer, the sequencer comprising the electronic data source.

6. The system according to claim 5 wherein the structured ASIC is physically integrated with the sequencer.

7. The system according to claim 1 further comprising a cloud computing cluster comprising one or more servers, wherein the structured ASIC is housed in at least one of the one or more servers, the cloud computing cluster further comprising the electronic data source.

8. A structured application specific integrated circuit (ASIC) for analyzing genetic sequence data, the structured ASIC comprising:

a plurality of mask-programmed, hardwired digital logic circuits mask configured as a plurality of processing engines comprising a mapping module and an alignment module; and a plurality of physical electrical interconnects comprising an input to the structured ASIC, a memory interface for the structured ASIC, and an output from the structured ASIC;

wherein the input to the structured ASIC is configured to receive a plurality of reads of genomic data;

wherein the mapping module is configured to access an index of one or more genetic reference sequences via the memory interface and configured to map a read to one or more segments of the one or more genetic reference sequences based on the index of the one or more genetic reference sequences;

wherein the alignment module is configured to access the one or more genetic reference sequences via the memory interface to align the read to one or more positions in the one or more segments of the one or more genetic reference sequences from the mapping module; and wherein the output from the structured ASIC is configured to communicate result data from the mapping module and/or the alignment module.

9. The structured ASIC according to claim 8 wherein the mapping module is configured to access the index of the one or more genetic reference sequences according to at least some of the sequence of nucleotides in a read of the plurality of reads.

10. The structured ASIC according to claim 8 wherein the index of the one or more genetic reference sequences further comprises a hash table, and wherein the mapping module is configured to apply a hash function to the at least some of the sequence of nucleotides to access the hash table of the index.

11. A structured application-specific integrated circuit (ASIC) for analyzing genetic sequence data from an electronic data source that provides digital signals representing a plurality of reads of genomic data, each of the plurality of reads of genomic data comprising a sequence of nucleotides, and using a memory storing one or more genetic reference sequences associated with genomic data and an index of the one or more genetic reference sequences, the structured ASIC comprising:

a master slice that includes a set of digital logic circuits; and one or more configurable metal layers formed on the master slice, each of the one or more configurable metal layers having a set of wired connections, the wired connections of the one or more configurable metal layers being arranged to interconnect a subset of the digital logic circuits to form a set of processing engines, the set of processing engines comprising:

a mapping engine to access the index of the one or more genetic reference sequences from the memory to map the read to one or more segments of the one or more genetic reference sequences based on the index; and an alignment engine to access the one or more genetic reference sequences from the memory to align the read to one or more positions in the one or more segments of the one or more genetic reference sequences from the mapping engine.

12. The structured ASIC in accordance with claim 11, wherein the set of processing engines further comprises a sorting engine to sort each aligned read according to the one or more positions in the one or more genetic reference sequences.

13. The structured ASIC in accordance with claim 11, wherein a portion of the set of digital logic circuits is hardwired in the master slice as a base calling engine to analyze the genetic sequence data from the electronic data source to determine a most likely nucleotide at each position sequenced by the sequencer, and to estimate a confidence of the most likely nucleotide.

14. The structured ASIC in accordance with claim 11, wherein a portion of the set of digital logic circuits is hardwired in the master slice as one or more embedded processor cores.

15. The structured ASIC in accordance with claim 14, wherein one or more processing engines of the set of processing engines are connected to the one or more embedded processor cores via the one or more configurable metal layers formed on the master slice.

16. The structured ASIC in accordance with claim 11, wherein the set of processing engines further comprises a primary analysis pipeline engine, the primary analysis pipeline engine executing on the genomic data one or more of: signal processing, image processing, base calling, and base call quality estimation.

17. A method of making a structured application-specific integrated circuit (ASIC) for analyzing genetic sequence data, the method comprising:

providing a plurality of photolithographic masks that define a set of digital logic circuits of the structured ASIC;

forming the set of digital logic circuits using the plurality of photolithographic masks to form a first master slice and a second master slice that is equivalent to the first master slice;

providing a first set of configurable metal layer masks that define a first digital logic configuration;

forming a first set of configurable metal layers onto the first master slice using the first set of configurable metal layer masks, the first set of configurable metal layers having a set of wired connections arranged according to the first set of configurable metal layer masks to interconnect a subset of the digital logic circuits of the first master slice according to the first digital logic configuration;

providing a second set of configurable metal layer masks that define a second digital logic configuration;

forming a second set of configurable metal layers onto the second master slice using the second set of configurable metal layer masks, the second set of configurable metal layers having a set of wired connections arranged according to the second set of configurable metal layer masks to interconnect a subset of the digital logic circuits of the second master slice according to the second digital logic configuration;

the first digital logic configuration including an input for connecting to an electronic data source that provides digital signals representing a plurality of reads of genomic data, each of the plurality of reads of genomic data comprising a sequence of nucleotides, the first digital logic configuration further including a memory interface to a memory storing one or more genetic reference sequences associated with genomic data and an index of the one or more genetic reference sequences; and the first digital logic configuration further including a set of processing engines, the set of processing engines comprising a mapping engine to access the index of the one or more genetic reference sequences from the memory to map the read to one or more segments of the one or more genetic reference sequences based on the index.

18. An apparatus for analyzing genetic sequence data, the genetic sequence data comprising one or more genetic reference sequences and one or more reads of genomic data, the apparatus comprising:

a memory comprising one or more genetic reference sequences and an index of the one or more genetic reference sequences;

a structured application specific integrated circuit (ASIC) comprising a plurality of physical electrical interconnects comprising an input to the structured ASIC configured to receive one or more reads of the genomic sequence data, a memory interface for the structured ASIC, and an output from the structured ASIC;

a plurality of mask-programmed, hardwired digital logic circuits interconnected by the plurality of physical electrical interconnects, the plurality of mask-programmed, hardwired digital logic circuits mask-configured to access, according to at least some of the sequence of nucleotides in at least one read of the one or more reads of genomic data, the index of the one or more genetic reference sequences from the memory via the memory interface, map the at least one read of the one or more reads of genomic data to one or more segments of the one or more genetic reference sequences based on the index, access the one or more genetic reference sequences from the memory via the memory interface, and align the read to one or more positions in the one or more segments of the one or more genetic reference sequences.

* * * * *